(12) United States Patent
Princen et al.

(10) Patent No.: US 9,512,482 B2
(45) Date of Patent: Dec. 6, 2016

(54) COMPOSITIONS AND METHODS FOR DETECTING ALLELIC VARIANTS

(71) Applicant: NESTEC S.A., Vevey (CH)

(72) Inventors: Fred Princen, La Jolla, CA (US); Fabiyola Selvaraj, San Diego, CA (US); Sharat Singh, Rancho Sante Fe, CA (US)

(73) Assignee: Nestec S.A., Vevey (CH)

( * ) Notice: Subject to any disclaimer, the term of this patent is extended or adjusted under 35 U.S.C. 154(b) by 115 days.

(21) Appl. No.: 14/182,718

(22) Filed: Feb. 18, 2014

(65) Prior Publication Data

US 2014/0248612 A1    Sep. 4, 2014

Related U.S. Application Data

(63) Continuation of application No. PCT/US2012/051442, filed on Aug. 17, 2012.

(60) Provisional application No. 61/588,151, filed on Jan. 18, 2012, provisional application No. 61/525,137, filed on Aug. 18, 2011.

(51) Int. Cl.
*C12Q 1/68* (2006.01)
*C12P 19/34* (2006.01)

(52) U.S. Cl.
CPC ........... *C12Q 1/6883* (2013.01); *C12Q 1/6851* (2013.01)

(58) Field of Classification Search
None
See application file for complete search history.

(56) References Cited

U.S. PATENT DOCUMENTS

| 5,554,516 A | 9/1996 | Kacian et al. | |
|---|---|---|---|
| 2011/0086354 A1 | 4/2011 | Tzubery et al. | |
| 2011/0129832 A1* | 6/2011 | Makarov | C12Q 1/6818 435/6.11 |

FOREIGN PATENT DOCUMENTS

| WO | 2005/017181 A2 | 2/2005 |
|---|---|---|
| WO | 2010/111682 A2 | 9/2010 |

OTHER PUBLICATIONS

Noir, R. et al., "Oligonucleotide-oligospermine conjugates (zip nucleic acids): a convenient means of finely tuning hybridization temperatures," J. American Chem. Soc., 130(40): 1350-13505, 2008.
Isobe, H. et al., "Triazole-linked analogue of deoxyribonucleic acid (TL DNA): design, synthesis, and double-strand formation with natural DNA," Organic Letters, 10(17):3729-3732, 2008.
Latorra, D. et al., "Enhanced allele-specific PCR discrimination in SNP genotyping using 3' locked nucleic acid (LNA) primers," Human Mutation, John Wiley & sons, Inc., 22(1): 79-85, 2003.
Morlan, J. et al., "Mutation Detection by Real-Time PCR: A Simple, Robust and Highly Selective method," PLOS One, Public Library of Science, US, 4(2): e4584-1, 2009.

* cited by examiner

*Primary Examiner* — Jehanne Sitton
(74) *Attorney, Agent, or Firm* — Kilpatrick Townsend and Stockton LLP

(57) ABSTRACT

The present invention provides compositions, methods, and kits for discriminating sequence variation between different alleles. More specifically, in some embodiments, the present invention provides compositions, methods, and kits for determining the presence and/or level (e.g., quantitating) of rare (e.g., mutant) allelic variants, such as single nucleotide polymorphisms (SNPs) or nucleotide insertions or deletions, in samples comprising abundant (e.g., wild-type) allelic variants with high sensitivity and/or specificity. As such, in certain embodiments, the present invention provides a highly selective method for the detection of somatic mutations, e.g., in samples containing abundant levels of a wild-type allele compared to very low levels of a mutant allele.

13 Claims, 49 Drawing Sheets

Serial dilution of KPL4 cells (H1047R positive) spike in Whole Blood : $10^5$; $10^4$; $10^3$; $10^2$; 10 cells Serial dilution of KPL4 (H1047R), A549 (G12S) and PSN1 (G12R) spike in Whole Blood (WB) 10, 50, 100, 250 and 500cells

| | Total DNA Amount (GE) | Gene | Mutation | Call | Cell number mixed in WB |
|---|---|---|---|---|---|
| 1 | 22349 | KRAS G12S | g34a | wildtype | A549 10cells |
| 2 | 40374 | KRAS G12S | g34a | wildtype | A549 50cells |
| 3 | 60624 | KRAS G12S | g34a | wildtype | A549 100cells |
| 4 | 39712 | KRAS G12S | g34a | wildtype | A549 250cells |
| 5 | 12141 | KRAS G12S | g34a | wildtype | A549 500cells |
| 6 | 11273 | KRAS G12S | g34a | wildtype | A549 0cells |
| 7 | 23294 | PIK3CA H1047R | a3140g | wildtype | KPL4 10cells |
| 8 | 5217 | PIK3CA H1047R | a3140g | wildtype | KPL4 50cells |
| 9 | 25339 | PIK3CA H1047R | a3140g | wildtype | KPL4 100cells |
| 10 | 5535 | PIK3CA H1047R | a3140g | wildtype | KPL4 250cells |
| 11 | 34603 | PIK3CA H1047R | a3140g | wildtype | KPL4 500cells |
| 12 | 9885 | PIK3CA H1047R | a3140g | wildtype | KPL4 0cells |
| 13 | 101949 | KRAS G12R | g34c | wildtype | PSN-1 10cells |
| 14 | 207276 | KRAS G12R | g34c | wildtype | PSN-1 100cells |
| 15 | 189448 | KRAS G12R | g34c | mutant* (0.82%) | PSN-1 10e3cells |

Inostics assay only detected the mutation when 1000 cells were present in Whole blood.

Summary
A total of one mutation could be found in the KRAS gene. Although this mutation failed to display the required mutation frequency of 1% (marked with *), it shows clear signs of a mutation and was hence called.

FIG. 11

Serial dilution of KPL4 (H1047R), A549 (G12S) and PSN1 (G12R) spike in Whole Blood (WB) 10, 50, 100, 250 and 500cells

H1047R

| | Inventive Assay | Inostics |
|---|---|---|
| KPL4 0cells | 36.00 | Wild type |
| KPL4 10cells | 35.70 | Wild type |
| KPL4 50cells | 35.77 | Wild type |
| KPL4 100cells | 34.18 | Wild type |
| KPL4 250cells | 34.39 | Wild type |
| KPL4 500cells | 33.97 | Wild type |

G12S

| | Inventive Assay | Inostics |
|---|---|---|
| A549 0cells | 36.20 | Wild type |
| A549 10cells | 36.15 | Wild type |
| A549 50cells | 35.00 | Wild type |
| A549 100cells | 34.70 | Wild type |
| A549 250cells | 34.35 | Wild type |
| A549 500cells | 33.65 | Wild type |

G12R

| | Inventive Assay | Inostics |
|---|---|---|
| PSN-1 0cells | 35.37 | Wild type |
| PSN-1 10cells | 34.43 | Wild type |
| PSN-1 100cells | 30.54 | Wild type |
| PSN-1 10e3cells | 26.87 | Mutant |

- Inostics assay only detect 1000 cells in the mix. The assay has no sensitivity by 500 cells
- Inventive Assay has detectable signal as low as 50 to 100 positive cells in WB mix.
100 cells represent 0.01% of the whole blood count.

*FIG. 12*

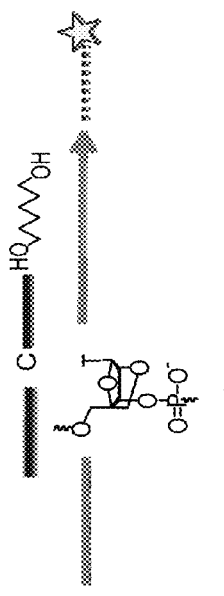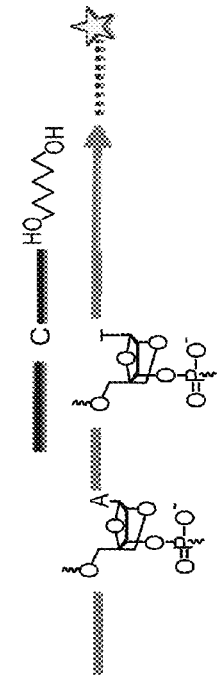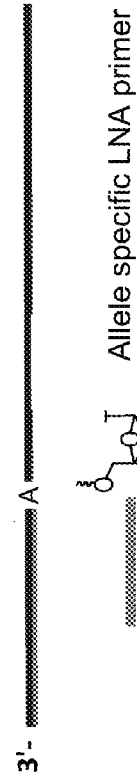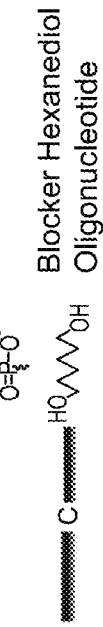
FIG. 15

Locked Nucleic Acid (LNA)

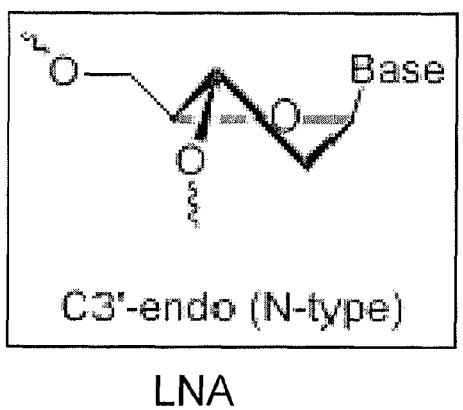

LNA

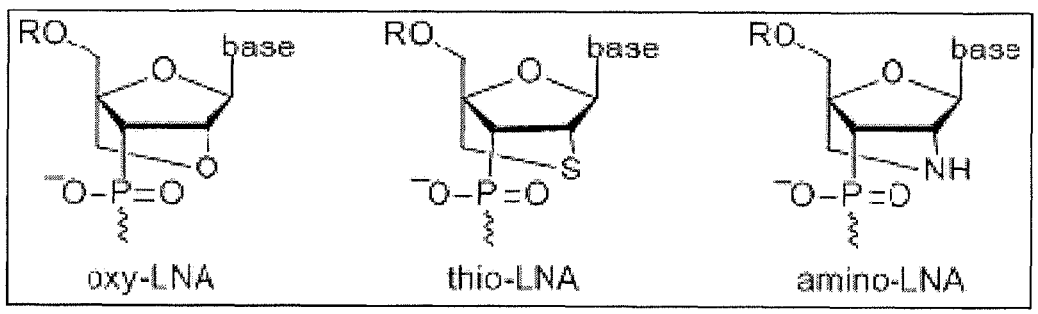

Modifications of LNA

- LNA is an unnatural conformationally restricted oligonucleotide analogue with a close structural resemblance to DNA, possessing monomer units with a 2'-O-4'-C-methylene bridge.

- The bicyclic structure locks the molecule in a C3'-endo sugar (N-type) configuration ensuring the oligonucleotide adopts the A-form helix which is associated with high duplex stability.

*FIG. 17*

Allele-specific Primer With Triazole DNA (TzDNA)

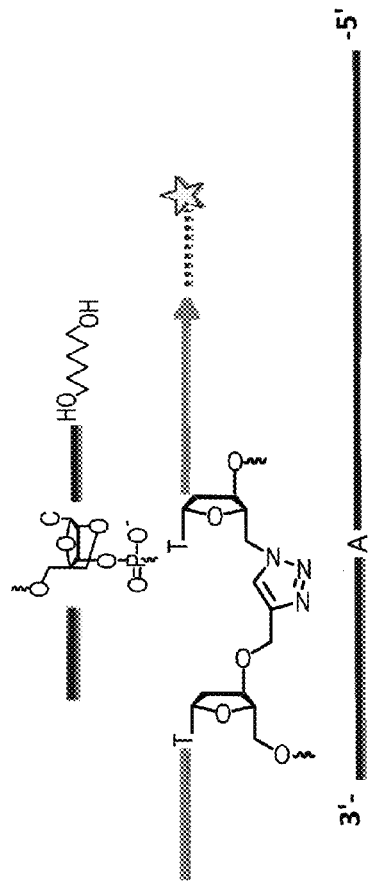

Triazole DNA (Tz DNA)

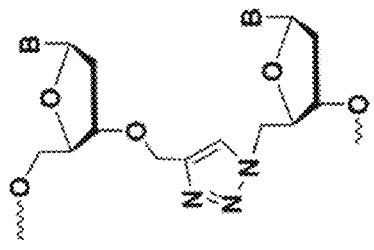

- TzDNA oligonucleotides have triazole linkages instead of the normal phosphate backbone.

- The oligomers with single and double modification with 1,2,3-triazole unit show an increase in melting temperature of the DNA complex.

- The non-natural linkages also protect the primers from 5'-exonuclease activity.

- The TzDNA modification exhibit thermal stability towards complementary DNA which allows excellent mismatch discrimination.

*FIG. 21*

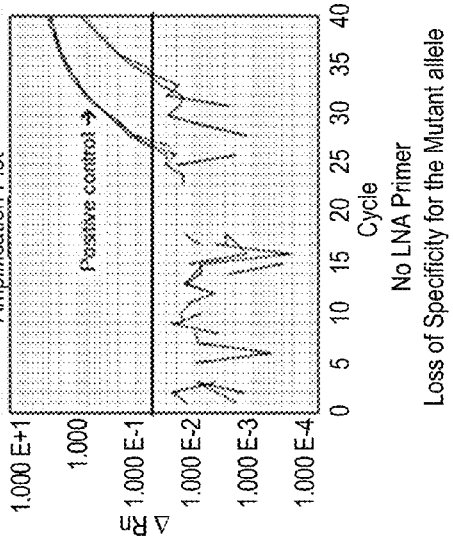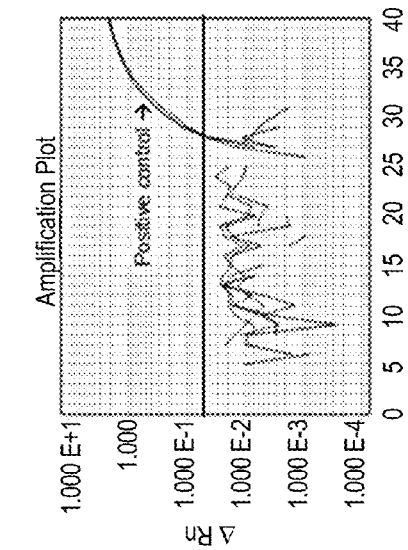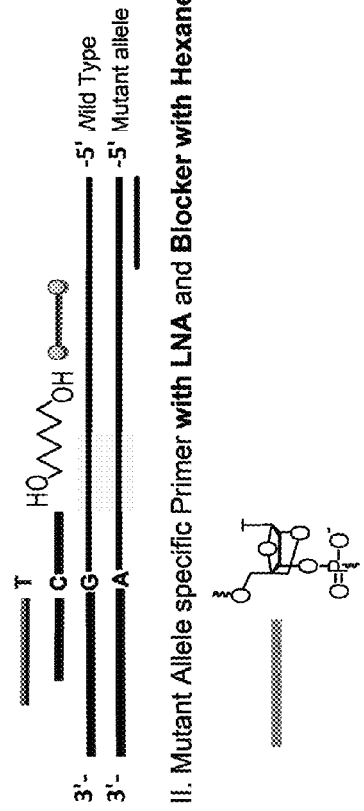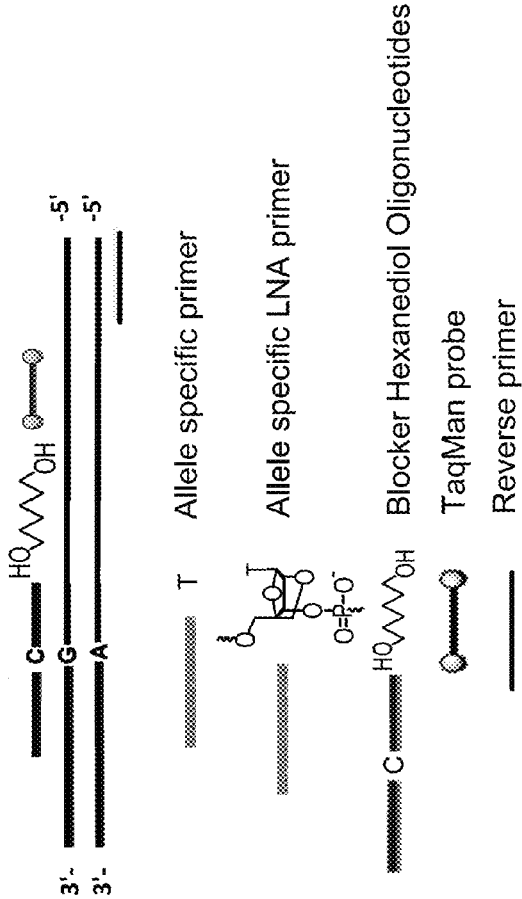
FIG. 23

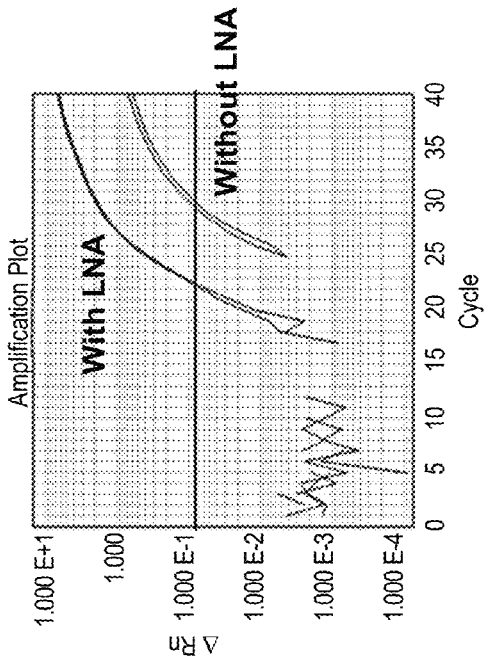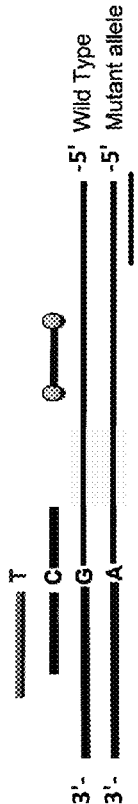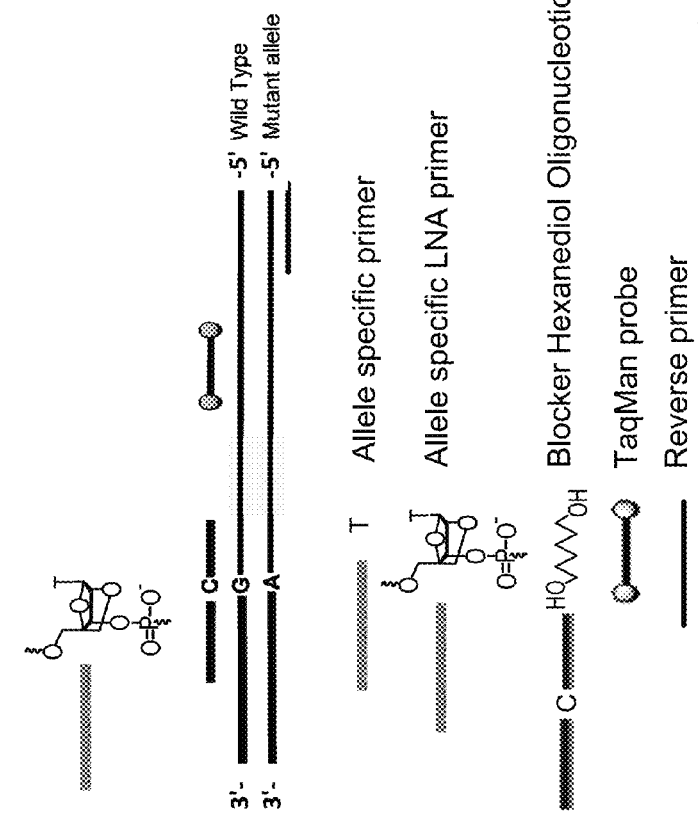
FIG. 25

Experiment #10: Position of LNA in Blocker Probe
Mutant Allele specific Primer with LNA and with Blocker.1.LNA
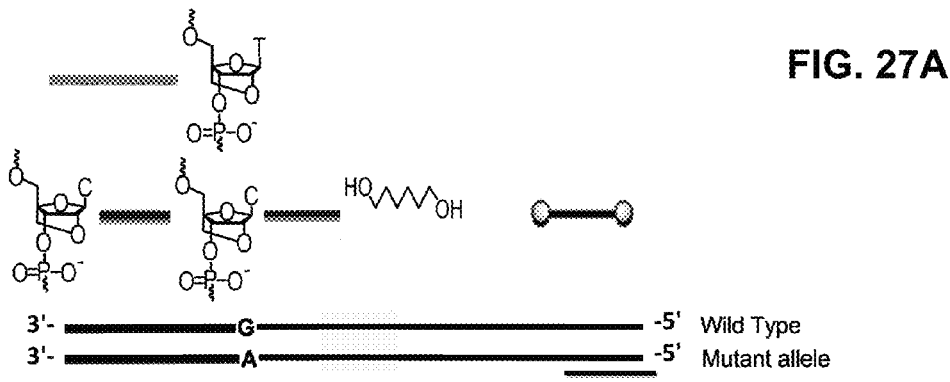
FIG. 27A
Mutant Allele specific Primer with LNA and with Blocker.4.LNA
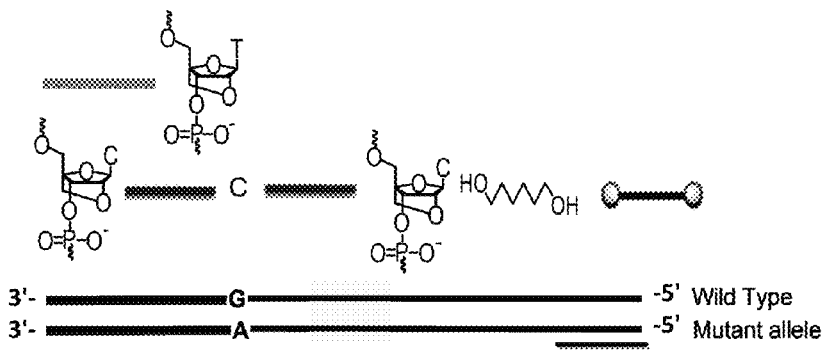
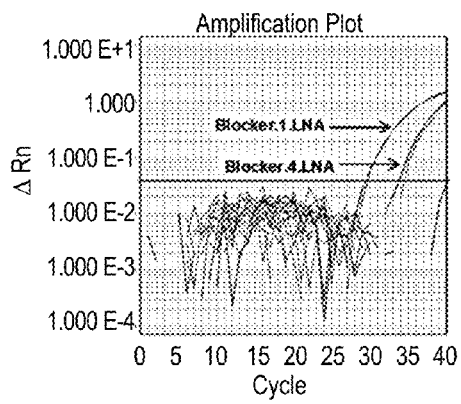
FIG. 27B
| | Blocker Sequence | Tm |
|---|---|---|
| Blocker.1.LNA | +TTG GAG CTG +<u>G</u>TG GCG TAG G/3'C6/ | 67°C |
| Blocker.4.LNA | +TTG GAG CTG <u>G</u>TG GCG TAG +G /3'C6/ | 68°C |
+ indicates LNA; allelic variant is underlined

Blocker Probes and Melting Temperature (Tm)

| Blocker Sequence | Tm |
|---|---|
| TTG GAG CTG GTG GCG TAG G /3'C6/ | 59.9°C |
| +TTG GAG CTG GTG GCG TAG +G /3'C6/ | 68°C |

+ indicates LNA; Tm: Melting Temperature

Blocker with LNA and higher Tm:
a) Better the specificity for allelic variant
b) Better sensitivity
c) Efficient inhibition of the wild type

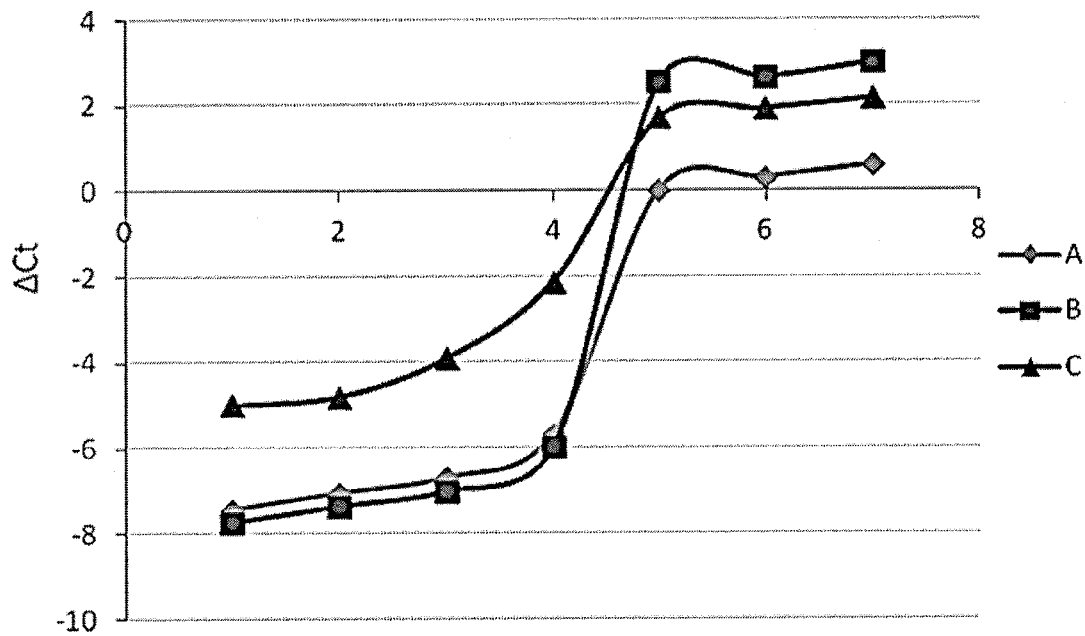

B: ΔCt = Ct ASP LNA − Ct ASP
C: ΔCt = Ct WT − Ct ASP

The difference in Ct (ΔCt) between the wild type and Allele-Specific Primer (ASP) Ct values is an approximation of the assay selectivity. ΔCt was calculated from the Ct values from the assays of ASP with LNA / ASP without LNA / Wild Type (WT) Primer with various blocker LNAs.

The higher ΔCt was obtained with the use of LNA on the ASP and on the blocker indicating the feasibility and selectivity of the assay.

*FIG. 30*

D D Ct Plots

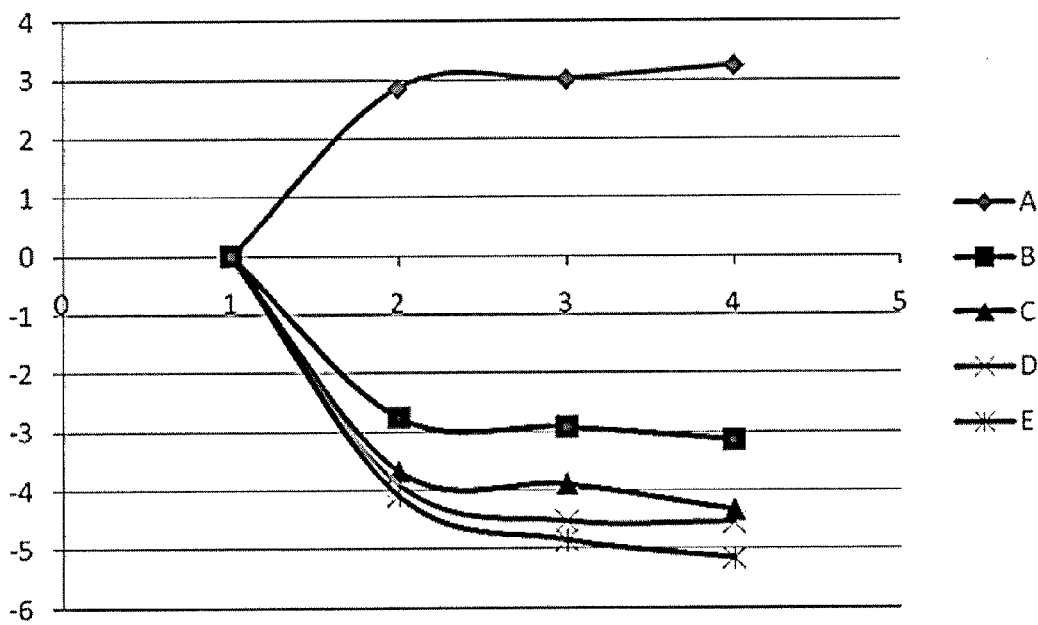

ΔΔCt was calculated from the Ct values from various somatic mutation genotyping assays.

ΔΔCt = (Ct WT - Ct ASP) - (Ct ASP - Ct ASP LNA)

The assays comprise of allele-specific primer (ASP) with LNA, ASP without LNA or wild-type (WT) primer, and various blocker LNA probes.

Assay A was designed with LNA on the ASP and the blocker probe. It worked better than assays with a blocker probe without LNA and either the WT primer or a ASP without LNA.

Assays B, C, D, and E did not work. In these assays more than one LNA was placed consecutively on the ASP and/or the blocker probe.

*FIG. 31*

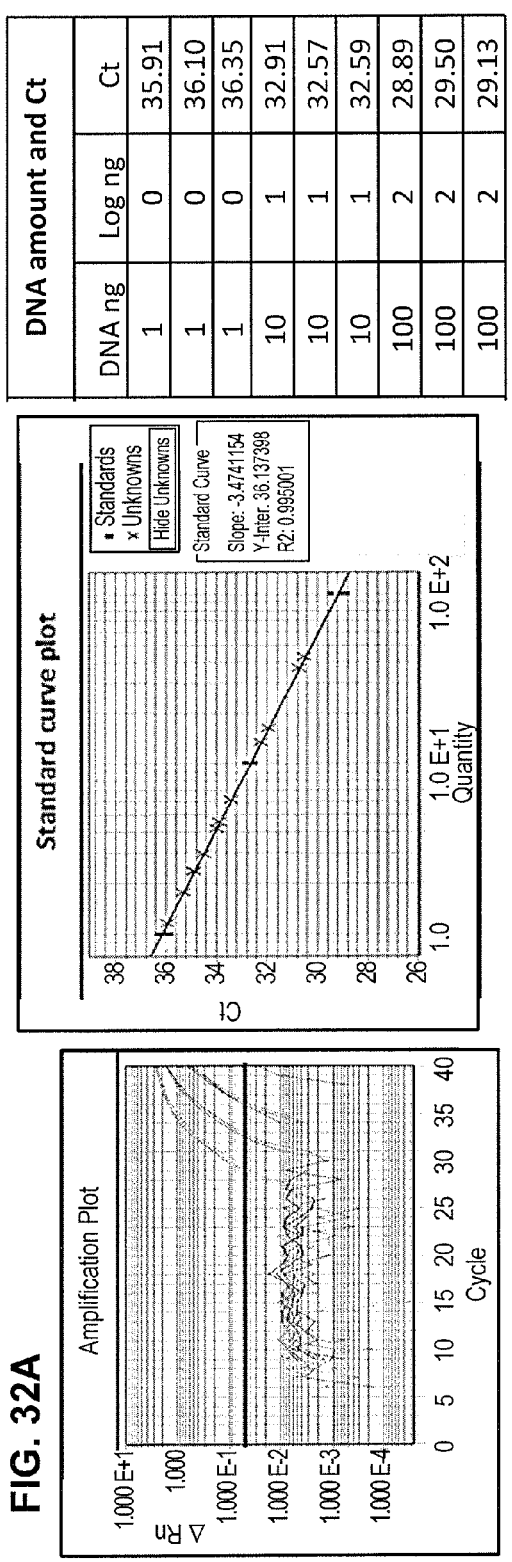
FIG. 32A
FIG. 32B
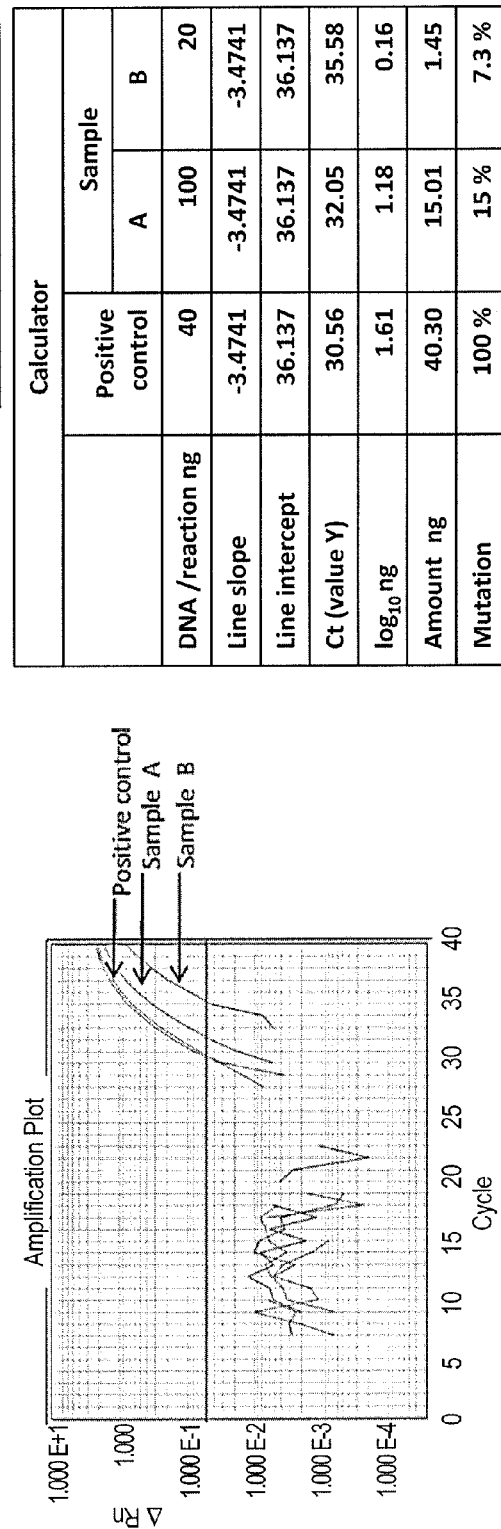
FIG. 32C

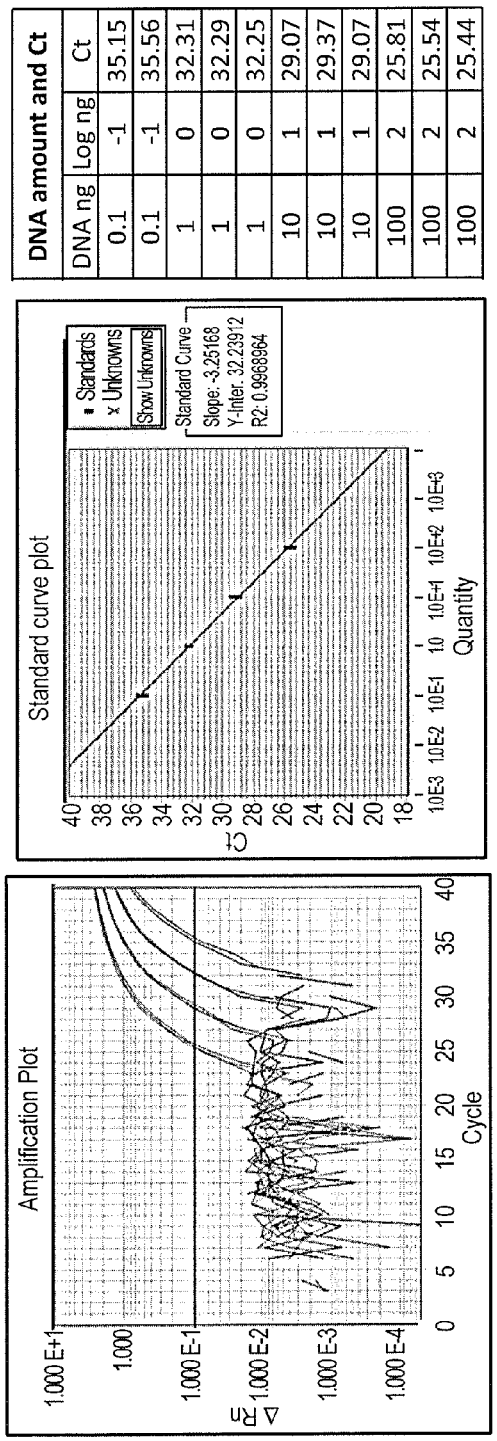
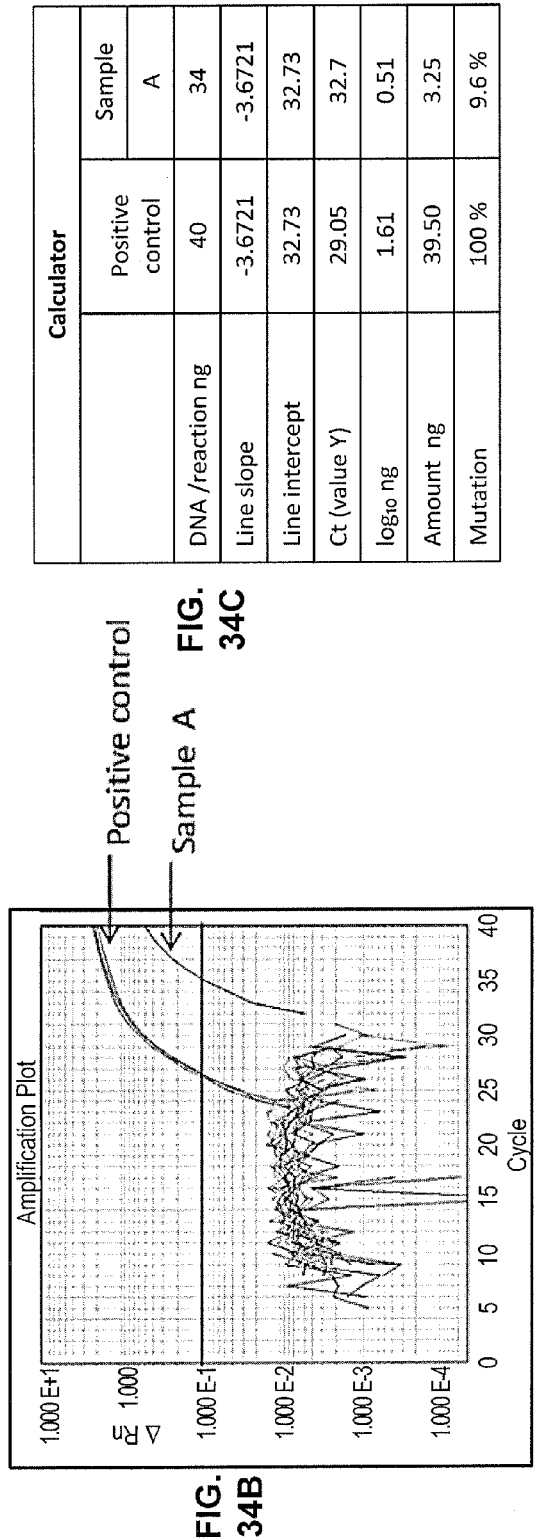
FIG. 34A
FIG. 34B
FIG. 34C

| DNA amount and Ct | | |
|---|---|---|
| DNA ng | Log ng | Ct |
| 0.01 | -2 | 40 |
| 0.01 | -2 | 40 |
| 0.01 | -2 | 40 |
| 0.1 | -1 | 35.57 |
| 0.1 | -1 | 37.05 |
| 0.1 | -1 | 35.83 |
| 1 | 0 | 32.15 |
| 1 | 0 | 32.11 |
| 1 | 0 | 32.76 |
| 10 | 1 | 28.57 |
| 10 | 1 | 28.56 |
| 10 | 1 | 28.54 |
| 100 | 2 | 25.04 |
| 100 | 2 | 24.85 |
| 100 | 2 | 25.06 |

| Calculator | Positive control | Sample A |
|---|---|---|
| DNA /reaction ng | 40 | 15 |
| Line slope | -3.762 | -3.762 |
| Line intercept | 32.407 | 32.407 |
| Ct (value Y) | 26.4 | 35.03 |
| $\log_{10}$ ng | 1.60 | -0.74 |
| Amount ng | 39.51 | 0.18 |
| Mutation | 100 % | 1.2 % |

Hematoxylin & Eosin Stained Frozen Sections of Non-Small Cell Lung Cancer Tumor Samples

FIG. 37A

CK Values and Somatic Mutational Analysis of Gastric Tumor Samples

| Sample | CK | Mutation |
|---|---|---|
| 1 | 1422.1 | T790M (0.2%) |
| 2 | 1897.84 | G12V(2.3%), Q61H (0.5%) |
| 4 | 1177.38 | E545K (0.6%) |
| 5 | 1598.06 | G13D 90% |

High level of CK with low % mutation. Not all the tumor cells are likely to carry the mutation High level of CK with High G13D % mutation. Most of the tumor cells are likely to carry the mutation.

FIG. 37B

CK Values and Somatic Mutational Analysis of Pancreatic Tumor Samples

| Sample | CK | Mutation |
|---|---|---|
| 1 | 2200 | G12D (100%) |
| 3 | 1400 | G12D (5%) |

High level of CK with high % mutation. Most of the tumor cells are likely to carry the mutation.

High level of CK with low % mutation. Not all the tumor cells are likely to carry the mutation.

| Number of Positive Tumor Cells (SW116 Cells) in the Sample | Inventive Somatic Mutation Genotyping Assay | Life Technologies' cast PCR Mutation Assay |
|---|---|---|
| 0 | 40 | 40 |
| 10 | 40 | 40 |
| 50 | 40 | 40 |
| 100 | 37.22 | 39.04 |
| 250 | 40 | 40 |
| 500 | 36.00 | 40 |
| 1,000 | 36.12 | 38.58 |
| 2,000 | 34.92 | 40 |
| | 34.89 | 36.91 |
| | 33.49 | 37.69 |
| | 33.95 | 36.53 |
| | 33.84 | 38.40 |
| 10,000 | 34.18 | 38.55 |
| | 29.36 | 32.55 |
| 100,000 | 30.11 | 32.01 |
| | 26.34 | 29.53 |
| | 26.35 | 28.85 |
FIG. 38C
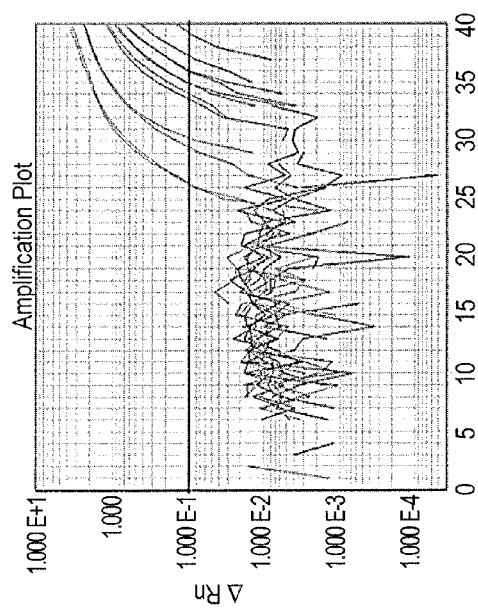
FIG. 38A
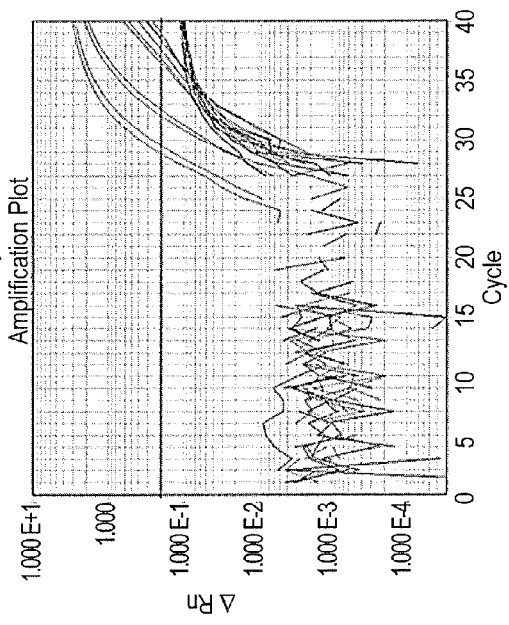
FIG. 38B

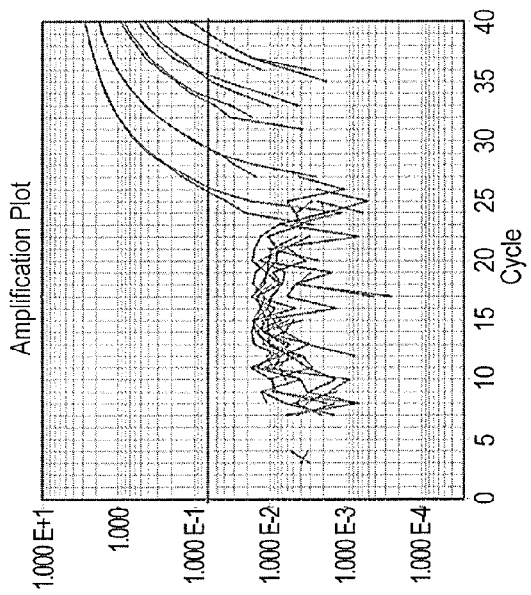
FIG. 39A
FIG. 39B
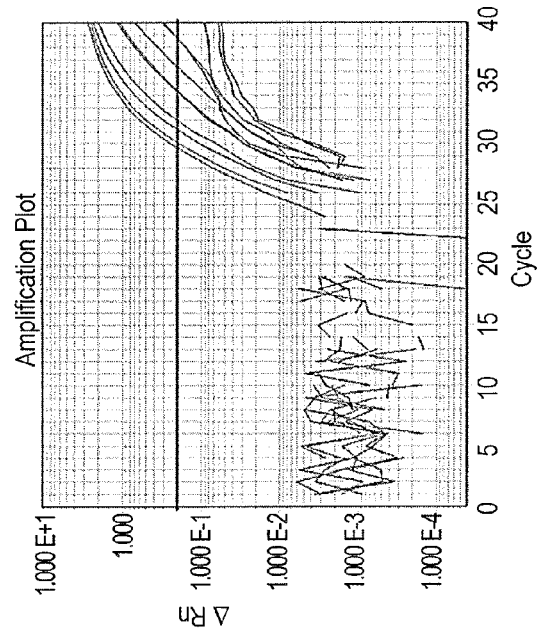
FIG. 39C
| Number of Positive Tumor Cells (A549 Cells) in the Sample | Inventive Somatic Mutation Genotyping Assay | Life Technologies' castPCR™ Mutation Assay |
|---|---|---|
| 0 | 37.85 | 40 |
|  | 40 | 40 |
| 10 | 38.95 | 40 |
|  | 39.09 | 38.65 |
| 100 | 35.59 | 36.37 |
|  | 35.22 | 38.68 |
| 1,000 | 33.19 | 34.28 |
|  | 33.56 | 34.39 |
| 10,000 | 29.33 | 31.13 |
|  | 29.41 | 31.93 |
| 100,000 | 25.76 | 29.63 |
|  | 26.20 | 30.08 |

Percent Mutation of Breast Cancer Samples

| Test# | Nanodrop ng/uL | PIK3CA H1047R | PIK3CA E542K | PIK3CA E545K | PIK3CA E545D | EGFR T790M | EGFR L858R | KRAS G12A | KRAS G12C | KRAS G12D | KRAS G12R | KRAS G12S | KRAS G12V | KRAS G13D | BRAF V600E |
|---|---|---|---|---|---|---|---|---|---|---|---|---|---|---|---|
| 1 | 16.3 | +(12%) | - | - | - | - | - | - | - | - | - | - | - | - | - |
| 2 | 2.8 | +(1%) | - | - | - | - | - | - | - | - | - | - | - | - | - |
| 3 | 21.5 | +(3%) | - | - | - | - | - | - | - | - | - | - | - | - | - |
| 4 | 11 | +(10%) | - | - | - | - | - | - | - | - | - | - | - | - | - |
| 5 | 37.1 | +(3%) | - | - | - | - | - | - | - | - | - | - | - | - | - |
| 6 | 1.7 | - | - | - | - | - | - | - | - | - | - | - | - | - | - |
| 7 | 3.8 | - | - | - | - | - | - | - | - | - | - | - | - | - | - |
| 8 | 3.4 | - | - | - | - | - | - | - | - | - | - | - | - | - | - |
| 9 | 6.2 | - | - | - | - | - | - | - | - | - | - | - | - | - | - |
| 10 | 3.6 | - | - | - | - | - | - | - | - | - | - | - | - | - | - |
| 11 | 3.2 | - | - | - | - | - | - | - | - | - | - | - | - | - | - |
| 12 | 3 | - | - | - | - | - | - | - | - | - | - | - | - | - | - |
| 13 | 4 | - | - | - | - | - | - | - | - | - | - | - | - | - | - |
| 14 | 1.8 | - | - | - | - | - | - | - | - | - | - | - | - | - | - |
| 15 | 4.9 | - | - | - | - | - | - | - | - | - | - | - | - | - | - |
| 16 | 3.5 | - | - | - | - | - | - | - | - | - | - | - | - | - | - |
| 17 | 3.7 | - | - | - | - | - | - | - | - | - | - | - | - | - | - |
| 18 | 1.9 | - | - | - | - | - | - | - | - | - | - | - | - | - | - |
| 19 | 4.6 | - | - | - | - | - | - | - | - | - | - | - | - | - | - |
| 20 | 2.7 | - | - | - | - | - | - | - | - | - | - | - | - | - | - |
| 21 | 4.5 | - | - | - | - | - | - | - | - | - | - | - | - | - | - |
| 22 | 2.2 | - | - | - | - | - | - | - | - | - | - | - | - | - | - |
| 23 | 2.7 | - | - | - | - | - | - | - | - | - | - | - | - | - | - |
| 24 | 4.3 | - | - | - | - | - | - | - | - | - | - | - | - | - | - |
| 25 | 4.3 | - | - | - | - | - | - | - | - | - | - | - | - | - | - |
| 26 | 5.4 | - | - | - | - | - | - | - | - | - | - | - | - | - | - |
| 27 | 5.1 | - | + | - | - | - | - | - | - | - | - | - | - | - | - |
| 28 | 4.5 | - | - | - | - | - | - | - | - | - | - | - | - | - | - |
| 29 | 8.4 | - | - | - | - | - | - | - | - | - | - | - | - | - | - |
| 30 | 1.9 | - | - | - | - | - | - | - | - | - | - | - | - | - | - |
| 31 | 2.5 | - | - | - | - | - | - | - | - | - | - | - | - | - | - |
| 32 | 2.8 | - | - | - | - | - | - | - | - | - | - | - | - | - | - |
| 33 | 5.8 | +(41%) | - | - | - | - | - | - | - | - | - | - | - | - | - |
| 34 | 11.4 | - | - | +(100%) | - | - | - | - | - | - | - | - | - | - | - |
| 35 | 3.2 | - | - | - | - | - | - | - | - | - | - | - | - | - | - |
| 36 | 3.4 | - | - | - | - | - | - | - | - | - | - | - | - | - | - |
| 37 | 3.4 | - | - | - | - | - | - | - | - | - | - | - | - | - | - |
| 38 | 3 | - | - | - | - | - | - | - | - | - | - | - | - | - | - |
| 39 | 1.7 | - | - | - | - | - | - | - | - | - | - | - | - | - | - |
| 40 | 4.1 | - | - | - | - | - | - | - | - | - | - | - | - | - | - |
| 41 | 1.2 | - | - | - | - | - | - | - | - | - | - | - | - | - | - |
| 42 | 6.6 | - | - | - | - | - | - | - | - | - | - | - | - | - | - |
| 43 | 3.2 | - | - | - | - | - | - | - | - | - | - | - | - | - | - |

*FIG. 40*

Percent Mutation of Breast Cancer Samples

| Sample ID | DNA con. ng/μl | Serial # | PIK3CA | | | |
|---|---|---|---|---|---|---|
| | | | E542K | E545D | E545K | H1047R |
| 770 | 1.7 | 1 | | | | |
| 739 | 13 | 2 | | | | |
| 746 | 47.4 | 3 | | | | H1047R (89%) |
| 748 | 17.2 | 4 | | | | |
| 749 | 19.8 | 5 | | | | |
| 755 | 16.1 | 6 | | | | |
| 756 | 33.1 | 7 | | | | |
| 757 | 45 | 8 | | | | |
| 759 | 27.8 | 9 | | | | |
| 760 | 10.7 | 10 | | | | |
| 764 | 6.9 | 11 | | | | |
| 771 | 22.4 | 12 | | | | |
| 772 | 17.2 | 13 | | | | |
| 773 | 36.6 | 14 | | | | |
| 774 | 8 | 15 | | | | |
| 775 | 9 | 16 | | | | H1047R (51.8%) |
| 776 | 29.2 | 17 | | | | |
| 778 | 6.9 | 18 | | | | |
| 779 | 8.9 | 19 | | | | |
| 782 | 60 | 20 | | | | |
| 783 | 15.3 | 21 | | | | |
| 740 | 10.9 | 22 | | | | H1047R (6.8%) |
| 742 | 9.1 | 23 | | | | |
| 753 | 23.7 | 24 | | | | |
| 741 | 41.6 | 25 | | | | |
| 743 | 12.7 | 26 | | | | H1047R (100%) |
| 744 | 14.7 | 27 | E542K (0.13%) | | | |
| 745 | 6.5 | 28 | | | | |
| 747 | 60.3 | 29 | | | | |
| 750 | 22 | 30 | | | | |
| 751 | 5.7 | 31 | | | | |
| 754 | 29.6 | 32 | | | | |
| 758 | 45.5 | 33 | | | | |
| 752 | 25.2 | 34 | | | | |
| 761 | 62.4 | 35 | | | | |
| 762 | 26.9 | 36 | E542K (2%) | | | |
| 763 | 21.8 | 37 | | | | |
| 765 | 19.6 | 38 | | | | |
| 766 | 30.6 | 39 | | | | |
| 767 | 17.8 | 40 | E542K (3.55%) | | | |
| 768 | 20.7 | 41 | | | | H1047R (5.9%) |
| 769 | 7.3 | 42 | | | | |
| 777 | 20.4 | 43 | | | | |
| 780 | 12.1 | 44 | | | | |
| 781 | 38.7 | 45 | | | | |

*FIG. 41*

Percent Mutation of Lung Tumor Samples

| Sample ID | DNA con. ng/μl | Serial # | PIK3CA E542K | PIK3CA E545D | PIK3CA E545K | PIK3CA H1047R | EGFR T790M | EGFR L858R | EGFR E746 del | KRAS G12C | KRAS G12R | KRAS G12S | KRAS G12D | KRAS G12A | KRAS G12V | KRAS G13C | KRAS G13D | KRAS Q61H | BRAF V600E |
|---|---|---|---|---|---|---|---|---|---|---|---|---|---|---|---|---|---|---|---|
| 161 | 49.6 | 1 | | | | | | | | | | | | | | | | | |
| 162 | 125.8 | 2 | | | | | | | | | | | | | | | | | |
| 163 | 232 | 3 | | | | | | | | | | | | | | | | | |
| 164 | 27.9 | 4 | | | | | | | E746 del (0.1%) | | | | | | | | | | |
| 165 | 84.4 | 5 | | | | | | | | | | | | | | | | | |
| 211 | 98.2 | 6 | | | | | | | | | | | | | | | | | |
| 212 | 71.4 | 7 | | | | | | | | | | | | | | | | | |
| 213 | 149.9 | 8 | | | | | | | | | | | | | | | | | V600E(0.2%) |
| 214 | 104 | 9 | | | | | | | | | | | | | | | | | |
| 215 | 242.4 | 10 | | | | | | | | | | | | | | | | | |
| 351 | 62.6 | 11 | | | | | | | | | | | | | | | | | |
| 352 | 102.7 | 12 | | | E545K (100%) | | | | | | | | | | | | | | |
| 353 | 5.3 | 13 | | | E545K (100%) | | | | | | | | | | | | | | |
| 354 | 161.2 | 14 | | | E545K (100%) | | | | | | | | | | | | | | |
| 355 | 39.4 | 15 | | | E545K (100%) | | | | | | | | | | | | | | |
| 371 | 117.8 | 16 | | | | | | L858R (100%) | | | | | | | | | | | |
| 372 | 146.6 | 17 | | | | | | L858R (100%) | | | | | | | | | | | |
| 373 | 111.2 | 18 | | | | | | L858R (100%) | | | | | | | | | | | |
| 374 | 96.1 | 19 | | | | | | L858R (100%) | | | | | | | | | | | |
| 375 | 123.5 | 20 | | | | | | L858R (100%) | | | | | | | | | | | |
| 381 | 152.4 | 21 | | | | | | | E746 del (0.2%) | | | | | | | | | | |
| 382 | 383.8 | 22 | | | | | | | | | | | | | | | | | |
| 383 | 123.4 | 23 | | | | | | | | | | | | | | | | | |
| 384 | 110.3 | 24 | | | | | | | | | | | | | | | | | |
| 385 | 22.1 | 25 | | | | | | | | | | | | | | | | | |

FIG. 42

Percent Mutation of Human Lung Tumor Samples

| # | NanoDrop ng/uL | PIK3CA E542K | PIK3CA E545D | PIK3CA H1047R | PIK3CA E545K | EGFR T790M | EGFR L858R | EGFR E746-A750 | KRAS G12C | KRAS G12R | KRAS G12S | KRAS G12D | KRAS G12A | KRAS G12V | KRAS G13D | BRAF V600E |
|---|---|---|---|---|---|---|---|---|---|---|---|---|---|---|---|---|
| 1 | 95.3 | | | | | | | | | | | | G12A (0.01%) | | | |
| 2 | 45.2 | | | | | | | | | | | | | | | |
| 3 | 41.1 | | | | E545K (100%) | | | | | | | | | | | |
| 4 | 87.4 | | | | | | | | | | | | | | | V600E (47%) |
| 5 | 89.6 | | | | | | | | | | | | | | | |
| 6 | 79.4 | | | H1047R (0.06%) | | | | | | | | | | | | |
| 7 | 59.3 | | | | | | | | | | | | | | | |
| 8 | 53 | | | | | | | | | | | | | | | |
| 9** | 52.4 | | | | | | | | | | G12S (0.3%) | | | G12V (2%) | G13D (0.3%) | |
| 10 | 155.5 | | | | | | | | | | | | | | | |
| 11 | 85.1 | | | | | | | | | | | | | | | |
| 12 | 68.7 | | | | E545K (100%) | | | | | | | | | | | |
| 13 | 108.5 | | | | | | | | G12C (100%) | | | | | | | |
| 14 | 62.2 | | | | | | | | | | | | | G12V (100%) | | |
| 15 | 72.2 | | | | | | | | | | | | | G12V (0.1%) | | |
| 16 | 47.6 | | | | | | | | | | | | | | | |
| 17 | 51.1 | | | | | | | | | | | | | | | |
| 18 | 44.8 | | | | | | | | G12C (100%) | | | | | | | |
| 19 | 71.3 | | | | | | | | | | | | | | | |
| 20 | 69 | | | | | | | | | | | | | | | |
| 21 | 34.6 | | | | | | | | G12C (2%) | | | | | | | |
| 22* | 32.5 | | | | | | | | | | | | | | | V600E (54%) |
| 23 | 9.4 | | | | | | | | | | | | | | | |
| 24 | 19.1 | | | | | | | | | | | | | | | |
| 25 | 38.7 | | E545D (0.2%) | | | | | | | | | | | | | |
| 26 | 29.6 | | | | | | | | | | | | | | | |
| 27 | 66.9 | | | | | | | | | | | | | | | |
| 28 | 72.7 | | | | | | | | | | | | | | | |
| 29 | 43.7 | | | | | | | | | | | | | | | |
| 30 | 100.7 | | | | | | | | | | | | | | | |
| 31 | 19.1 | | | | | | | | | | | | | | | V600E (34%) |
| 32 | 47.4 | | | | | | | | | | | | | | | |

Samples with mutations are underlined. Sample with more than one KRAS mutation is in italics. * indicates that the sample has KRAS and BRAF mutations. ** indicates that the sample has 4 KRAS mutations.

FIG. 43

Percent Mutation of Gastric Tumor Samples

| Sample ID | DNA con. ng/μl | Serial # | PIK3CA | | | | EGFR | | | KRAS | | | | | | | BRAF |
|---|---|---|---|---|---|---|---|---|---|---|---|---|---|---|---|---|---|
| | | | E542K | E545D | E545K | H1047R | T790M | L858R | E746 del | G12C | G12R | G12S | G12D | G12A | G12V | G13D | Q61H | V600E |
| 223 | 59.1 | 1 | - | - | - | - | T790M (0.2%) | - | - | - | - | - | - | - | - | - | - | - |
| 225 | 63.1 | 2 | - | - | - | - | - | - | - | - | - | - | - | - | - | - | - | - |
| 227 | 71.9 | 3 | - | - | - | - | - | - | - | - | - | - | - | - | - | - | - | - |
| 229 | 73 | 4 | - | - | - | - | - | - | - | - | - | - | - | - | - | - | - | - |
| 231 | 100.6 | 5 | - | - | - | - | - | - | - | - | - | - | - | - | - | - | - | - |
| 233** | 97.6 | 6 | - | - | - | - | - | - | - | - | G12R (0.001%) | - | - | - | G12V(2.3%) | G13D (low) | Q61H (0.5%) | - |
| 245 | 57.2 | 7 | - | - | - | - | - | - | - | - | - | - | - | - | - | - | - | - |
| 235 | 70.3 | 8 | - | - | - | - | - | - | - | - | - | - | - | - | - | - | - | - |
| 237 | 61.2 | 9 | - | - | - | - | - | - | - | - | - | - | - | - | - | - | - | - |
| 239 | 69.9 | 10 | - | - | - | - | - | - | - | - | - | - | - | - | - | - | - | - |
| 241 | 26.4 | 11 | - | - | - | - | - | - | - | G12C (low) | - | - | - | - | - | - | - | - |
| 243 | 38.3 | 12 | - | - | - | - | - | - | - | - | - | - | - | - | - | - | - | - |
| 247 | 65.8 | 13 | - | - | - | - | - | - | - | - | - | - | - | - | - | - | - | - |
| 249 | 34.8 | 14 | - | - | - | - | - | - | - | - | - | - | - | - | - | - | - | - |
| 251 | 37.7 | 15 | - | - | - | - | - | - | - | - | - | - | - | - | - | - | - | - |
| 253 | 43.3 | 16 | E545K (0.6%) | - | - | - | - | - | - | - | - | - | - | - | - | - | - | - |
| 255 | 54.1 | 17 | - | - | - | - | - | - | - | - | - | - | - | - | - | G13D (high/med) | - | - |

** indicates that the sample has 4 KRAS mutations.
Each assay was run with 40ng of sample DNA.

*FIG. 44*

Percent Mutation of Xenograft Samples

| Sample ID | Concentration ng/μl | PIK3CA | | | | EGFR | | | KRAS | | | | | | | | | BRAF |
|---|---|---|---|---|---|---|---|---|---|---|---|---|---|---|---|---|---|---|
| | | E542K | E545K | E545D | H1047R | T790M | L858R | E746 del | G12A | G12C | G12D | G12R | G12S | G12V | G13C | G13D | Q61H | V600E |
| 577 | 111.7 | | | | | | | | | | | | | | | | | V600E |
| 578 | 101 | | | | | | | | | | | | | | | | | |
| 579 | 158.1 | | | | | | | | | | | | | | | | | |
| 580 | 144.9 | | | | | | | | | | | | | | | | | |
| 581 | 191.4 | | | | H1047R (3.4%) | | | | | | | | | | | | | |
| 582 | 101.9 | | | | H1047R (1.2%) | | | | | | | | | | | | | |
| 583 | 114 | | | | H1047R (1%) | | | | | | | | | | | | | |
| 584 | 74.7 | | | | H1047R (1.8%) | | | | | | | | | | | | | |
| 585 | 72.6 | | | | | | | E746 del (100%) | | | | | | | | | | |
| 586 | 51.1 | | | | | | | E746 del (100%) | | | | | | | | | | |
| 587 | 58.2 | | | | | | | E746 del (100%) | | | | | | | | | | |
| 588 | 99.4 | | | | | | | E746 del (100%) | | | | | | | | | | |
| 589 | 86.6 | | | | | | | | | | | | | | | | | |
| 590 | 59 | | | | | | | | | | | | | | | | | |
| 591 | 70.4 | | | | | | | | | | | | | | | | | |
| 592 | 107.4 | | | | | | | | | | | | | | | | | |
| 593 | 123 | | | | | | | | | | | | | | | | | |
| 594 | 63.7 | | | | | | | | | | | | | | | | | |
| 595 | 125.7 | | | | | | | | | | | | | | | | | |

FIG. 45

Percent Mutation of Colorectal Cancer Samples

| Sample # | Cell Line/Tissue Type | KRAS | | | | | | | BRAF | PIK3CA | | | |
|---|---|---|---|---|---|---|---|---|---|---|---|---|---|
| | | G12S | G12D | G12A | G12V | G12R | G12C | G13D | V600E | H1047R | E542K | E545K | E545D |
| 94 | CRC | - | - | - | - | - | - | - | - | - | - | - | - |
| 95 | CRC | - | - | - | - | - | - | - | - | - | - | - | - |
| 96 | CRC | - | - | - | + | - | - | - | - | - | - | - | - |
| 97 | CRC | - | - | - | - | - | - | - | - | - | - | - | - |
| 98 | CRC | - | - | - | - | - | - | + | - | - | - | - | - |
| 99 | CRC | - | - | - | - | - | - | + | - | - | - | - | - |
| 100 | CRC | - | + | - | - | - | - | - | - | - | - | - | - |
| 101 | CRC | - | - | - | - | - | - | - | - | - | - | - | - |
| 102 | CRC | - | - | - | - | - | - | - | - | - | - | - | - |
| 103 | CRC | - | - | - | - | - | - | - | - | - | - | - | - |
| 104 | CRC | - | - | - | - | - | - | - | - | - | - | - | - |
| 105 | CRC | - | - | - | - | - | - | - | - | - | - | - | - |
| 106 | CRC | - | - | - | - | - | - | - | - | - | - | - | - |
| 107 | CRC | - | - | - | - | - | - | - | - | - | - | - | - |
| 108 | CRC | - | - | - | - | - | - | - | + | - | - | - | - |
| 109 | CRC | - | - | - | - | - | - | - | - | - | - | - | - |
| 110 | CRC | - | - | - | - | - | - | - | - | - | - | - | - |
| 111 | CRC | - | - | - | - | - | - | - | - | - | - | - | - |
| 112 | CRC | - | + | - | - | - | - | - | - | - | - | - | - |
| 113 | CRC | - | - | - | - | - | - | - | - | - | - | - | - |
| 114 | CRC | - | - | - | - | - | + | - | - | - | - | - | - |
| 115 | CRC | - | - | - | - | - | - | - | - | - | - | + | - |
| 116 | CRC | - | - | - | - | - | - | - | - | - | - | - | - |
| 117 | CRC | - | - | - | - | - | - | - | - | - | - | - | - |
| 118 | CRC | - | - | - | - | - | - | + | - | - | - | - | - |
| 119 | CRC | - | - | - | - | - | - | - | - | - | - | - | - |
| 120 | CRC | - | - | - | - | - | - | - | - | - | - | - | - |
| 121 | CRC | - | - | - | - | - | - | +(6%) | - | - | - | +(58%) | - |
| 122 | CRC | - | - | - | - | - | - | - | - | - | - | - | - |
| 123 | CRC | - | - | - | - | - | - | - | - | - | - | - | - |
| 124 | CRC | - | - | - | - | - | + | - | - | - | - | - | - |
| 125 | CRC | - | - | - | - | - | - | + | - | - | - | - | - |
| 126 | CRC | - | - | - | - | - | + | - | - | - | - | - | - |
| 127 | CRC | - | + | - | - | - | - | - | - | - | - | - | - |
| 128 | CRC | - | - | - | - | - | - | - | - | - | - | + | - |
| 129 | CRC | - | + | - | - | - | - | - | - | - | - | - | - |
| 130 | CRC | - | - | - | +(54%) | - | - | - | - | - | +(5%) | - | - |
| 131 | CRC | - | - | - | - | - | - | + | - | - | - | - | - |
| 132 | CRC | - | + | - | - | - | - | - | - | - | - | - | - |
| 133 | CRC | - | - | - | + | - | - | - | - | - | - | - | - |
| 134 | CRC | - | - | - | - | - | - | - | - | - | - | - | - |
| 135 | CRC | - | - | - | - | - | - | - | - | - | - | - | - |
| 136 | CRC | - | - | - | - | - | - | - | + | - | - | - | - |
| 137 | CRC | - | - | - | - | - | - | + | - | - | - | - | - |
| 138 | CRC | - | - | - | - | - | - | + | - | - | - | - | - |
| 139 | CRC | - | - | - | - | - | - | - | - | - | - | - | - |
| 140 | CRC | - | - | - | - | - | - | - | - | - | - | - | - |
| 141 | CRC | - | - | - | - | - | - | - | - | - | - | - | - |
| 142 | CRC | - | - | - | - | - | - | - | - | - | - | - | - |
| 143 | CRC | - | - | - | - | - | - | - | + | - | - | - | - |
| 144 | CRC | - | - | - | - | - | - | + | - | - | - | - | - |
| 145 | CRC | - | - | - | - | - | - | + | - | - | - | - | - |

*FIG. 46*

Percent Mutation of Colorectal Cancer Samples

| Sample # | Cell Line/Tissue Type | KRAS G12S | KRAS G12D | KRAS G12A | KRAS G12V | KRAS G12R | KRAS G12C | KRAS G13D | BRAF V600E | PIK3CA H1047R | PIK3CA E542K | PIK3CA E545K | PIK3CA E545D |
|---|---|---|---|---|---|---|---|---|---|---|---|---|---|
| 146 | CRC | - | - | - | - | - | + | - | - | - | - | - | - |
| 147 | CRC | - | +(100%) | - | - | - | - | - | - | +(100%) | - | - | - |
| 148 | CRC | - | - | - | - | - | + | - | - | - | - | - | - |
| 149 | CRC | - | - | - | - | - | - | +(24%) | - | +(0.1%) | - | - | - |
| 150 | CRC | - | - | - | - | - | - | - | - | - | - | + | - |
| 151 | CRC | - | - | - | - | - | - | - | - | - | - | - | - |
| 152 | CRC | - | + | - | - | - | - | - | - | - | - | - | - |
| 153 | CRC | - | - | - | - | - | - | - | - | - | - | - | - |
| 154 | CRC | - | - | - | - | - | - | + | - | - | - | - | - |
| 155 | CRC | - | + | - | - | - | - | - | - | - | - | - | - |
| 156 | CRC | - | - | - | - | - | - | - | - | - | - | + | - |
| 157 | CRC | - | - | - | - | - | - | - | - | - | - | - | - |
| 161 | CRC | - | - | - | + | - | - | - | - | - | - | - | - |
| 162 | CRC | - | - | - | - | - | - | - | - | - | - | - | - |
| 163 | CRC | - | +(34%) | - | - | - | - | - | - | - | +(3%) | - | - |
| 164 | CRC | - | - | - | - | - | - | - | - | - | - | - | - |
| 165 | CRC | - | - | - | - | - | - | - | - | - | - | - | - |
| 166 | CRC | - | - | - | - | - | - | - | - | - | - | - | - |
| 167 | CRC | - | - | - | - | - | - | - | - | - | - | - | - |
| 168 | CRC | - | - | - | - | - | - | - | - | - | - | - | - |
| 169 | CRC | - | - | - | - | - | - | - | - | - | - | - | - |
| 170 | CRC | - | - | - | - | - | - | - | - | - | - | - | - |
| 171 | CRC | - | - | - | - | - | - | - | - | - | - | - | - |
| 172 | CRC | - | - | - | - | - | - | - | - | - | - | - | - |
| 173 | CRC | - | - | - | - | - | - | - | - | - | - | - | - |
| 174 | CRC | - | - | - | - | - | - | - | - | - | - | - | - |
| 175 | CRC | - | - | - | - | - | - | - | - | - | - | - | - |
| 176 | CRC | - | - | - | - | - | - | + | - | - | - | - | - |
| 177 | CRC | - | - | - | - | - | - | - | - | - | - | - | - |
| 178 | CRC | - | - | - | - | - | - | - | - | - | - | - | - |
| 179 | CRC | - | + | - | - | - | - | - | - | - | - | - | - |
| 180 | CRC | - | - | - | - | - | - | + | - | - | - | - | - |
| 181 | CRC | - | - | - | - | - | + | - | - | - | - | - | - |
| 182 | CRC | - | - | - | - | - | - | - | - | - | - | - | - |
| 183 | CRC | - | + | - | - | - | - | - | - | - | - | - | - |
| 184 | CRC | - | - | - | - | - | - | - | - | - | - | - | - |
| 185 | CRC | - | - | - | - | - | - | - | - | - | - | - | - |
| 186 | CRC | - | - | - | - | - | - | - | - | - | - | - | - |
| 187 | CRC | - | - | + | - | - | - | - | - | - | - | - | - |
| 188 | CRC | - | - | - | - | - | - | - | - | - | - | - | - |
| 189 | CRC | - | + | - | - | - | - | - | - | - | - | - | - |
| 190 | CRC | - | - | - | - | - | - | + | - | - | - | - | - |
| 191 | CRC | - | + | - | - | - | - | - | - | - | - | - | - |
| 192 | CRC | - | - | - | - | - | - | - | - | - | - | - | - |
| 193 | CRC | - | - | - | - | - | - | - | - | - | - | - | - |
| 194 | CRC | - | - | - | - | - | - | - | - | - | - | - | - |
| 195 | CRC | - | - | - | - | - | - | - | - | - | - | - | - |
| 196 | CRC | - | - | - | - | - | - | + | - | - | - | - | - |

*FIG. 47*

Percent Mutation of Liver Tumor and Colon Tumor Samples

| Sample # | Tumor Tissue Type | KRAS | | | | | | | BRAF | PIK3CA | | | |
| --- | --- | --- | --- | --- | --- | --- | --- | --- | --- | --- | --- | --- | --- |
| | | G12S | G12D | G12A | G12V | G12R | G12C | G13D | V600E | H1047R | E542K | E545K | E545D |
| 197 | Liver/Colon Tumor | - | - | - | - | - | - | - | - | - | - | - | - |
| 198 | Liver/Colon Tumor | - | + | - | - | - | - | - | - | - | - | - | - |
| 199 | Liver/Colon Tumor | - | + | - | - | - | - | - | - | - | - | - | - |
| 200 | Liver/Colon Tumor | - | - | - | - | - | - | - | - | - | - | - | - |
| 201 | Liver/Colon Tumor | - | - | - | - | - | - | - | - | - | - | - | - |
| 202 | Liver/Colon Tumor | - | - | - | - | - | - | - | - | - | - | - | - |
| 203 | Liver/Colon Tumor | - | - | - | - | - | - | - | + | - | + | - | - |
| 204 | Liver/Colon Tumor | - | - | - | - | - | - | - | - | - | - | - | - |
| 205 | Liver/Colon Tumor | - | - | - | - | - | - | - | - | - | - | - | - |
| 206 | Liver/Colon Tumor | - | - | - | - | - | - | - | - | - | - | - | - |
| 207 | Liver/Colon Tumor | +(22%) | - | - | - | - | - | - | - | - | - | +(40%) | - |
| 208 | Liver/Colon Tumor | +(63%) | - | - | - | - | - | - | - | - | - | +(79%) | - |
| 209 | Liver/Colon Tumor | - | - | - | - | - | - | - | - | - | - | - | - |
| 210 | Liver/Colon Tumor | - | + | - | - | - | - | - | - | - | - | - | - |
| 211 | Liver/Colon Tumor | - | - | - | - | - | - | - | - | - | - | - | - |
| 212 | Liver/Colon Tumor | - | - | - | - | - | - | - | - | - | - | - | - |
| 213 | Liver/Colon Tumor | - | + | - | - | - | - | - | - | - | - | - | - |
| 214 | Liver/Colon Tumor | - | - | - | - | - | - | - | - | - | - | - | - |
| 215 | Liver/Colon Tumor | - | - | - | - | - | - | - | +(1%) | - | - | +(5%) | - |
| 216 | Liver/Colon Tumor | - | - | - | - | - | - | - | +(9%) | - | - | +(23%) | - |
| 217 | Liver/Colon Tumor | - | - | - | +(2%) | - | - | - | - | - | - | +(5%) | - |
| 218 | Liver/Colon Tumor | - | - | - | +(4%) | - | - | - | - | - | - | +(9%) | - |
| 219 | Liver/Colon Tumor | - | - | - | - | - | - | - | - | - | - | - | - |
| 220 | Liver/Colon Tumor | - | - | - | - | - | - | - | - | - | - | - | - |
| 221 | Liver/Colon Tumor | - | - | - | - | - | - | - | - | - | - | - | - |
| 222 | Liver/Colon Tumor | - | - | - | - | - | - | - | - | - | - | - | - |
| 223 | Liver/Colon Tumor | - | - | - | - | - | - | - | - | - | - | - | - |
| 224 | Liver/Colon Tumor | - | - | - | - | - | - | + | - | - | - | - | - |
| 225 | Liver/Colon Tumor | - | - | - | - | - | - | - | - | - | - | - | - |
| 226 | Liver/Colon Tumor | - | - | - | - | - | - | + | - | - | - | - | - |
| 227 | Liver/Colon Tumor | - | - | - | - | - | + | - | - | - | - | - | - |
| 228 | Liver/Colon Tumor | - | - | - | - | - | - | - | - | - | - | - | - |
| 229 | Liver/Colon Tumor | - | - | - | - | - | - | - | - | - | - | - | - |
| 230 | Liver/Colon Tumor | - | - | - | - | - | - | - | - | - | - | - | - |
| 231 | Liver/Colon Tumor | - | - | - | - | - | - | - | - | - | - | - | - |
| 232 | Liver/Colon Tumor | - | - | - | - | - | - | - | - | - | - | - | - |

*FIG. 48*

Percent Mutation of Pancreatic Cancer Samples

| DNA Conc. (ng/ul) | # | PIK3CA Mutations | | | | EGFR | | KRAS | | | | | | | BRAF |
|---|---|---|---|---|---|---|---|---|---|---|---|---|---|---|---|
| | | E542K | E545D | E545K | H1047R | T790M | L858R | G12C | G12R | G12S | G12D | G12A | G12V | G13D | V600E |
| 5.4 | 1 | - | - | - | - | - | - | - | - | - | - | - | - | - | - |
| 9.5 | 7 | - | - | - | - | - | - | - | - | - | - | - | - | - | - |
| 3.3 | 2 | - | - | - | - | - | - | - | - | - | 37.4 (1.1%) | - | - | - | - |
| 4.9 | 8 | - | - | - | - | - | - | - | - | - | 40.0 | - | - | - | - |
| 4.7 | 3 | - | - | - | - | - | - | - | - | - | - | - | - | - | - |
| 5.8 | 5 | - | - | - | - | - | - | - | - | - | - | - | - | - | - |
| 5.7 | 4 | - | - | - | - | - | - | - | - | - | - | - | 40.0 | - | - |
| 4.3 | 21 | - | - | - | - | - | - | - | - | - | - | - | 36.8 (0.2%) | - | - |
| 8.8 | 6 | - | - | - | - | - | - | - | - | - | 34.7 (29%) | - | - | - | - |
| 16.9 | 9 | - | - | - | - | - | - | - | - | - | 31.4 (100%) | - | - | - | - |
| 17.7 | 10 | - | - | - | - | - | - | - | - | - | - | - | - | - | - |
| 4.5 | 11 | - | - | - | - | - | - | - | - | - | 33.1 (100%) | - | - | - | - |
| 17.2 | 12 | - | - | - | - | - | - | - | - | - | 35.5 (7.4%) | - | - | - | - |
| 6.6 | 13 | - | - | - | - | - | - | - | - | - | - | - | - | - | - |
| 4.9 | 14 | - | - | - | - | - | - | - | - | - | - | - | - | - | - |
| 4.3 | 17 | - | - | - | - | - | - | - | - | - | - | - | - | - | - |
| 4.1 | 15 | - | - | - | - | - | - | - | - | - | - | - | - | - | - |
| 5.2 | 16 | - | - | - | - | - | - | - | - | - | - | - | - | - | - |
| 5 | 18 | - | - | - | - | - | - | - | - | - | - | - | - | - | - |
| 6.9 | 35 | - | - | - | - | - | - | - | - | - | - | - | 32.2 (3%) | - | - |
| 5.2 | 19 | - | - | - | - | - | - | - | - | - | - | - | 28.9 (63%) | - | - |
| 7.7 | 20 | - | - | - | - | - | - | - | - | - | - | - | - | - | - |
| 6.6 | 36 | - | - | - | - | - | - | - | - | - | - | - | - | - | - |
| 4 | 22 | - | - | - | - | - | - | - | - | - | - | - | - | - | - |
| 2 | 23 | - | - | - | - | - | - | - | - | - | 35.4 (5%) | - | - | - | - |
| 10.2 | 24 | - | - | - | - | - | - | - | - | - | 35.3 (5%) | - | - | - | - |
| 8.2 | 25 | - | - | - | - | - | - | - | - | - | - | - | - | - | - |
| 13.3 | 26 | - | - | - | - | - | - | - | - | - | - | - | 31 (4%) | - | - |
| 4.4 | 27 | - | - | - | - | - | - | - | - | - | - | - | 35 (1%) | - | - |
| 5.3 | 45 | - | - | - | - | - | - | 40.0 | - | - | - | - | - | - | - |
| 8 | 28 | - | - | - | - | - | - | 35 (NA) | - | - | - | - | - | - | - |
| 5.3 | 29 | - | - | - | - | - | - | - | - | - | - | - | - | - | - |
| 6.4 | 30 | - | - | - | - | - | - | - | - | - | - | - | - | - | - |
| 6.3 | 31 | - | - | - | - | - | - | - | - | - | - | - | - | - | - |
| 6.6 | 32 | - | - | - | - | - | - | - | - | - | - | - | - | - | - |
| 7 | 33 | - | - | - | - | - | - | - | - | - | - | - | - | - | - |
| 6.5 | 34 | - | - | - | - | - | - | - | - | - | - | - | - | - | - |
| 14.6 | 37 | - | - | - | - | - | - | - | - | - | 33.9 (32%) | - | - | - | - |
| 6 | 38 | - | - | - | - | - | - | - | - | - | 40.0 | - | - | - | - |
| 6.4 | 39 | - | - | - | - | - | - | - | - | - | 35.3 (5.4%) | - | - | - | - |
| 5.1 | 40 | - | - | - | - | - | - | - | - | - | 37.7 (0.9%) | - | - | - | - |
| 5 | 41 | - | - | - | - | - | - | - | - | - | - | - | - | - | - |
| 5 | 42 | - | - | - | - | - | - | - | - | - | - | - | - | - | - |
| 4.9 | 43 | - | - | - | - | - | - | - | - | - | - | - | - | - | - |
| 5.7 | 44 | - | - | - | - | - | - | - | - | - | - | - | - | - | - |

*FIG. 49*

COMPOSITIONS AND METHODS FOR DETECTING ALLELIC VARIANTS

CROSS-REFERENCES TO RELATED APPLICATIONS

The present application is a continuation of PCT/US2012/051442, filed Aug. 17, 2012, which application claims priority to U.S. Provisional Application No. 61/525,137, filed Aug. 18, 2011, and U.S. Provisional Application No. 61/588,151, filed Jan. 18, 2012, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -226-2.TXT, created on Mar. 24, 2014, 8,192 bytes, machine format IBM-PC, MS-Windows operating system, is hereby incorporated by reference in its entirety for all purposes.

BACKGROUND OF THE INVENTION

Single nucleotide polymorphisms (SNPs) are the most common type of genetic diversity in the human genome, occurring at a frequency of about one SNP in 1,000 nucleotides or less in human genomic DNA (Kwok, *Ann. Rev. Genom. Hum. Genet.*, 2:235-258 (2001)). SNPs have been implicated in genetic disorders, susceptibility to different diseases, predisposition to adverse reactions to drugs, and for use in forensic investigations. Thus, SNP (or rare mutation) detection provides great potentials in diagnosing early phase diseases, such as detecting circulating tumor cells in blood, for prenatal diagnostics, as well as for detection of disease-associated mutations in a mixed cell population.

Numerous approaches for SNP genotyping have been developed based on methods involving hybridization, ligation, or DNA polymerases (Chen et al., *Pharmacogenomics J.*, 3:77-96 (2003)). For example, allele-specific polymerase chain reaction (AS-PCR) is a widely used strategy for detecting DNA sequence variation (Wu et al., *Proc. Natl. Acad. Sci. USA*, 86:2757-2760 (1989)). AS-PCR, as its name implies, is a PCR-based method whereby one or both primers are designed to anneal at sites of sequence variations which allows for the ability to differentiate among different alleles of the same gene. AS-PCR exploits the fidelity of DNA polymerases, which extend primers with a mismatched 3' base at much lower efficiency, from 100 to 100,000 fold less efficient, than that with a matched 3' base (Chen et al., *Pharmacogenomics J.*, 3:77-96 (2003)). The difficulty in extending mismatched primers results in diminished PCR amplification that can be readily detected.

The specificity and selectivity of AS-PCR, however, is largely dependent on the nature of exponential amplification of PCR which makes the decay of allele discriminating power rapid. Even though primers are designed to match a specific variant to selectively amplify only that variant, in actuality significant mismatched amplification often occurs. Moreover, the ability of AS-PCR to differentiate between allelic variants can be influenced by the type of mutation or the sequence surrounding the mutation or SNP (Ayyadevara et al., *Anal. Biochem.*, 284:11-18 (2000)), the amount of allelic variants present in the sample, as well as the ratio between alternative alleles. Collectively, these factors are often responsible for the frequent appearance of false-positive results, leading many researchers to attempt to increase the reliability of AS-PCR (Orou et al., *Hum. Mut.*, 6:163-169 (1995); Imyanitov et al., *Biotechniques*, 33:484-490 (2002); McKinzie et al., *Mut. Res.*, 517:209-220 (2002); Latorra et a, *Hum. Mut.*, 22:79-85 (2003)).

Another technology involving probe hybridization methods used for discriminating allelic variations is TaqMan® genotyping. However, like AS-PCR, selectivity using this method is limited and not suitable for detecting rare (1 in ≥1,000) alleles or mutations in a mixed sample.

As such, there is a need in the art for improved compositions and methods to detect single point substitutions (e.g., SNPs), insertions, or deletions against a background of wild-type allele in thousand-fold or greater excess with increased sensitivity and specificity. The present invention satisfies this need and provides related advantages as well.

SUMMARY OF THE INVENTION

The present invention provides compositions, methods, and kits for discriminating sequence variation between different alleles. More specifically, in some embodiments, the present invention provides compositions, methods, and kits for determining the presence and/or level (e.g., quantitating) of rare (e.g., mutant) allelic variants, such as single nucleotide polymorphisms (SNPs) or nucleotide insertions or deletions, in samples comprising abundant (e.g., wild-type) allelic variants with high sensitivity and/or specificity. As such, in certain embodiments, the present invention provides a highly selective method for the detection of somatic mutations, e.g., in samples containing abundant levels of a wild-type allele compared to very low levels of a mutant allele.

In one aspect, the present invention provides compositions for use in identifying and/or quantitating allelic variants in nucleic acid samples. In certain embodiments, the compositions of the invention can comprise one, two, three or more of the following: (a) an allele-specific primer; (b) an allele-specific blocker probe; (c) a detector probe; and/or (d) a locus-specific primer.

In some embodiments, the allele-specific primer comprises a target-specific portion and an allele-specific nucleotide portion. In some embodiments, the allele-specific primer may further comprise a tail. In some exemplary embodiments, the tail is located at the 5' end of the allele-specific primer. In other embodiments, the tail of the allele-specific primer has repeated guanine and cytosine residues ("GC-rich"). In some embodiments, the melting temperature ("Tm") of the entire allele-specific primer ranges from about 50° C. to about 67° C. In some embodiments, the allele-specific primer concentration is between about 20-900 nM.

In some embodiments, the allele-specific nucleotide portion of the allele-specific primer is located at the 3' terminus. As a non-limiting example, "T" is used as the 3' allele-specific nucleotide portion of the allele-specific primer when detecting and/or quantifying a polymorphic site in which "A" is the mutant allele. As another non-limiting example, "C" is used as the 3' allele-specific nucleotide portion of the allele-specific primer when detecting and/or quantifying a polymorphic site in which "G" is the mutant allele.

In some embodiments, the allele-specific blocker probe comprises a non-extendable blocker moiety at the 3' terminus. The blocker moiety can comprise any modification of the ribose ring 3'-OH of the oligonucleotide which prevents addition of further bases to the 3'-end of the oligonucleotide sequence by a polymerase. In some exemplary embodiments, the non-extendable blocker moiety includes, without limitation, an optionally substituted $C_1$-$C_{24}$ alkyl diol (e.g., a 3'-hexanediol modification), an optionally substituted $C_2$-$C_{24}$ alkenyl diol, an optionally substituted $C_2$-$C_{24}$ alkynyl diol, a minor groove binder (MGB), an amine ($NH_2$), biotin, PEG, $PO_4$, and combinations thereof. In preferred embodiments, the non-extendable blocker moiety comprises an optionally substituted $C_1$-$C_{24}$ alkyl diol (e.g., a 3'-hexanediol modification). In certain instances, the allele-specific nucleotide portion of the allele-specific blocker probe is located from about 5 to about 15 or from about 5 to about 10, such as about 5, 6, 7, 8, 9, 10, 11, 12, 13, 14, or 15 nucleotides away from the blocker moiety of the allele-specific blocker probe. In certain other instances, the allele-specific blocker probe is not cleaved during PCR amplification. In further instances, the Tm of the allele-specific blocker probe ranges from about 58° C. to about 66° C.

In certain embodiments, the non-extendable blocker moiety does not comprise or include a minor groove binder (MGB). In certain other embodiments, the non-extendable blocker moiety does not comprise or include a $PO_4$ group. In further embodiments, the non-extendable blocker moiety consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In some embodiments, the allele-specific blocker probe and/or allele-specific primer comprises at least 1, 2, 3, 4, 5, or 6 (e.g., non-consecutive) base, sugar, and/or backbone modifications. In certain instances, the modification(s) may increase the difference in the Tm between matched and mismatched target sequences and/or decrease mismatch priming efficiency, thereby improving assay specificity and/or selectivity. Non-limiting examples of such modifications include locked nucleic acid (LNA), peptide nucleic acid (PNA), threose nucleic acid (TNA), zip nucleic acid (ZNA), triazole nucleic acid, 5' methyl-deoxycytidine, 2'-fluoro, 8-aza-7-deaza-dA (ppA), 8-aza-7-deaza-dG (ppG), 2'-deoxypseudoisocytidine (iso dC), 5-fluoro-2'-deoxyuridine (fdU), and 2'-O,4'-C-ethylene bridged nucleic acid (ENA) modifications, and combinations of these modifications. In preferred embodiments, the modification present on the allele-specific blocker probe and/or allele-specific primer comprises one or more LNA modifications. In certain embodiments, the modification is located (a) at the 3'-end, (b) at the 5'-end, (c) at an internal position, or at any combination of (a), (b) or (c) within the allele-specific blocker probe and/or the allele-specific primer. In some preferred embodiments, the modification (e.g., LNA) is located at the allele-specific nucleotide portion of the allele-specific primer, such that the nucleoside of the modified residue comprises the nucleobase used to discriminate between allelic variants. In other preferred embodiments, the modification (e.g., LNA) is located at the allele-specific nucleotide portion of the allele-specific blocker probe, such that the nucleoside of the modified residue comprises the nucleobase used to discriminate between allelic variants.

In some embodiments, the detector probe comprises a sequence-based or locus-specific detector probe. In other embodiments, the detector probe comprises a 5' nuclease probe. In some exemplary embodiments, the detector probe comprises an MGB moiety, a reporter moiety (e.g., FAM™, TET™, JOE™, VIC™, or SYBR® Green), a quencher moiety (e.g., Black Hole Quencher™ or TAMRA™), and/or a passive reference (e.g., ROX™). In some embodiments, the detector probe is designed according to the methods and principles described in U.S. Pat. No. 6,727,356, the disclosure of which is incorporated herein by reference in its entirety. In particular embodiments, the detector probe comprises a TaqMan® probe (Applied Biosystems, Foster City, Calif.).

In some embodiments, the compositions of the invention can further comprise a polymerase; deoxyribonucleotide triphosphates (dNTPs); other reagents and/or buffers suitable for amplification; and/or a template sequence or nucleic acid sample. In some embodiments, the polymerase can be a DNA polymerase. In some other embodiments, the polymerase can be thermostable, such as Taq DNA polymerase. In other embodiments, the template sequence or nucleic acid sample can be DNA, such as genomic DNA (gDNA) or complementary DNA (cDNA). In other embodiments, the template sequence or nucleic acid sample can be RNA, such as messenger RNA (mRNA).

In another aspect, the present invention provides methods for amplifying an allele-specific sequence. Some of these methods can include one or more of the following: (a) hybridizing an allele-specific primer to a first nucleic acid molecule comprising a first allele (allele-1); (b) hybridizing an allele-specific blocker probe to a second nucleic acid molecule comprising a second allele (allele-2), wherein allele-2 corresponds to the same loci as allele-1; (c) hybridizing a detector probe to the first nucleic acid molecule; (d) hybridizing a locus-specific primer to the extension product of the allele-specific primer; and (e) PCR amplifying the first nucleic acid molecule comprising allele-1.

In yet another aspect, the present invention provides methods for detecting and/or quantitating an allelic variant in a pooled or mixed sample comprising other alleles. Some of these methods can include one or more of the following: (a) hybridizing a first allele-specific primer to a first nucleic acid molecule comprising a first allele (allele-1) in a first reaction mixture and hybridizing a second allele-specific primer to a first nucleic acid molecule comprising a second allele (allele-2) in a second reaction mixture, wherein allele-2 corresponds to the same locus as allele-1; (b) hybridizing a first allele-specific blocker probe to a second nucleic acid molecule comprising allele-2 in the first reaction mixture and hybridizing a second allele-specific blocker probe to a second nucleic acid molecule comprising allele-1 in the second reaction mixture; (c) hybridizing a first detector probe to the first nucleic acid molecule in the first reaction mixture and hybridizing a second detector probe to the first nucleic acid molecule in the second reaction mixture; (d) hybridizing a first locus-specific primer to the extension product of the first allele-specific primer in the first reaction mixture and hybridizing a second locus-specific primer to the extension product of the second allele-specific primer in the second reaction mixture; (e) PCR amplifying the first nucleic acid molecule to form a first set or sample of amplicons and PCR amplifying the second nucleic acid molecule to form a second set or sample of amplicons; and (f) comparing the first set of amplicons to the second set of amplicons to quantitate allele-1 in the sample comprising allele-2 and/or allele-2 in the sample comprising allele-1.

In some embodiments, the first and/or second allele-specific primer comprises a target-specific portion and an allele-specific nucleotide portion. In some embodiments, the first and/or second allele-specific primer may further comprise a tail. In some embodiments, the Tm of the entire first and/or second allele-specific primer ranges from about 50° C. to about 67° C. In some instances, the concentration of the first and/or second allele-specific primer is between about 20-900 nM.

In some embodiments, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments, the tail is located at the 5'-end of the first and/or second allele-specific primer. In some embodiments, the 5' tail of the first allele-specific primer and the 5' tail of the second allele-specific primer comprise the same sequence. In other embodiments, the 5' tail of the first allele-specific primer and the 5' tail of the second allele-specific primer are the same sequence. In other embodiments, the tail of the first and/or second allele-specific primer is GC-rich.

In some embodiments, the allele-specific nucleotide portion of the first allele-specific primer is specific to a first allele (allele-1) of a SNP and the allele-specific nucleotide portion of the second allele-specific primer is specific to a second allele (allele-2) of the same SNP. In some embodiments, the allele-specific nucleotide portion of the first and/or second allele-specific primer is located at the 3'-terminus. In some embodiments, the selection of the allele-specific nucleotide portion of the first and/or second allele-specific primer involves the use of a highly discriminating base.

In certain other embodiments, the first and/or second allele-specific blocker probe independently comprises a non-extendable blocker moiety at the 3' terminus. The blocker moiety can comprise any modification of the ribose ring 3'-OH of the oligonucleotide which prevents addition of further bases to the 3'-end of the oligonucleotide sequence by a polymerase. In exemplary embodiments, the non-extendable blocker moiety includes, without limitation, an optionally substituted $C_1$-$C_{24}$ alkyl diol (e.g., a 3'-hexanediol modification), an optionally substituted $C_2$-$C_{24}$ alkenyl diol, an optionally substituted $C_2$-$C_{24}$ alkynyl diol, a minor groove binder (MGB), an amine (MGB), biotin, PEG, $PO_4$, and combinations thereof. In preferred embodiments, the non-extendable blocker moiety comprises an optionally substituted $C_1$-$C_{24}$ alkyl diol (e.g., a 3'-hexanediol modification). In certain instances, the allele-specific nucleotide portion of the first and/or second allele-specific blocker probe is located from about 5 to about 15 or from about 5 to about 10, such as about 5, 6, 7, 8, 9, 10, 11, 12, 13, 14, or 15 nucleotides away from the blocker moiety of the first and/or second allele-specific blocker probe. In certain other instances, the first and/or second allele-specific blocker probe is not cleaved during PCR amplification. In further instances, the Tm of the first and/or second allele-specific blocker probe ranges from about 58° C. to about 66° C.

In certain embodiments, the non-extendable blocker moiety in the first and/or second allele-specific blocker probe does not comprise or include a minor groove binder (MGB) and/or a $PO_4$ group. In certain other embodiments, the non-extendable blocker moiety in the first and/or second allele-specific blocker probe consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In some embodiments, the first and/or second allele-specific blocker probe and/or the first and/or second allele-specific primer comprises at least one nucleic acid modification. In some embodiments, the modification(s) may increase the difference in the Tm between matched and mismatched target sequences and/or decrease mismatch priming efficiency, thereby improving assay specificity and/or selectivity. Examples of such modification(s) include, without limitation, the modified bases, nucleic acid analogs, and ribose-modified nucleic acids described herein such as locked nucleic acids (LNA), peptide nucleic acids (PNA), threose nucleic acids (TNA), zip nucleic acids (ZNA), and triazole nucleic acids (TzNA). In particular embodiments, one or more (e.g., 2 to 6, or 2, 3, 4, 5, or 6) nucleic acid modifications such as LNAs are present on the allele-specific blocker probe and/or allele-specific primer. In preferred embodiments, the plurality of modifications on the probe or primer is non-consecutive or non-contiguous, e.g., two modifications such as LNAs are not next to each other in the probe or primer sequence. In certain embodiments, the nucleic acid modification(s) is located (a) at the 3'-end, (b) at the 5'-end, (c) at an internal position, or at any combination of (a), (b) or (c) within the first and/or second allele-specific blocker probe and/or the first and/or second allele-specific primer. In some preferred embodiments, one modification (e.g., LNA) is located at the allele-specific nucleotide portion of the first and/or second allele-specific primer, such that this modification comprises the nucleobase used to discriminate between allelic variants. In other preferred embodiments, one modification (e.g., LNA) is located at the allele-specific nucleotide portion of the first and/or second allele-specific blocker probe, such that this modification comprises the nucleobase that is used to discriminate between allelic variants.

In some embodiments, the specificity of allelic discrimination is improved by the inclusion of a nucleic acid modification in the first and/or second allele-specific primer and/or first and/or second allele-specific blocker probe as compared to the use of a non-modified allelic-specific primer or blocker probe. In some embodiments, the improvement in specificity is at least about 2 fold (e.g., at least about 2 fold, 3 fold, 4 fold, 5 fold, 10 fold, 15 fold, 20 fold, etc.).

In other embodiments, the specificity of allelic discrimination is at least about 2 fold (e.g., at least about 2 fold, 3 fold, 4 fold, 5 fold, 10 fold, 15 fold, 20 fold, etc.) better than the specificity of allelic discrimination using Allele-Specific PCR with a Blocking reagent (ASB-PCR) methods described in Morlan et al., *PloS ONE*, 4:e4584 (2009).

In some embodiments, the methods further comprise a 2-stage cycling protocol. In some embodiments, the number of cycles in the first stage of the 2-stage cycling protocol comprises fewer cycles than the number of cycles used in the second stage. In other embodiments, the number of cycles in the first stage is about 90% fewer cycles than the number of cycles in the second stage. In yet other embodiments, the number of cycles in the first stage is between 3-7 cycles and the number of cycles in the second stage is between 42-48 cycles.

In some embodiments, the annealing/extension temperature used during the first cycling stage of the 2-stage cycling protocol is between about 1-3° C. lower than the annealing/extension temperature used during the second stage. In certain embodiments, the annealing/extension temperature used during the first cycling stage of the 2-stage cycling protocol is between 56-59° C. and the annealing/extension temperature used during the second stage is between 60-62° C.

In some embodiments, the methods further comprise a pre-amplification step. In certain embodiments, the pre-amplification step comprises a multiplex amplification reaction that uses at least two complete sets of allele-specific primers and locus-specific primers, wherein each set is suitable or operative for amplifying a specific polynucleotide of interest. In other embodiments, the products of the multiplex amplification reaction are divided into secondary single-plex amplification reactions, wherein each single-plex reaction contains at least one primer set previously used in the multiplex reaction. In yet other embodiments, the multiplex amplification reaction further comprises a plurality of allele-specific blocker probes. In some embodiments, the multiplex amplification reaction is carried out for a number of cycles suitable to keep the reaction within the linear phase of amplification.

In some embodiments, the first and/or second detector probes are the same. In some embodiments, the first and/or second detector probes are different. In some embodiments, the first and/or second detector probe is a sequence-based or locus-specific detector probe. In other embodiments the first and/or second detector probe is a 5' nuclease probe. In some exemplary embodiments, the first and/or second detector probes comprises an MGB moiety, a reporter moiety (e.g., FAM™, TET™, JOE™, VIC™, or SYBR® Green), a quencher moiety (e.g., Black Hole Quencher™ or TAMRA™), and/or a passive reference (e.g., ROX™). In some embodiments, the first and/or second detector probe is designed according to the methods and principles described in U.S. Pat. No. 6,727,356, the disclosure of which is incorporated herein by reference in its entirety. In particular embodiments, the first and/or second detector probe comprises a TaqMan® probe (Applied Biosystems, Foster City, Calif.).

In some embodiments, the first locus-specific primer and the second locus-specific primer comprise the same sequence. In some embodiments, the first locus-specific primer and the second locus-specific primer are the same sequence.

In some embodiments, the first and/or second reaction mixtures can further comprise a polymerase; dNTPs; other reagents and/or buffers suitable for PCR amplification; and/or a template sequence or nucleic acid sample. In some embodiments, the polymerase can be a DNA polymerase. In some embodiments, the polymerase can be thermostable, such as Taq DNA polymerase. In some embodiments, the template sequence or nucleic acid sample can be DNA, such as gDNA or cDNA. In other embodiments the template sequence or nucleic acid sample can be RNA, such as mRNA.

In some embodiments, the first allele-specific blocker probe binds to the same strand or sequence as the second allele-specific primer, while the second allele-specific blocker probe binds to the same strand or sequence as the first allele-specific primer. In some embodiments, the first and/or second allele-specific blocker probes are used to reduce the amount of background signal generated from either the second allele and/or the first allele, respectively. In some embodiments, first and/or second allele-specific blocker probes are non-extendable and preferentially anneal to either the second allele or the first allele, respectively, thereby blocking the annealing of, for example, the extendable first allele-specific primer to the second allele and/or the extendable second allele-specific primer to first allele.

In some exemplary embodiments, the first allele is a rare (e.g., minor) or mutant allele. In other exemplary embodiments, the second allele is an abundant (e.g., major) or wild-type allele.

In another aspect, the present invention provides kits for detecting or quantitating a first allelic variant in a sample comprising a second allelic variant comprising one or more of the following: (a) a first allele-specific primer; (b) a second allele-specific primer; (c), a first locus-specific primer; (d) a second locus-specific primer; (e) a first allele-specific blocker probe; (f) a second allele-specific blocker probe; (g) a first locus-specific detector probe; and (h) a second locus-specific detector probe.

In some embodiments, the first and/or second allele-specific primer comprises a target-specific portion and an allele-specific nucleotide portion. In some embodiments, the first and/or second allele-specific primer may further comprise a tail. Other embodiments with respect to the first and/or second allele-specific primers in the kits of the invention are described above.

In some embodiments, the compositions, methods and kits of the present invention provide high allelic discrimination specificity and selectivity. In some embodiments, the quantitative determination of specificity and/or selectivity comprises a comparison of Ct values between a first set of amplicons and a second set of amplicons. In some embodiments, selectivity is at a level whereby a single copy of a given allele in about 1 million copies of another allele or alleles can be detected.

In particular embodiments, the compositions, methods, and kits of the invention provide improved detection and discrimination of allelic variants using one, two, three or more of the following components: (a) an allele-specific primer comprising a nucleic acid modification such as a locked nucleic acid (LNA) at the position of the discriminating base (e.g., an allele-specific primer containing a 3'-end LNA at the polymorphic site); (b) an allele-specific blocker probe comprising a non-extendable blocker moiety such as a $C_1$-$C_{24}$ alkyl diol (e.g., hexanediol) modification at the 3' terminus and a nucleic acid modification such as a locked nucleic acid (LNA) at the position of the discriminating base (e.g., a blocker oligonucleotide containing a hexanediol chemical group at the 3'-end and a single LNA at the polymorphic site at a position that is about 5-15 (e.g., about 10) nucleotides away from the blocking moiety, e.g., in the middle of the blocker probe); (c) a detector probe such as a TaqMan® probe (e.g., a TaqMan® MGB FAM probe); and (d) a locus-specific primer such as a reverse primer. In certain instances, the blocker moiety comprises a $C_1$-$C_{24}$ alkyl diol (e.g., hexanediol) that is conjugated to the 3'-end of the allele-specific blocker oligonucleotide sequence via a phosphoramidite linkage. In certain other instances, the assay methods of the invention are performed on an ABI 7900HT Real Time PCR Instrument, although any type of real time PCR instrument known to one of ordinary skill in the art can be used. In particular embodiments, the reaction characteristics comprise the following: Stage 1: 95.0° C. for 10:00 min; Stage 2: Repeats: 40 95.0° C. for 0:20 min 60.0° C. for 0:45 min.

Other objects, features, and advantages of the present invention will be apparent to one of skill in the art from the following detailed description and figures.

BRIEF DESCRIPTION OF THE DRAWINGS

FIG. 11 illustrates that the Inostics BEAMing assay made the incorrect call and identified 14 out of 15 mutant samples as wild-type samples.

FIG. 12 illustrates that the somatic mutation genotyping assay of the invention had a detectable signal as low as 50 to 100 positive cells in the whole blood mixture.

FIG. 15 shows that strategically placed LNA modifications on an allele-specific primer can improve amplification and lower the Ct value. The performance of the assay can be improved by the used of more than one LNA.

FIG. 17 shows an exemplary LNA molecule and other modified LNAs that can be used in the present invention. The allele-specific primer of the present invention can comprise 2 to 6 LNAs.

FIG. 21 shows an exemplary TzDNA molecule (left) and an exemplary allele-specific primer with a TzDNA modification (right; T in FIG. 21).

FIG. 23 illustrates that the KRAS G12A assay comprising a LNA primer and a blocker probe with hexanediol specifically amplified the allelic variant (A) and inhibited amplification of the wild-type allele (G). The selectivity of the assay is improved with the use of a blocker in combination with the presence of LNA on the allele-specific primer.

FIG. 25 shows that a blocker probe with LNA modification has a lower Ct value compared to one without LNA. FIG. 25 also illustrates that the method of the present invention that employs a blocker probe with LNA efficiently and selectively amplified the mutant variant, and shows excellent allelic discrimination.

FIG. 26 also shows that the wild-type allele was not amplified.

FIG. 27 shows the difference in melting temperature (Tm) and Ct value between two blocker probes with the same sequence and 3' hexanediol modification, but different locations of LNA on the blocker sequence (SEQ ID NOS:10 and 11). This illustrates how the position of the LNA in the blocker sequence influences the performance of the assay. LNA placed at the base of the allelic variance improves the performance of the assay with the lower Ct, compared to the blocker with LNA placed away from the allelic variant nucleotide.

FIG. 30 shows that the ΔCt values can be used to determine the feasibility of the assay and its selectivity. The higher ΔCt value obtained with the LNA-containing primers and probes indicate the feasibility and selectivity of the assay of the present invention.

FIG. 31 shows how the AΔCt values are calculated from the Ct values from various somatic mutation genotyping assays. Assay A of the figure that was designed with an LNA-containing primer and blocker performed better than the other assays that contained primers and probes with consecutive LNAs.

FIGS. 32A-C illustrate the use of the PIK3CA E545K assay of the present invention to quantify the percentage of the mutant variant present in an unknown sample. FIG. 32A shows that the standard curve for the PIK3CA E545K allelic variant and the MCF 7 cell line. It was created using methods described herein. FIG. 32B shows amplification curves for two unknown samples from patients with colorectal cancer (Samples A and B) and the positive control (MCF 7 cell line) generated using the genotyping assay. FIG. 32C shows the amount and the percentage (percent mutation) of the mutant variant E545K present in the samples as determined by the calculator.

FIG. 33A shows the amplification plot and the standard curve for the KRAS G12D genotyping assay and the LS 174T cell line. FIG. 33B shows that amplification plots for two unknown samples from patients with pancreatic cancer (Samples A and B) and a positive control (LS 174T cell line) that were generated using methods of the present invention. FIG. 33C shows the amount of DNA in Sample A expressing the mutant variant was determined using the calculator to be 3.25 ng or 9.6%, relative to the positive control.

FIGS. 34A-C illustrate the use of the EGFR E746-A750 deletion EGF assay of the present invention to quantify the percentage of the mutant variant present in an unknown sample. FIG. 34A shows the amplification plot and standard curve for the E746-A750 deletion of the EGFR gene for the H1650 cell line. FIG. 34B shows that the amplification plot for an unknown sample (Sample A) from a patient with lung cancer and a positive control (H1650 cell line) that were generated using methods of the present invention. FIG. 34C shows the amount of DNA in Sample A expressing the EGFR deletion variant was determined using the calculator to be 3.25 ng or 9.6%, relative to the positive control.

FIG. 35A shows the amplification plot and standard curve for the BRAF V600E allelic variant for the HT 29 cell line. FIG. 35B shows that the amplification plot for an unknown sample (Sample A) from a patient with lung cancer and a positive control (H1650 cell line) that were generated using methods of the present invention. FIG. 35C shows the amount of DNA in Sample A expressing the V600E variant of BRAF was calculated to be 0.18 ng or 1.2%, relative to the positive control.

FIG. 36A shows a section that has a high percentage of tumor cells (the white arrow indicates tumor cells). FIG. 36B shows a section composed of a mixture of tumor cells (white arrow), stroma with blood vessels (black arrow), inflammatory cells (e.g., lymphocytes; red arrow); and a lung alveolus filled with macrophages (green arrow).

FIGS. 37A-B illustrate the relationship between cytokeratin (CK) levels and the expression of allelic variants in either gastric tumor samples or pancreatic tumor samples. FIG. 37A illustrates that in gastric tumor samples #1, 2 and 4 there was a high level of CK and a low percent mutation for the EGFR T790M, KRAS G12V, KRAS Q61H, or PIK3CA E545K allelic variant. These results show that in sample #1, 2 and 4 few of the tumor cells are likely to carry the EGFR T790M, KRAS G12V, KRAS Q61H, or PIK3CA E545K SNPs. Yet, in sample #5 there was a high level of CK and a high percent mutation (e.g., 90%) for the KRAS G12D mutation. This result shows that most of the tumor cells in sample #5 are likely to carry the G13D mutation. FIG. 37B shows that in pancreatic tumor sample #1 there was a high level of CK and a high percent mutation (100%) for the KRAS G12D variant, thus indicating that most of the tumor cells are likely to carry the mutant allele. In contrast, in pancreatic tumor sample #3 there was a high level of CK but a low percent mutation (e.g., 5%) for the KRAS G12D SNP. Few tumor cells of sample #3 are likely to carry the G12D mutation.

FIGS. 38A-C illustrate the sensitivity of the somatic mutation genotyping assay of the present invention (e.g., KRAS G12A assay) compared to Life Technologies' cast-PCR™ Mutation Assay. FIG. 38A illustrates the amplification curves for the genotyping assays of the present invention. FIG. 38B illustrates the amplification curves for Life Technologies' castPCR™ Mutation Assays performed on the same test samples. FIG. 38C shows that assay of the present invention detected the G12A mutation when the test sample contained as few as 250 positive tumor cells. By comparison, a larger number of tumor cells were needed to detect the mutation using Life Technologies' castPCR™ Mutation Assay.

FIGS. 39A-C illustrate the sensitivity of the somatic mutation genotyping assay of the present invention (e.g., KRAS G12A assay) compared to Life Technologies' cast-PCR™ Mutation Assay. FIG. 39A shows the amplification curves of the test samples using the genotyping assay of the present invention. FIG. 39B shows the amplification curves for Life Technologies' castPCR™ Assay. FIG. 39C shows that assay of the present invention detected the G12S KRAS allelic variant in as few as 100 positive tumor cells, while Life Technologies' castPCR™ Mutation Assay could not.

FIG. 40 shows the results obtained by using the methods of the present invention to detect (e.g., presence or absence) and/or quantitate (e.g., percent mutation) the following SNPs in breast cancer samples: PIK3CA E542K, E545D, E545K, H1047R; EGFR T790M, L858R; KRAS G12A, G12C, G12D, G12R, G12S, G12V, and G13D; and BRAF V600E. This figure shows that the PIK3CA H1047R SNP was expressed at different percentages in the breast cancer samples.

FIG. 41 shows that PIK3CA SNPs (E542K, E545D, E545K and H1047R) were also detected and quantitated (e.g., percent mutation) in an additional set of breast cancer samples. 45 breast cancer samples were screened for the PIK3CA E542K, E545D, E545K and H1047R allelic variants.

FIG. 42 shows that lung tumor samples can be screened for SNPs using methods of the present invention. In this embodiment, the presence and percent mutation of various SNPs were determined in 25 lung tumor samples. The SNPs included PIK3CA E542K, E545D, E545K and H1047R; EGFR T790M, L858R and E746 deletion; KRAS G12C, G12R, G12S, G12D, G12A, G12V, G13C, G13D, and Q61H; and BRAF V600E.

FIG. 43 illustrates the results obtained from using the methods of the present invention on an additional 32 human lung tumor samples. The SNPs included PIK3CA E542K, E545D, E545K and H1047R; EGFR T790M, L858R and E746 deletion; KRAS G12C, G12R, G12S, G12D, G12A, G12V, and G13D; and BRAF V600E.

FIG. 44 shows that gastric tumor samples can be screened using methods of the present invention to detect the presence and percent mutation of various SNPs. The SNPs included PIK3CA E542K, E545D, E545K and H1047R; EGFR T790M, L858R and E746 deletion; KRAS G12C, G12R, G12S, G12D, G12A, G12V, G13D, and Q61H; and BRAF V600E. In this embodiment, each assay was run with 40 ng of sample (e.g., DNA).

FIG. 45 shows the results obtained from using the methods of the present invention with xenograft samples to detect the presence and percent mutation of various SNPs. The SNPs included PIK3CA E542K, E545D, E545K and H1047R; EGFR T790M, L858R and E746 deletion; KRAS G12C, G12R, G12S, G12D, G12A, G12V, G13C, G13D, and Q61H; and BRAF V600E. The EGFR E746 deletion was present in samples #585-588 and predicted to be in 100% of the cells in the sample. The PIK3CA H1047R allele was detected in samples #581-584 at a percentage of mutation of 3.4%, 1.2%, 1% and 1.8%, respectively.

FIG. 46 illustrates that KRAS, BRAF and PIK3CA allelic variants can be detected and quantitated (e.g., percent mutation) in colorectal cancer samples using the methods of the present invention. The SNPs included PIK3CA E542K, E545D, E545K and H1047R; KRAS G12C, G12R, G12S, G12D, G12A, G12V, and G13D; and BRAF V600E.

FIG. 47 illustrates that KRAS, BRAF and PIK3CA allelic variants can be detected and quantitated in additional colorectal cancer samples using the methods of the invention.

FIG. 48 illustrates that liver tumor and colon tumor tissues from patients with colorectal cancer can be screened for KRAS, BRAF and PIK3CA allelic variants using the methods of the present invention. The results show that some of the samples had a plurality of SNPs.

FIG. 49 illustrates that samples from patients with pancreatic cancer can be screened for SNPs and the percent mutation can be determined according to methods of the present invention. In this embodiment, fine needle aspirate samples were from obtained from patients and screened using the SNP genotyping assays described herein. In the pancreatic cancer samples tested, various KRAS mutations were detected, but PIK3CA (e.g., E542K, E545D, E545K, H1047R), EGFR (e.g., T790M, L858R) and BRAF (e.g., V600E) mutations were not detected.

DETAILED DESCRIPTION OF THE INVENTION

I. Introduction

Figure 1:
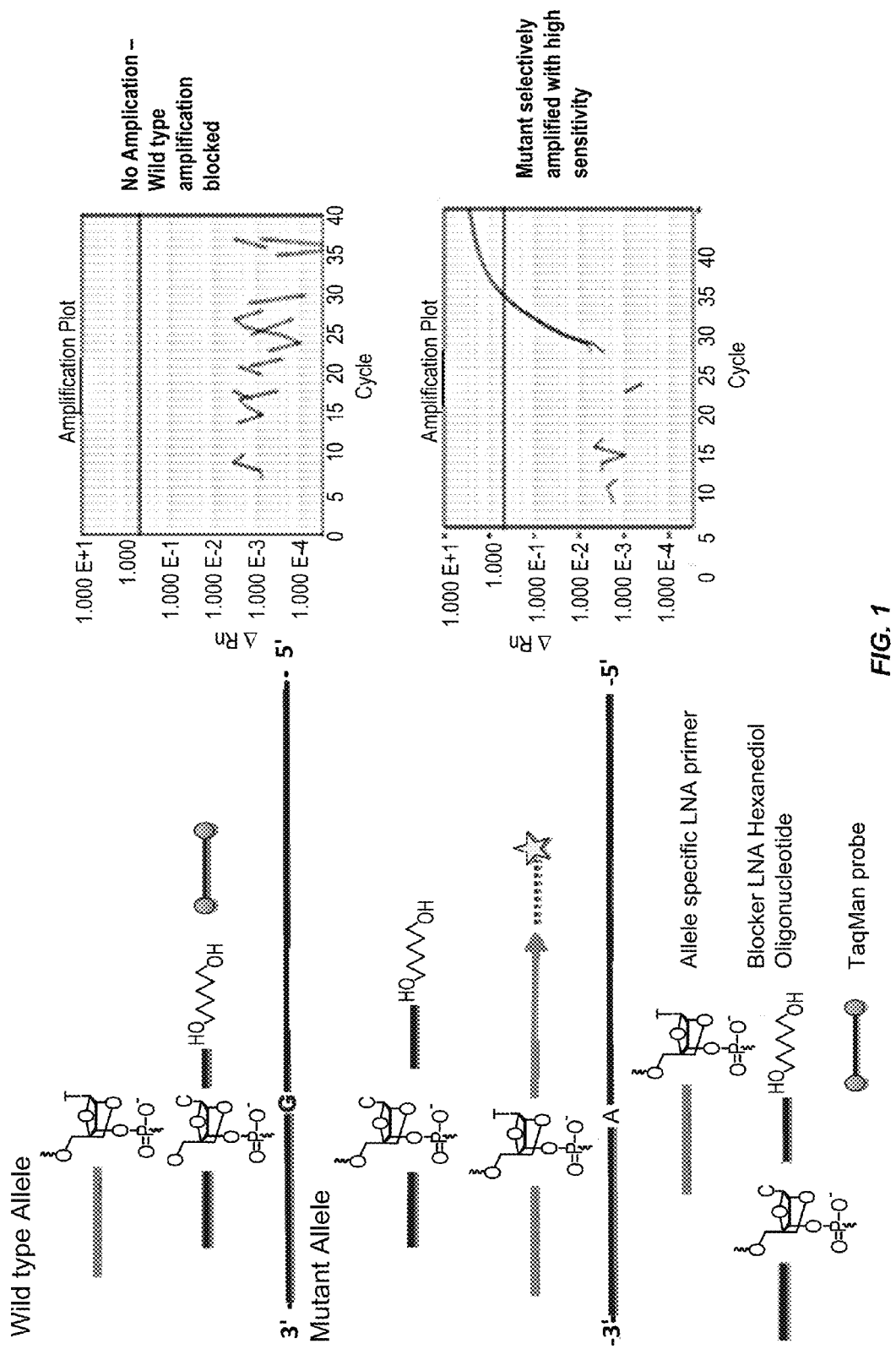
FIG. 1 depicts one embodiment of the somatic mutation detection assays of the present invention.

The selective amplification of an allele of interest is often complicated by factors including the mispriming and extension of a mismatched allele-specific primer on an alternative allele. Such mispriming and extension can be especially problematic in the detection of rare alleles present in a sample populated by an excess of another allelic variant. When in sufficient excess, the mispriming and extension of the other allelic variant may obscure the detection of the allele of interest. When using PCR-based methods, the discrimination of a particular allele in a sample containing alternative allelic variants relies on the selective amplification of an allele of interest, while minimizing or preventing amplification of other alleles present in the sample.

A number of factors have been identified, which alone or in combination, contribute to the enhanced discriminating power of allele-specific PCR. As disclosed herein, a factor which provides a greater $\Delta Ct$ value between a mismatched and matched allele-specific primer is indicative of greater discriminating power between allelic variants. Such factors found to improve discrimination of allelic variants using the present methods include, for example, the use of one or more of the following: (a) tailed allele-specific primers; (b) low allele-specific primer concentration; (c) allele-specific primers designed to have lower Tm's; (d) allele-specific primers designed to target discriminating bases; (e) allele-specific blocker probes designed to prevent amplification from alternative, and potentially more abundant, allelic variants in a sample; and (f) allele-specific blocker probes and/or allele-specific primers designed to comprise nucleic acid modifications such as, e.g., modified bases, nucleic acid analogs, and/or ribose-modified nucleic acids, in order to increase the delta Tm between matched and mismatched target sequences.

The above-mentioned factors, especially when used in combination, can influence the ability of allele-specific PCR to discriminate between different alleles present in a sample. Thus, the present invention relates generally to novel amplification methods which utilize one or more of the factors described above to improve the discrimination of allelic variants during PCR, e.g., by increasing $\Delta Ct$ values.

In certain aspects, the present invention is based on locked nucleic acid (LNA) chemistry using allele-specific real time PCR with a blocker oligonucleotide containing a hexanediol 3' modification to prevent the amplification of the wild-type allele. The limit of detection of the present methods is advantageously 2-10 DNA copies. The present invention also provides selective and robust detection of a large panel of somatic mutations. As a non-limiting example, the present invention enables the detection of a very low copy number mutant allele (e.g., 0.01%-0.1%) in a whole blood background. In some instances, surrogate samples for use in the mutation assays described herein include, but are not limited to, blood, serum, plasma, tissues (e.g., FNA, CTCs, core biopsy, FFPE tissue), and mixtures thereof.

In particular aspects, the mutation assays of the invention are based on an allele-specific PCR. In certain embodiments, the detection is a real time method using TaqMan probe technology. In preferred embodiments, an allele-specific primer (ASP) containing a single LNA base mutation at its 3'-end can be used to specifically detect the mutant allele. In these embodiments, a blocking oligonucleotide (blocker) complementary to the wild-type sequence can be used to suppress any non-specific amplification of the wild-type allele. This blocker may contain a single LNA variant situated at the wild-type nucleotide position. In some instances, the blocker comprises a hexanediol chemical group at the 3'-end to prevent any extension. In other instances, the present invention further includes a reverse primer to complete the reaction. Without being bound to any particular theory, the presence of a LNA modified base increases the discrimination between wild-type and mutant alleles, enabling greater target allele specificity and blocking efficacy. In particular embodiments, LNA is a modified base used to increase the specificity of PCR probes and the thermal stability of duplexes. LNA modified bases are capable of single nucleotide discrimination, thereby minimizing the possible mismatch between the AS primer and wild-type allele. In certain embodiments, the allele-specific primer and/or blocking oligonucleotide comprises an LNA modified base at the position of the allelic variant and 1, 2, 3, 4, 5, 6, 7, or more additional non-consecutive or non-contiguous LNA modifications and/or an LNA modified base at the 5'-end.

Accordingly, the compositions and methods of the present invention advantageously enable the detection of very low levels of mutant (somatic) DNA in samples including blood, plasma, serum, and/or tissues (FNA, CTCs, core biopsy, FFPE tissue, etc.). In particular, the assays of the present invention are significant improvements on previously described allelic-specific PCR mutation detection by virtue of the use of LNA chemistry in combination with a novel blocking oligonucleotide design. As such, the present invention provides mutation analysis with a 10 to 100 fold higher sensitivity than detection technologies known in the art such as the BEAMing (Beads, Emulsions, Amplification, and Magnetics) assay (Inostics), the Scorpions/ARMS reaction (Qiagen), and the castPCR Assay (Life Technologies). In addition, the present invention provides a method with the ability to detect oncogenic resistant mutants such as EGFR T790M, EGFR E746-A750 deletion, KRAS G12A, KRAS G12D, KRAS G12S, E545K PIK3CA, and V600E BRAF.

II. Definitions

As used herein, the following terms have the meanings ascribed to them unless specified otherwise.

As used herein, the term "allele" includes alternative DNA sequences at the same physical locus on a segment of DNA, such as, for example, on homologous chromosomes. An allele can refer to DNA sequences which differ between the same physical locus found on homologous chromosomes within a single cell or organism or which differ at the same physical locus in multiple cells or organisms ("allelic variant"). In some instances, an allele can correspond to a single nucleotide difference at a particular physical locus. In other instances, an allele can correspond to a nucleotide (single or multiple) insertion or deletion.

The term "allele-specific primer" includes an oligonucleotide sequence that hybridizes to a sequence comprising an allele of interest, and which when used in PCR can be extended to effectuate first strand cDNA synthesis. Allele-specific primers are specific for a particular allele of a given target DNA or loci and can be designed to detect a difference of as little as one nucleotide in the target sequence. Allele-specific primers may comprise an allele-specific nucleotide portion, a target-specific portion, and/or a tail.

As used herein, the terms "allele-specific nucleotide portion" or "allele-specific target nucleotide" include a nucleotide or nucleotides in an allele-specific primer that can selectively hybridize and be extended from one allele (for example, a minor or mutant allele) at a given locus to the exclusion of the other (for example, the corresponding major or wild-type allele) at the same locus.

The term "target-specific portion" includes the region of an allele-specific primer that hybridizes to a target polynucleotide sequence. In some embodiments, the target-specific portion of the allele-specific primer is the priming segment that is complementary to the target sequence at a priming region 5' of the allelic variant to be detected. The target-specific portion of the allele-specific primer may comprise the allele-specific nucleotide portion. In other instances, the target-specific portion of the allele-specific primer is adjacent to the 3' allele-specific nucleotide portion.

As used herein, the terms "tail" or "5'-tail" include the non-3' end of a primer. This region typically will, although does not have to, contain a sequence that is not complementary to the target polynucleotide sequence to be analyzed. The 5' tail can be any of about 2-30, 2-5, 4-6, 5-8, 6-12, 7-15, 10-20, 15-25 or 20-30 nucleotides, or any range in between, in length.

The terms "allele-specific blocker probe" or "blocker probe" or "blocker" include an oligonucleotide sequence that binds to a strand of DNA comprising a particular allelic variant which is located on the same, opposite or complementary strand as that bound by an allelic-specific primer, and reduces or prevents amplification of that particular allelic variant. As discussed herein, allele-specific blocker probes generally comprise modifications, e.g., at the 3'-OH of the ribose ring, which prevent primer extension by a polymerase. The allele-specific blocker probe can be designed to anneal to the same or opposing strand of what the allele-specific primer anneals to and can be modified with a blocking group (e.g., a "non-extendable blocker moiety") at its 3' terminal end. Thus, a blocker probe can be designed, for example, so as to tightly bind to a wild-type allele (e.g., abundant allelic variant) in order to suppress amplification of the wild-type allele while amplification is allowed to occur on the same or opposing strand comprising a mutant allele (e.g., rare allelic variant) by extension of an allele-specific primer. In illustrative examples, the allele-specific blocker probes do not include a label, such as a fluorescent, radioactive, or chemiluminescent label.

As used herein, the terms "non-extendable blocker moiety" or "blocker moiety" include a modification on an oligonucleotide sequence such as a probe and/or primer which renders it incapable of extension by a polymerase, for example, when hybridized to its complementary sequence in a PCR reaction. Examples of blocker moieties include, but are not limited to, modifications of the ribose ring 3'-OH of the oligonucleotide, which prevent addition of further bases to the 3'-end of the oligonucleotide sequence by a polymerase. In particular embodiments, the non-extendable blocker moiety includes, without limitation, an optionally substituted $C_1$-$C_{24}$ alkyl diol (e.g., a 3'-hexanediol modification), an optionally substituted $C_2$-$C_{24}$ alkenyl diol, an optionally substituted $C_2$-$C_{24}$ alkynyl diol, a minor groove binder (MGB), an amine ($NH_2$), biotin, PEG, $PO_4$, and combinations thereof. Examples of MGB's include CC1065 analogs, lexitropsins, distamycin, netropsin, berenil, duocarmycin, pentamidine, 4,6-diamino-2-phenylindole and pyrrolo[2,1-c][1,4]benzodiazepines, and $DPI_3$.

As used herein, the term "modified base" includes any modification of a base or the chemical linkage of a base in a nucleic acid that differs in structure from that found in a naturally-occurring nucleic acid. Such modifications can include changes in the chemical structures of bases or in the chemical linkage of a base in a nucleic acid, or in the backbone structure of the nucleic acid. See, e.g., Latorra et al., *Hum Mut.*, 2:79-85 (2003); Nakiandwe et al., *Plant Method*, 3:2 (2007).

The terms "locked nucleic acid" or "LNA" include a class of nucleic acid analogues in which the ribose ring is "locked" by a methylene bridge connecting the 2'-O atom and the 4'-C atom. LNA nucleosides contain the common nucleobases (T, C, G, A, U, and mC) and are able to form base pairs according to standard Watson-Crick base pairing rules. However, by "locking" the molecule with the methylene bridge, the LNA is constrained in the ideal conformation for Watson-Crick binding.

The terms "peptide nucleic acid", "peptidic nucleic acid" or "PNA" include a non-naturally occurring and artificially synthesized nucleic acid analog or mimic comprising various naturally-occurring or non-naturally-occurring nucleobases attached to a backbone of repeating N-(2-aminoethyl)-glycine units linked by amide bonds. The purine and pyrimidine bases are attached to the uncharged backbone through methylene carbonyl linkages. Like with DNA, Watson-Crick base pairing rules apply to peptide nucleic acids.

The terms "zip nucleic acids" or "ZNAs" include oligonucleotides conjugated with one or a plurality of cationic spermine moieties that decrease electrostatic repulsions with target nucleic acid strands and increase the affinity of the oligonucleotides for their targets.

The terms "triazole nucleic acids", "TzNAs", "triazole deoxynucleic acid", "TzDNA", "triazole-linked analogue of deoxyribonucleic acid" or "TLDNA" include an oligonucleotide comprising a non-naturally occurring triazole linkage.

The terms "(3'-2') α-L-threose nucleic acid", "threose nucleic acid" or "TNA" include a non-naturally occurring nucleic acid discovered during investigations of nucleic acids that obey Watson-Crick base-pairing rules and are bound to alternative sugar-phosphate backbones (see, e.g., Ichida et al., *Nucleic Acids Res.*, 33: 5219-5225 (2005)). TNAs have a repeat unit one atom shorter than natural nucleic acids, yet they can base pair with DNA, RNA, and itself. While not wanting to be bound by a particular theory, it is believed that TNA hybridizes strongly with DNA and even more strongly with RNA because TNA is a good mimic of the A-form of DNA and of RNA. The increased stability of TNA-DNA duplexes compared to analogous DNA-DNA complexes results in improved mismatch discrimination of allelic variants.

As used herein, the term "detector probe" includes any of a variety of signaling molecules indicative of amplification. For example, SYBR® Green and other DNA-binding dyes are detector probes. Some detector probes can be sequence-based (also referred to herein as "locus-specific detector probe"), for example, 5' nuclease probes. Various detector probes are known in the art and include, but are not limited to, TaqMan® probes described herein (see also, U.S. Pat. No. 5,538,848), various stem-loop molecular beacons (see, e.g., U.S. Pat. Nos. 6,103,476 and 5,925,517; Tyagi et al., *Nature Biotech.*, 1996, 14:303-308), stemless or linear beacons (see, e.g., PCT Publication No. WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (see, e.g., U.S. Pat. No. 6,548,250), stem-loop and duplex. Scorpion™ probes (see, e.g., Solinas et al., 2001, *Nucl. Acids Res.*, 29:E96; U.S. Pat. No. 6,589,743), bulge loop probes (see, e.g., U.S. Pat. No. 6,590,091), pseudo knot probes (see, e.g., U.S. Pat. No. 6,589,250), cyclicons (see, e.g., U.S. Pat. No. 6,383,752), MGB Eclipse™ probe (Epoch Biosciences), hairpin probes (see, e.g., U.S. Pat. No. 6,596,490), peptide nucleic acid (PNA) light-up probes, self-assembled nanoparticle probes, and ferrocene-modified probes as described, for example, in U.S. Pat. No. 6,485,901; Mhianga et al., 2001, *Methods*, 25:463-471; Whitcombe et al., 1999, *Nature Biotechnol.*, 17:804-807; Isacsson et al., 2000, *Molecular Cell Probes*, 14:321-328; Svanvik et al., 2000, *Anal Biochem.*, 281:26-35; Wolffs et al., 2001, *Biotechniques*, 766: 769-771; Tsourkas et al, 2002, *Nucleic Acids Research*, 30:4208-4215; Riccelli et al., 2002, *Nucleic Acids Research*, 30:4088-4093; Zhang et al., 2002 *Shanghai*, 34:329-332; Maxwell et al., 2002, *J Am. Chem. Soc.*, 124:9606-9612; Broude et al., 2002, *Trends Biotechnol.*, 20:249-56; Huang et al., 2002, *Chem. Res. Toxicol.*, 15:1 18-126; and Yu et al., 2001, *J. Am. Chem. Soc.*, 14:11155-11161. Detector probes can comprise reporter dyes such as, for example, 6-carboxyfluorescein (6-FAM) or tetrachlorofluorescin (TET). Detector probes can also comprise quencher moieties such as tetramethylrhodamine (TAMRA), Black Hole Quenchers (Biosearch), Iowa Black (DT), QSY quencher (Molecular Probes), and Dabsyl and Dabcel sulfonate/carboxylate Quenchers (Epoch Biosciences). In some embodiments, detector probes can comprise two probes, wherein for example a fluor is on one probe, and a quencher is on the other probe, wherein hybridization of the two probes together on a target quenches the signal, or wherein hybridization on a target alters the signal signature via a change in fluorescence. Detector probes can also comprise sulfonate derivatives of fluorescein dyes with $SO_3$ instead of the carboxylate group, phosphoramidite forms of fluorescein, phosphoramidite forms of CY5 (Amersham Biosciences-GE Healthcare).

The term "locus-specific primer" includes an oligonucleotide sequence that hybridizes to products derived from the extension of a first primer (such as an allele-specific primer) in a PCR reaction, and which can effectuate second strand cDNA synthesis of the product. Accordingly, in some embodiments, the allele-specific primer serves as a forward PCR primer and the locus-specific primer serves as a reverse PCR primer, or vice versa. In some preferred embodiments, locus-specific primers are present at a higher concentration as compared to the allele-specific primers.

As used herein, the term "rare allelic variant" includes a target polynucleotide present at a lower level in a sample as compared to an alternative allelic variant. The rare allelic variant may also be referred to as a "minor allelic variant" and/or a "mutant allelic variant." For instance, the rare allelic variant may be found at a frequency less than about $\frac{1}{10}$, $\frac{1}{100}$, $\frac{1}{1,000}$, $\frac{1}{10,000}$, $\frac{1}{100,000}$, $\frac{1}{1,000,000}$, $\frac{1}{10,000,000}$, $\frac{1}{100,000,000}$, or $\frac{1}{1,000,000,000}$ compared to another allelic variant for a given SNP or gene. Alternatively, the rare allelic variant can be, e.g., less than about 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, or 1,000,000 copies per 1, 10, 100, or 1,000 micro liters of a sample or a reaction volume.

The term "abundant allelic variant" includes a target polynucleotide present at a higher level in a sample as compared to an alternative allelic variant. The abundant allelic variant may also be referred to as a "major allelic variant" and/or a "wild-type allelic variant." For instance, the abundant allelic variant may be found at a frequency greater than about 10×, 100×, 1,000×, 10,000×, 100,000×, 1,000,000×, 10,000,000×, 100,000,000×, or 1,000,000,000× compared to another allelic variant for a given SNP or gene. Alternatively, the abundant allelic variant can be, for example, greater than about 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, 1,000,000 copies per 1, 10, 100, 1,000 micro liters of a sample or a reaction volume.

In certain embodiments, the terms "first" and "second" are used to distinguish the components of a first reaction (e.g., a "first" reaction; a "first" allele-specific primer) and a second reaction (e.g., a "second" reaction; a "second" allele-specific primer). By convention, the first reaction amplifies a first (for example, a rare) allelic variant and the second reaction amplifies a second (for example, an abundant) allelic variant or vice versa.

As used herein, both "first allelic variant" and "second allelic variant" can pertain to alleles of a given locus from the same organism. For example, as might be the case in human samples (e.g., cells) comprising wild-type alleles, some of which have been mutated to form a minor or rare allele. In some instances, the first and second allelic variants refer to alleles from different organisms. For example, the first allele can be an allele of a genetically modified organism, and the second allele can be the corresponding allele of a wild-type organism. In certain instances, the first and second allelic variants can be contained on gDNA, as well as mRNA and cDNA, and generally any target nucleic acids that exhibit sequence variability due to, e.g., SNP or nucleotide(s) insertion and/or deletion mutations.

The terms "thermostable" or "thermostable polymerase" include an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably, a thermostable DNA polymerase will not irreversibly denature at about 90°-100° C. under conditions such as is typically required for PCR amplification.

As used herein, the terms "PCR amplifying" or "PCR amplification" include cycling polymerase-mediated exponential amplification of nucleic acids employing primers that hybridize to complementary strands, as described, for example, in Innis et al., PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; 6,174,670; and 6,814,934 and include, but are not limited to, the ABI Prism® 7700 Sequence Detection System (Applied Biosystems, Foster City, Calif.), the ABI GeneAmp® 5700 Sequence Detection System (Applied Biosystems), the ABI GeneAmp® 7300 Sequence Detection System (Applied Biosystems), the ABI GeneAmp® 7500 Sequence Detection System (Applied Biosystems), the StepOne™ Real-Time PCR System (Applied Biosystems), and the ABI GeneAmp® 7900 Sequence Detection System (Applied Biosystems).

The terms "pre-amplification" or "pre-amplify" include a process wherein a plurality of primer pairs are included in a multiplexed PCR amplification reaction, and the multiplexed amplification reaction undergoes a limited number of cycles so that the PCR-based pre-amplification reaction ends prior to the PCR plateau and/or reagent depletion. The term "PCR-based pre-amplification" can be considered to indicate that a secondary amplification reaction is subsequently performed, typically of lower plexy level than the PCR-based pre-amplification reaction. This secondary amplification reaction, typically a plurality of separate secondary amplification reactions, can employ primer pairs encoded by the primers used in the multiplexed PCR-based pre-amplification reaction. However, each secondary amplification reaction typically comprises a single or a few primer pairs. Further examples of PCR-based pre-amplification approaches can be found, for example, in U.S. Pat. No. 6,605,451 and in U.S. application Ser. No. 10/723,520, the disclosures of which are herein incorporated by reference in their entireties for all purposes.

As used herein, the terms "Tm'" or "melting temperature" of an oligonucleotide include the temperature (in degrees Celsius) at which 50% of the molecules in a population of a single-stranded oligonucleotide are hybridized to their complementary sequence and 50% of the molecules in the population are not hybridized to said complementary sequence. The Tm of a primer or probe can be determined empirically by means of a melting curve. In some embodiments, the Tm can also be calculated using formulas well know in the art (See, e.g., Maniatis et al., Molecular cloning: a laboratory manual, Cold Spring Harbor Laboratory, Cold Spring Harbor, N.Y.: 1982).

As used herein, the term "sensitivity" includes the minimum amount (number of copies or mass) of a template that can be detected by a given assay.

As used herein, the term "specificity" includes the ability of an assay to distinguish between amplification from a matched template versus a mismatched template. Frequently, specificity is expressed as $\Delta C_t = Ct_{mismatch} - Ct_{match}$. An improvement in specificity or "specificity improvement" or "fold difference" is expressed herein as $2^{(\Delta Ct\_condition1 - \Delta Ct\_condition2)}$.

The term "selectivity" includes the extent to which an AS-PCR assay can be used to determine minor (often mutant) alleles in mixtures without interferences from major (often wild-type) alleles. Selectivity is often expressed as a ratio or percentage. For example, an assay that can detect 1 mutant template in the presence of 100 wild-type templates is said to have a selectivity of 1:100 or 1%. As used herein, assay selectivity can also be calculated as $\frac{1}{2}^{\Delta Ct}$ or as a percentage using ($\frac{1}{2}^{\Delta Ct} \times 100$).

The term "Ct" or "Ct value" includes the threshold cycle and signifies the cycle of a PCR amplification assay in which signal from a reporter that is indicative of amplicon generation (e.g., fluorescence) first becomes detectable above a background level. In some embodiments, the threshold cycle or "Ct" is the cycle number at which PCR amplification becomes exponential.

As used herein, the term "delta Ct" or "ΔCt" includes the difference in the numerical cycle number at which the signal passes the fixed threshold between two different samples or reactions. In some embodiments, delta Ct is the difference in numerical cycle number at which exponential amplification is reached between two different samples or reactions. In some embodiments, the delta Ct can be used to identify the specificity between a matched primer to the corresponding target nucleic acid sequence and a mismatched primer to the same corresponding target nucleic acid sequence.

In some embodiments, the calculation of the delta Ct value between a mismatched primer and a matched primer is used as one measure of the discriminating power of allele-specific PCR. In general, any factor which increases the difference between the Ct value for an amplification reaction using a primer that is matched to a target sequence (e.g., a sequence comprising an allelic variant of interest) and that of a mismatched primer will result in greater allele discrimination power.

According to various embodiments, a Ct value may be determined using a derivative of a PCR curve. For example, a first, second, or nth order derivative method may be performed on a PCR curve in order to determine a Ct value. In various embodiments, a characteristic of a derivative may be used in the determination of a Ct value. Such characteristics may include, but are not limited to, a positive inflection of a second derivative, a negative inflection of a second derivative, a zero crossing of the second derivative, or a positive inflection of a first derivative. In some embodiments, a Ct value may be determined using a thresholding and baselining method. For example, an upper bound to an exponential phase of a PCR curve may be established using a derivative method, while a baseline for a PCR curve may be determined to establish a lower bound to an exponential phase of a PCR curve. From the upper and lower bound of a PCR curve, a threshold value may be established from which a Ct value is determined. Other methods for the determination of a Ct value known in the art, for example, but not limited to, various embodiments of a fit point method, and various embodiments of a sigmoidal method. See, e.g., U.S. Pat. Nos. 6,303,305; 6,503,720; 6,783,934, 7,228,237 and U.S. Publication No. 2004/0096819; the disclosures of which are herein incorporated by reference in their entireties for all purposes.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, ascites, pleural efflux, saliva, urine, stool (i.e., feces), sputum, bronchial lavage fluid, tears, fine needle aspirate (FNA) (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), a tissue sample (e.g., tumor tissue) such as a surgical resection of a tumor, and cellular extracts thereof. In some embodiments, the sample is whole blood or a fractional component thereof such as plasma, serum, or a cell pellet. In other embodiments, the sample is obtained by isolating circulating cells of a solid tumor from whole blood or a cellular fraction thereof using any technique known in the art. In yet other embodiments, the sample is a formalin fixed paraffin embedded (FFPE) tumor tissue sample, e.g., from a solid tumor.

The term "subject" or "patient" or "individual" typically includes humans, but can also include other animals such as, e.g., other primates, rodents, canines, felines, equines, ovines, porcines, and the like.

III. Description of the Embodiments

In one aspect, the present invention provides compositions for use in identifying and/or quantitating an allelic variant in a nucleic acid sample. Some of these compositions can comprise: (a) an allele-specific primer; (b) an allele-specific blocker probe; (c) a detector probe; (d) a locus-specific primer; and (e) any combinations thereof. In some embodiments, the compositions may further comprise a polymerase, dNTPs, reagents and/or buffers suitable for PCR amplification and/or a template sequence or nucleic acid sample. In some instances, the polymerase can be thermostable.

In another aspect, the present invention provides compositions for use in identifying and/or quantitating an allelic variant in a nucleic acid sample, wherein the compositions can comprise: (i) an allele-specific primer, wherein an allele-specific nucleotide portion of the allele-specific primer is complementary to a first allelic variant of a target sequence and comprises a nucleic acid modification; and/or (ii) an allele-specific blocker probe, wherein an allele-specific nucleotide portion of the allele-specific blocker probe is complementary to a second allelic variant of the target sequence and comprises a nucleic acid modification, and wherein the allele-specific blocker probe comprises a non-extendable blocker moiety at the 3' terminus.

In some illustrative embodiments, the compositions can further comprise a locus-specific primer that is complementary to a region of the target sequence that is 3' from the first allelic variant and on the opposite strand. In yet other embodiments, the compositions further comprise a detector probe.

In another aspect, the present invention provides methods for amplifying an allele-specific sequence. Some of these methods can comprise: (a) hybridizing an allele-specific primer to a first nucleic acid molecule comprising a target allele; (h) hybridizing an allele-specific blocker probe to a second nucleic acid molecule comprising an alternative allele, wherein the alternative allele corresponds to the same loci as the target allele; (c) hybridizing a locus-specific detector probe to the first nucleic acid molecule; (d) hybridizing a locus-specific primer to the extension product of the allele-specific primer; and (e) PCR amplifying the target allele. In particular embodiments, the allele-specific blocker probe comprises a non-extendable blocker moiety at the 3' terminus. In other particular embodiments, both the allele-specific primer and the allele-specific blocker probe independently comprise a nucleic acid modification such as, for example, a modified base (e.g., PNA, TNA, ZNA and TzDNA), a nucleic acid analog, or a ribose-modified nucleic acid, at the position of the target allele and the alternative allele, respectively.

A. LNA, PNA, TNA, ZNA or TzNA Modifications of Oligonucleotides for Primers and/or Probes In one aspect, the present invention provides oligonucleotide compositions, wherein the oligonucleotides comprise at least one nucleic acid modification and/or a non-extendable blocker moiety at the 3' terminus.

Non-limiting examples of nucleic acid modifications include locked nucleic acid (LNA), peptide nucleic acid (PNA), threose nucleic acid (TNA), zip nucleic acid (LNA), triazole nucleic acid (TzNA), and combinations thereof.

In preferred embodiments, the present invention comprises an oligonucleotide comprising at least one locked nucleic acid (LNA). LNA includes a class of nucleic acid analogues in which the ribose ring is "locked" by a methylene bridge connecting the 2'-O atom and the 4'-C atom. LNA nucleosides contain the common nucleobases (T, C, G, A, U, and mC) and are able to form base pairs according to standard Watson-Crick base pairing rules. When incorporated into a DNA oligonucleotide, LNA makes the pairing with a complementary nucleotide strand more rapid and increases the stability of the resulting duplex. The affinity-enhancing effect of incorporation of LNA monomers into an oligonucleotide is demonstrated by an increase in the duplex melting temperature of 2-8° C. per LNA monomer. In some instances, LNA refers to modifications of LNA, such as, but not limited to oxy-LNA, thio-LNA, and amino-LNA. See, e.g., Johnson et al., *Nucl. Acid Res.*, 2004, 32, e55; Latorra et al., *Hum. Mut.*, 2003, 22, 79; Chou et al, *Biotech.*, 2005, 39, 644.

In some embodiments, the present invention comprises an oligonucleotide comprising at least one peptide nucleic acid (PNA). PNA is a non-naturally occurring and artificially synthesized nucleic acid analog or mimic comprising various naturally-occurring or non-naturally-occurring nucleobases attached to a backbone of repeating N-(2-aminoethyl)-glycine units linked by amide bonds. It is appreciated by those skilled in the art that a PNA-DNA duplex binds with greater strength, higher stability, more quickly and with more specificity compared to an analogous DNA-DNA duplex, due to the lack of electrostatic repulsion between the PNA strand and DNA strand. The greater stability is reflected by a higher Tm for the PNA-DNA duplex versus the analogous DNA-DNA duplex. PNA complexes are more thermally stable and less susceptible to degradation by nucleases, proteases and peptidases. It has been shown that the Tm of PNA-DNA duplexes is in part independent of salt concentration. In addition, it is more likely that single base mismatches can be determined with PNA/DNA hybridization because a single mismatch in a PNA/DNA 15-mer lowers the melting point (Tm) by 8°-20° C. vs. 4°-16° C. for the DNA/DNA 15-mer duplex. This has the effect of improving the discrimination between matched and mismatched sequences. See, e.g., Nielsen, P. E. and Egholm, M., *Current Issues Molec. Biol.* 1; 89-104 (1999); Orum et al. "Peptide Nucleic Acid". Laboratory Methods for the Detection of Mutations and Polymorphisms in DNA ed. Graham R. Taylor. CRC Press, 1997; Nielsen, P. E. and Egholm, M., *Current Issues Molec. Biol.* 1; 89-104 (1999); Gaylord et al., *Proc. Natl. Acad. Sci.*, 102: 34-39 (2005).

PNA can specifically block primer annealing and chain elongation on a perfectly matched template without interfering with reactions on templates with mismatched bases. PNA can be used to improve mutation detection by suppressing wild-type allele amplification in SNP analysis such as, but not limited to asymmetric PCR clamping, melting curve analysis (see, e.g., Oh et al. J. Mol. Diagn., 12: 418-424 (2010); Orum et al., Nucleic Acids Res, 21: 5332-5336 (1993); Luo et al., Nucleic Acids Res, 34:e12 (2006); Karkare et al., Appl. Microbiol. Biotechnol., 71:575-586 (2006)).

In some embodiments, the present invention can comprise an oligonucleotide comprising at least one zip nucleic acid (ZNA). ZNA is an oligonucleotide conjugated with one or a plurality of cationic spermine moieties. This structure decreases electrostatic repulsion with its target nucleic acid strand and increases the affinity of the oligonucleotide for its targets. The number of cationic units attached at any position of the oligonucleotide can modulate the global charge of the molecule, which can raise the corresponding Tm of a ZNA duplex (e.g., ZNA-ZNA duplex, ZNA-DNA duplex, and ZNA-RNA duplex) in a linear and predictable manner. They are efficient at low magnesium concentration and at high annealing temperatures, which can be advantageous for accurate detection of allelic variants. ZNAs can be single-labeled or dual-labeled with fluorescent moieties and fluorescent quenchers. ZNAs are commercially available from e.g., Sigma-Aldrich. See, e.g., Voirin et al., *Nat. Protoc.*, 2:1360-1367 (2007), Noir et al., *J. Am. Chem. Soc.*, 130; 13500-13505 (2008), Moreau et al., *Nucleic Acids Res.*, 37: e130 (2009); Paris et al., *Nucleic Acids Res.*, 38: e95 (2010).

In other embodiments, the present invention comprises an oligonucleotide comprising at least one triazole nucleic acid (TzNA). TzNA oligonucleotides can be synthesized using click chemistry (e.g., copper-catalyzed azide-alkyne cycloaddition reaction). Oligonucleotides containing AZT-based triazole linkages can be used as PCR templates with a variety of polymerases for amplification (El-Sagheer et al., *J. Am. Chem. Soc.*, 131: 3958-3964 (2009)). Genes containing trizole linker can also be functional in *Escherichia coli* (El-Sagheer et al., *Proc. Natl. Acad. Sci.*, 108: 11338-11343 (2011)). See, e.g., Isobe et al., *Org. Lett.*, 10: 3729-3732 (2008); Fujino et al., *Tetrahedron Lett.*, 50: 4101-4103 (2009); von Matt et al., *Bioorg. Med. Chem. Letts.*, 7: 1553-1556 (1997).

In yet other embodiments, the present invention comprises an oligonucleotide comprising at least one threose nucleic acid (TNA). TNAs have a repeat unit one atom shorter than natural nucleic acids, yet they can base pair with DNA, RNA, and itself. While not wanting to be bound by a particular theory, it is believed that TNA hybridizes strongly with DNA and even more strongly with RNA because TNA is a good mimic of the A-form of DNA and of RNA. The increased stability of TNA-DNA duplexes compared to analogous DNA-DNA complexes results in improved mismatch discrimination of allelic variants. See, e.g., Ichida et al., *Nucleic Acids Res.*, 33: 5219-5225 (2005).

Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. In some embodiments, all tautomeric forms of naturally-occurring bases, modified bases and base analogues may also be included in the oligonucleotide primers and probes of the invention.

In further embodiments, modified sugars or sugar analogs can be present in one or more of the nucleotide subunits of an oligonucleotide in accordance with the invention. Sugar modifications include, but are not limited to, attachment of substituents to the 2', 3' and/or 4: carbon atom of the sugar, different epimeric forms of the sugar, differences in the α- or β-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, and cyclopentyl.

In certain embodiments, one or more modified internucleotide or backbone linkages can be present in the oligonucleotides of the present invention. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate, and the like. Additional modifications of bases, sugars and/or internucleotide linkages that are compatible with their use in oligonucleotides serving as probes and/or primers, will be apparent to those of skill in the art.

The non-extendable blocker moiety can comprise any modification of the ribose ring 3'-OH of the blocker probe which prevents addition of further bases to the 3'-end of the oligonucleotide sequence by a polymerase. In some embodiments, the blocker moiety can include, without limitation, an optionally substituted $C_1$-$C_{24}$ alkyl diol (e.g., a 3'-hexanediol modification), an optionally substituted $C_2$-$C_{24}$ alkenyl diol, an optionally substituted $C_2$-$C_{24}$ alkynyl diol, a minor groove binder (MGB), an amine ($NH_2$), biotin, PEG, $PO_4$, and mixtures thereof. In particular embodiments, the optionally substituted $C_1$-$C_{24}$ alkyl diol comprises a methanediol, ethanediol, 1,3-propanediol, 1,4-butanediol, 1,5-pentanediol, 1,6-hexanediol, 1,7-heptanediol, or 1,8-octanediol modification to the 3'-end of the allele-specific blocker probe. In some embodiments, the non-extendable blocker moiety comprises an optionally substituted $C_1$-$C_{20}$, $C_1$-$C_{12}$, $C_2$-$C_{20}$, $C_2$-$C_{12}$, $C_4$-$C_{12}$, $C_4$-$C_8$, $C_1$, $C_2$, $C_3$, $C_4$, $C_5$, $C_6$, $C_7$, $C_8$, $C_9$, $C_{10}$, $C_{11}$, or $C_{1-2}$ alkyl diol. In other embodiments, the non-extendable blocker moiety comprises an optionally substituted $C_2$-$C_{20}$, $C_2$-$C_{12}$, $C_4$-$C_{12}$, $C_4$-$C_{10}$, $C_4$-$C_8$, $C_2$, $C_3$, $C_4$, $C_5$, $C_6$, $C_7$, $C_8$, $C_9$, $C_{10}$, $C_{11}$, or $C_{1-2}$ alkenyl diol or alkynyl diol.

In certain embodiments, the non-extendable blacker moiety does not comprise or include a minor groove binder (MGB) and/or a $PO_4$ group. In certain other embodiments, the non-extendable blocker moiety consists essentially of or consists of an optionally substituted $C_1$-$C_{24}$ alkyl diol (e.g., a methanediol, ethanediol, 1,3-propanediol, 1,4-butanediol, 1,5-pentanediol, 1,6-hexanediol, 1,7-heptanediol, or 1,8-octanediol modification, or an optionally substituted $C_1$-$C_{20}$, $C_1$-$C_{12}$, $C_2$-$C_{20}$, $C_2$-$C_{12}$, $C_4$-$C_{12}$, $C_4$-$C_{10}$, $C_4$-$C_8$, $C_1$, $C_2$, $C_3$, $C_4$, $C_5$, $C_6$, $C_7$, $C_8$, $C_9$, $C_{10}$, $C_{11}$, or $C_{1-2}$ alkyl diol modification), an optionally substituted $C_2$-$C_{24}$ alkenyl diol or an optionally substituted $C_2$-$C_{24}$ alkynyl diol (e.g., an optionally substituted $C_2$-$C_{20}$, $C_2$-$C_{12}$, $C_4$-$C_{12}$, $C_4$-$C_{10}$, $C_4$-$C_8$, $C_2$, $C_3$, $C_4$, $C_5$, $C_6$, $C_7$, $C_8$, $C_9$, $C_{10}$, $C_{11}$, or $C_{12}$ alkenyl or alkynyl diol modification), or mixtures thereof.

The term "optionally substituted" includes the replacement of at least one hydrogen atom with a substituent. In the case of an "oxo" substituent (=O), two hydrogen atoms are replaced. Non-limiting examples of substituents include oxo, halogen, heterocycle, —CN, —$OR^x$, —$NR^xR^y$, —$NR^xC(=O)R^y$, —$NR''SO_2R^y$, —$C(=O)R^x$, —$C(=O)OR^x$, —$C(=O)NR^xR^y$, —$SO_nR^x$, and —$SO_nNR^xR^y$, wherein n is 0, 1, or 2, wherein $R^x$ and $R^y$ are the same or different and are independently hydrogen, alkyl, or heterocycle, and wherein each of the alkyl and heterocycle substituents may be further substituted with one or more of the substituents described herein. The term "optionally substituted," when used before a list of substituents, means that each of the substituents in the list may be optionally substituted as described herein.

In certain embodiments, the allele-specific nucleotide portion of the allele-specific blocker probe is located from about 5 to about 15 or from about 5 to about 10, such as about 5, 6, 7, 8, 9, 10, 11, 12, 13, 14, or 15 nucleotides away from the blocker moiety of the allele-specific blocker probe. In certain other instances, the allele-specific blocker probe is not cleaved during PCR amplification. In further instances, the Tm of the allele-specific blocker probe ranges from about 58° C. to about 66° C.

In some embodiments, the allele-specific blocker probe and/or allele-specific primer comprises at least about 1, 2, 3, 4, 5, or 6 (e.g., 2 to 6) nucleic acid modifications. In certain instances, the one or more modifications may increase the difference in the Tm between matched and mismatched target sequences and/or decrease mismatch priming efficiency, thereby improving assay specificity and/or selectivity. In certain other instances, the one or more modifications improve allelic discrimination of samples of circulating tumor cells. Non-limiting examples of such modifications include locked nucleic acid (LNA), peptide nucleic acid (PNA), threose nucleic acid (TNA), zip nucleic acid (ZNA), triazole nucleic acid (TzNA), 5' methyl-deoxycytidine, 2'-fluoro-modified nucleic acid, 8-aza-7-deaza-dA (ppA), 8-aza-7-deaza-dG (ppG), 1H-pyrazolo[4,4-d]pyrimidin-4 (5H)-6(7H)-dione (ppX), 2'-deoxypseudoisocytidine (iso dC), 5-fluoro-2'-deoxyuridine (fdU), and 2'-O,4'-C-ethylene bridged nucleic acid (ENA) modifications, and combinations of these modifications. In certain embodiments, the LNA modifications present on the allele-specific blocker probe and/or allele-specific primer are non-consecutive or non-contiguous, such that two LNA bases are not next to each other in the sequence.

In preferred embodiments, the nucleic acid modification that is present on the allele-specific blocker probe and/or allele-specific primer comprises one or more LNA nucleotides. In certain embodiments, the modification is located (a) at the 3'-end, (b) at the 5'-end, (c) at an internal position, or at any combination of (a), (b) or (c) within the allele-specific blocker probe and/or the allele-specific primer. In some preferred embodiments, one modification (e.g., LNA) is located at the allele-specific nucleotide portion of the allele-specific primer, such that this modification comprises the nucleobase used to discriminate between allelic variants. In other preferred embodiments, one modification (e.g., LNA) is located at the allele-specific nucleotide portion of the allele-specific blocker probe, such that this modification comprises the nucleobase used to discriminate between allelic variants. In yet other preferred embodiments, the nucleic acid modifications (e.g., LNA) are not placed in consecutive or contiguous positions of the allele-specific primer and/or blocker probe.

In some embodiments, the nucleic acid modifications present on the allele-specific blocker probe and/or allele-specific primer independently comprise one or more (at least 1, 2, 3, 4, 5, 6, 7, 8, 9, 10, 11, 12, 13, 14, 15, or all) PNA, ZNA, TNA, and/or TzDNA nucleotides.

Other examples of nucleic acid modifications that can be used in the invention are described, e.g., in U.S. Pat. No. 7,517,978, the disclosure of which is incorporated herein by reference in its entirety for all purposes.

Many modified nucleic acid moieties, including, for example, LNA, PNA, ZNA, TNA, TzDNA, ppA, ppG, and 5-Fluoro-dU (fdU), are commercially available and can be used in oligonucleotide synthesis methods well known in the art. In some embodiments, synthesis of modified primers and probes can be carried out using standard chemical means also well known in the art. For example, the modified moiety or base can be introduced by use of (a) a modified nucleoside as a DNA synthesis support, (h) a modified nucleoside as a phosphoramidite, (c) a reagent during DNA synthesis (e.g., benzylamine treatment of a convertible amidite when incorporated into a DNA sequence), or (d) by post-synthetic modification.

In addition, in some embodiments, the nucleotide units which are incorporated into the oligonucleotides of the allele-specific primers and/or allele-specific blocker probes of the present invention may have a cross-linking function (an alkylating agent) covalently bound to one or more of the bases, e.g., through a linking arm.

In yet another aspect, the present invention provides methods for detecting and/or quantitating an allelic variant in a mixed sample. Some of these methods can comprise: (a) hybridizing a first allele-specific primer to a first nucleic acid molecule comprising a first allele (allele-1) in a first reaction mixture and hybridizing a second allele-specific primer to a first nucleic acid molecule comprising a second allele (allele-2) in a second reaction mixture, wherein allele-2 corresponds to the same loci as allele-1; (b) hybridizing a first allele-specific blocker probe to a second nucleic acid molecule comprising allele-2 in the first reaction mixture and hybridizing a second allele-specific blocker probe to a second nucleic acid molecule comprising allele-1 in the second reaction mixture; (c) hybridizing a first detector probe to the first nucleic acid molecule in the first reaction mixture and hybridizing a second detector probe to the first nucleic acid molecule in the second reaction mixture; (d) hybridizing a first locus-specific primer to the extension product of the first allele-specific primer in the first reaction mixture and hybridizing a second locus-specific primer to the extension product of the second allele-specific primer in the second reaction mixture; (e) PCR amplifying the first nucleic acid molecule to form a first set or sample of amplicons and PCR amplifying the second nucleic acid molecule to form a second set or sample of amplicons; and (f) comparing the first set of amplicons to the second set of amplicons to quantitate allele-1 in the sample comprising allele-2 and/or allele-2 in the sample comprising allele-1.

In yet another aspect, the present invention provides methods for detecting a first allelic variant of a target sequence in a nucleic acid sample suspected of comprising at least a second allelic variant of the target sequence. Non-limiting examples of such methods include forming a reaction mixture by combining one or more of the following components: (i) a nucleic acid sample; (ii) an allele-specific primer, wherein an allele-specific nucleotide portion of the allele-specific primer is complementary to the first allelic variant of the target sequence and comprises a nucleic acid modification as described herein; (iii) an allele-specific blocker probe that is complementary to a region of the target sequence comprising the second allelic variant, wherein the region encompasses a position corresponding to the binding position of the allele-specific nucleotide portion of the allele-specific primer, and wherein the allele-specific blocker probe comprises a non-extendable blocking moiety and a nucleic acid modification as described herein; (iv) a locus-specific primer that is complementary to a region of the target sequence that is 3' from the first allelic variant and that is on the opposite strand; and/or (v) a detector probe. In certain instances, the first allelic variant comprises a mutant allele and the second allelic variant comprises the wild-type allele.

Next, an amplification reaction, typically a PCR amplification reaction, is carried out on the reaction mixture using the locus-specific primer and the allele-specific primer to form an amplicon. Then, the amplicon is detected by a change in a detectable property of the detector probe upon binding to the amplicon, thereby detecting the first allelic variant of the target gene in the nucleic acid sample. The detector probe in illustrative embodiments is a 5' nuclease probe and the detectable property in illustrative embodiments is fluorescence.

In some embodiments, the 3' nucleotide position of the 5' target region of the allele-specific primer is an allele-specific nucleotide position. In other embodiments, the allele-specific nucleotide portion of the allele-specific blocker probe is located in the center of the allele-specific blocker probe.

In certain embodiments, the quantity of the first allelic variant is determined by evaluating a change in a detectable property of the detector probe.

In some embodiments, the methods of the invention for detecting an allelic variant in a target sequence in a nucleic acid sample comprises the following cycling protocol:

(a) forming a reaction mixture comprising one or more of the following components:
  (i) a nucleic acid sample;
  (ii) an allele-specific primer, wherein an allele-specific nucleotide portion of the allele-specific primer is complementary to a first allelic variant of the target sequence and comprises a nucleic acid modification at the location of the first allelic variant as described herein;
  (iii) an allele-specific blocker probe that is complementary to a region of the target sequence comprising a second allelic variant, wherein the region encompasses a position corresponding to the binding position of the allele-specific nucleotide portion of the allele-specific primer, and wherein the allele-specific blocker probe comprises a blocking moiety and a nucleic acid modification at the location of the second allelic variant as described herein;
  (iv) a locus-specific primer that is complementary to a region of the target sequence that is 3' from the first allelic variant and on the opposite strand; and
  (v) a detector probe;
(b) PCR amplifying the target sequence using a cycling protocol comprising a number of cycles run at an annealing/extension temperature; and
(c) detecting a change in a detectable property of the detector probe in the amplified products of the target sequence produced by step (b).

There are several major advantages of the methods of the present invention. First, the genotyping assays described herein improve the detection sensitivity by lowering the Ct value for matched targets or alleles. Next, the genotyping assays described herein improve specificity by increasing the ΔCt between Ct values of matched and mismatched sequences. In addition, the genotyping assays described herein improve uniformity of efficiency across various assays.

In other embodiments, the methods of the present invention may include a 2-stage cycling protocol. In some embodiments, the methods for detecting an allelic variant in a target sequence in a nucleic acid sample comprises:

(a) forming a reaction mixture comprising one or more of the following components:
  (i) a nucleic acid sample;
  (ii) an allele-specific primer, wherein an allele-specific nucleotide portion of the allele-specific primer is complementary to a first allelic variant of the target sequence and comprises a nucleic acid modification at the location of the first allelic variant as described herein;
  (iii) an allele-specific blocker probe that is complementary to a region of the target sequence comprising a second allelic variant, wherein the region encompasses a position corresponding to the binding position of the allele-specific nucleotide portion of the allele-specific primer, and wherein the allele-specific blocker probe comprises a blocking moiety and a nucleic acid modification at the location of the second allelic variant as described herein;
  (iv) a locus-specific primer that is complementary to a region of the target sequence that is 3' from the first allelic variant and on the opposite strand; and
  (v) a detector probe;
(b) PCR amplifying the target sequence using a 2-stage cycling protocol comprising:

(i) a first amplification step comprising a first number of cycles run at a first annealing/extension temperature; and (ii) a second amplification step comprising a second number of cycles run at a second annealing/extension temperature; and (c) detecting a change in a detectable property of the detector probe in the amplified products of the target sequence produced by step (b).

In some instances, the first number of cycles in step (b) is fewer than the second number of cycles and the first annealing/extension temperature is lower than the second annealing/extension temperature. In some embodiments, the number of cycles used in the first stage of the cycling protocol is about 2%-20%, 4%-18%, 6%-16%, 8%-14%, 10%-12%, or any percent in between, of the total number of cycles used in the second stage. In other embodiments, the first stage employs between about 1 to 10 cycles, 2 to 8 cycles, 3 to 7 cycles, 4 to 6 cycles, or any number of cycles in between, e.g., 2, 3, 4, 5, 6, or 7 cycles.

In some embodiments, the number of cycles used in the second stage of the cycling protocol is about 5 times, 6 times, 8 times, 10 times, 12 times, 18 times, 25 times, 30 times, 35 times, 40 times, 45 times, 50 times the number of cycles used in the first stage. In some embodiments, the second stage employs between about 30 to 50 cycles, 35 to 48 cycles, 40 to 46 cycles, or any number of cycles in between, e.g., 35, 36, 37, 38, 39, 40, 41, 42, 43, 44, 45, or 46 cycles.

In some embodiments, the lower annealing/extension temperature used during the first cycling stage is about 1° C., about 2° C., about 3° C., about 4° C., or about 5° C. lower than the annealing/extension temperature used during the second cycling stage. In some instances, the annealing/extension temperature of the first stage is between about 50° C. to 60° C., 52° C. to 58° C., or 54° C. to 56° C., e.g., 53° C., 54° C., 55° C., or 55° C. In certain other embodiments, the annealing/extension temperature of the second stage is between about 56° C. to 66° C., 58° C. to 64° C., or 60° C. to 62° C., e.g., 58° C., 60° C., 62° C., or 64° C.

In another aspect, the present invention provides a reaction mixture that comprises the following components: (i) a nucleic acid molecule; (ii) an allele-specific primer, wherein an allele-specific nucleotide portion of the allele-specific primer is complementary to a first allelic variant of a target sequence and comprises a nucleic acid modification; (iii) an allele-specific blocker probe, wherein an allele-specific nucleotide portion of the allele-specific blocker probe is complementary to a second allelic variant of the target sequence and comprises a nucleic acid modification, and wherein the allele-specific blocker probe comprises a blocker moiety at the 3'-end of the oligonucleotide sequence; (iv) a locus-specific primer that is complementary to a region of the target sequence that is 3' from the first allelic variant and on the opposite strand; and/or (v) a detector probe.

In some embodiments, the methods of the present invention are used to detect a first allelic variant that is present at a frequency of less than about 1/10, 1/100, 1/1,000, 1/10,000, 1/100,000, 1/1,000,000, 1/10,000,000, 1/100,000,000 or 1/1,000,000,000, and any fractional ranges in between, of a second allelic variant for a given SNP or gene. In other embodiments, the methods of the present invention are used to detect a first allelic variant that is present in less than about 2, 3, 4, 5, 6, 7, 8, 9, 10, 15, 20, 25, 30, 35, 40, 45, 50, 75, 100, 250, 500, 750, 1,000, 2,500, 5,000, 7,500, 10,000, 25,000, 50,000, 75,000, 100,000, 250,000, 500,000, 750,000, or 1,000,000 copies per 1, 10, 300, 500, or 1,000 micro liters, and any fractional ranges in between, of a sample or a reaction volume.

In certain embodiments, the first allelic variant is a mutant allele and the second allelic variant is a wild-type allele. In some embodiments, the present methods can involve detecting one mutant molecule in a background of at least about 1,000 to 1,000,000, such as about 1,000 to 10,000, about 10,000 to 100,000, or about 100,000 to 1,000,000 wild-type molecules, or any fractional ranges in between. In some embodiments, the methods can provide high sensitivity and efficiency that is at least comparable to TaqMan®-based assays.

In another aspect, the present invention provides kits for quantitating a first allelic variant in a sample comprising an alternative second allelic variant that include: (a) an allele-specific primer; (b) an allele-specific blocker probe; (c) a locus-specific primer; (d) a detector probe; and/or (e) a polymerase.

In yet another aspect, the present invention provides kits comprising two or more containers comprising the following components independently distributed in one of the two or more containers: (i) an allele-specific primer, wherein an allele-specific nucleotide portion of the allele-specific primer is complementary to a first allelic variant of a target sequence and comprises a nucleic acid modification as described herein; and (ii) an allele-specific blocker probe that is complementary to a region of the target sequence comprising a second allelic variant, wherein the region encompasses a position corresponding to the binding position of the allele-specific nucleotide portion of the allele-specific primer, and wherein the allele-specific blocker probe comprises a non-extendable blocker moiety and a nucleic acid modification as described herein. In particular embodiments, the allele-specific blocker probe comprises an allele-specific nucleotide portion that is complementary to a second allelic variant of the target sequence, wherein the allele-specific nucleotide portion comprises a nucleic acid modification, and wherein the allele-specific blocker probe comprises a blocker moiety at the 3'-end of the oligonucleotide sequence.

In some embodiments, the kits can further comprise a locus-specific primer that is complementary to a region of the target sequence that is 3' from the first allelic variant and that is on the opposite strand. In other embodiments, the kits can further comprise a detector probe. In yet other embodiments, the kits can further comprise additional components used for pre-amplification.

In some embodiments, the compositions, methods, and/or kits of the invention are useful for detecting tumor cells in samples such as blood or fine needle aspirates (FNA) for early cancer diagnosis. In other embodiments, the compositions, methods, and/or kits of the invention are useful for cancer or disease-associated genetic variation or somatic mutation detection and validation. In yet other embodiments, the compositions, methods, and/or kits can be used for genotyping di-allelic, tri-allelic, or tetra-allelic SNPs. In other embodiments, the compositions, methods, and/or kits of the invention can be used for identifying single or multiple nucleotide insertion or deletion mutations. In some embodiments, the compositions, methods, and/or kits of the invention can be used for DNA typing from mixed DNA samples for QC and human identification assays, cell line QC for cell contaminations, allelic gene expression analysis, virus typing/rare pathogen detection, mutation detection from pooled samples, detection of circulating tumor cells in blood, and/or prenatal diagnostics.

B. Allele-Specific Primers

In some embodiments, the allele-specific primers are short oligomers ranging from about 15-30, such as about 16-28, about 17-26, about 18-24, or about 20-22, or any range in between, nucleotides in length. In some embodiments, the Tm of the allele-specific primers range from about 50° C. to 70° C., such as about 52° C. to 68° C., about 54° C. to 66° C., about 56° C. to 64° C., about 58° C. to 62° C., or any temperature in between (e.g., 53° C., 54° C., 55° C., 56° C.). In other embodiments, the Tm of the allele-specific primers is about 3° C. to 6° C. higher than the anneal/extend temperature of the PCR cycling conditions employed during amplification. In certain instances, allele-specific primers designed with low Tm's increase discrimination of allelic variants.

In some embodiments of the invention, low allele-specific primer concentration improves selectivity. In certain instances, a reduction in concentration of allele-specific primers below 900 nM increases the delta Ct between matched and mismatched sequences. In some embodiments, the concentration of allele-specific primers ranges from about 20 nM to 900 nM, such as about 50 nM to 700 nM, about 100 nM to 500 nM, about 200 nM to 400 nM, about 200 nM to 300 nM, about 400 nM to 500 nM, or any range in between.

In some embodiments, the allele-specific primers of the invention can comprise an allele-specific nucleotide portion that is specific to the target allele of interest. The allele-specific nucleotide portion of an allele-specific primer is complementary to one allele of a gene, but not another allele of the gene. In other words, the allele-specific nucleotide portion binds to one or more variable nucleotide positions of a gene that are nucleotide positions that are known to include different nucleotides for different allelic variants of a gene. The allele-specific nucleotide portion is at least one nucleotide in length. In exemplary embodiments, the allele-specific nucleotide portion is one nucleotide in length. In some embodiments, the allele-specific nucleotide portion of an allele-specific primer is located at the 3' terminus of the allele-specific primer. In other embodiments, the allele-specific nucleotide portion is located about 1-2, 3-4, 5-6, 7-8, 9-11, 12-15, or 16-20 nucleotides in from the 3' most-end of the allele-specific primer.

Allele-specific primers designed to target discriminating bases can also improve discrimination of allelic variants. In some embodiments, the nucleotide of the allele-specific nucleotide portion targets a highly discriminating base (e.g., for detection of A/A, A/G, G/A, G/G, A/C, or C/A alleles). Less discriminating bases, for example, may involve detection of C/C, T/C, G/T, T/G, C/T alleles. In some embodiments, for example, when the allele to be detected involves A/G or C/T SNPs, A or G may be used as the 3' allele-specific nucleotide portion of the allele-specific primer (e.g., if A or T is the major allele), or C or T may be used as the 3' allele-specific nucleotide portion of the allele-specific primer (e.g., if C or G is the major allele). In other embodiments, A may be used as the nucleotide-specific portion at the 3' end of the allele specific primer (e.g., the allele-specific nucleotide portion) when detecting and/or quantifying A/T SNPs. In yet other embodiments, G may be used as the nucleotide-specific portion at the 3' end of the allele specific primer when detecting and/or quantifying C/G SNPs.

In some embodiments, the allele-specific primer can comprise a target-specific portion that is specific to the polynucleotide sequence (or locus) of interest. In other embodiments, the target-specific portion is about 75-85%, 85-95%, 95-99%, or 100% complementary to the target polynucleotide sequence of interest. In some embodiments, the target-specific portion of the allele-specific primer can comprise the allele-specific nucleotide portion. In other embodiments, the target-specific portion is located 5' to the allele-specific nucleotide portion. The target-specific portion can be about 4-30, about 5-25, about 6-20, about 7-15, or about 8-10 nucleotides in length. In some embodiments, the Tm of the target specific portion is about 5° C. below the anneal/extend temperature used for PCR cycling. In some embodiments, the Tm of the target specific portion of the allele-specific primer ranges from about 53° C. to 60° C., about 52° C. to 59° C., about 53° C. to 58° C., about 54° C. to 57° C., about 55° C. to 56° C., or about 50° C. to about 60° C.

In embodiments where two allele-specific primers are used, the target-specific portion of the first allele-specific primer and the target-specific portion of the second allele-specific primer comprise the same sequence or are the same sequence.

In some embodiments, the allele-specific primer can comprise one or more modified nucleobases or nucleosidic bases different from the naturally occurring bases (i.e., adenine, cytosine, guanine, thymine and uracil). In some embodiments, the modified bases are still able to effectively hybridize to nucleic acid units that contain adenine, guanine, cytosine, uracil or thymine moieties. In some embodiments, the modified base(s) may increase the difference in the Tm between matched and mismatched target sequences and/or decrease mismatch priming efficiency, thereby improving assay specificity, selectivity and reproducibility. In some embodiments, the modified base(s) may increase the binding affinity of the allele-specific primer towards its complementary DNA target.

In particular embodiments, the allele-specific primer comprises at least one, two, or more modified bases. Examples of modified bases include, without limitation, locked nucleic acid (LNA), peptide nucleic acid (PNA), threose nucleic acid (TNA), zip nucleic acid (ZNA) and triazole DNA (TzDNA), 8-aza-7-deaza-dA (ppA), 8-aza-7-deaza-dG (ppG), 2'-deoxypseudoisocytidine (iso dC), deoxyuridine (fdU), 2'-O,4'-C-ethylene bridged nucleic acid (ENA) bases, and combinations thereof.

In some embodiments, the allele-specific primer comprises 2 to 6 LNAs, PNAs, TNAs, ZNAs or ribose modified nucleic acids. These modified bases exhibit thermal stability towards complementary DNA and RNA, which allows for excellent mismatch discrimination in methods of the present invention. The high binding affinity of these modified bases can be used in hybridization assays that require high specificity, selectivity and/or reproducibility.

In some embodiments, the modified base present on the allele-specific primer comprises one or more LNA modifications. In these embodiments, LNA modifications are not placed in consecutive positions on the allele-specific primer. In certain embodiments, the modified base is located (a) at the 3'-end, (b) at the 5'-end, (c) at an internal position, or at any combination of (a), (h) or (c) within the allele-specific primer. In some embodiments, the modified base (e.g., LNA nucleoside) is located at the allele-specific nucleotide portion of the allele-specific primer, such that the LNA nucleoside comprises the nucleobase used to discriminate between allelic variants.

In preferred embodiments, a LNA modification is located at the 3' end of the allele-specific primer. With the LNA at the allelic variant at the 3' end, the melting temperature (Tm) of the allele-specific primer increases, thereby enhancing the selectivity of the assay of the present invention towards the allelic variant. In addition, selective amplification of the allelic variant can occur at a higher amplification temperature during PCR cycling. In some instances, the presence of the LNA at the 3'-end may also help slow down the proofreading exonuclease activity of DNA polymerase. In other instances, the presence of the LNA at the penultimate positions may provide protection against 3'→5' exonuclease activity of DNA polymerase (see, e.g., Giusto, D and King, G, *Nucleic Acids Res.*, 32:3, e 32, 1-8 (2004)).

In some embodiments, a plurality of LNAs are present in the primer and are spaced anywhere between 5 to 10 bases from the 3'-end. In other embodiments, the primer can contain 1, 2, 3, 4, 5, 6, 7, 8, 9, 10, or 11 LNAs spaced anywhere between 2, 3, 4, 5, 6, 7, 8, 9, or 10 bases from the 3'-end. In yet other embodiments, a LNA modification is positioned at the penultimate position relative to the 3' end of the primer, at the 3'-end, at the 5'-end, and combinations thereof. In these embodiments, LNA modifications are typically not placed in consecutive positions of the primer sequence.

LNA modifications in the oligonucleotide increases the binding affinity towards the complementary DNA target. The higher affinity is affiliated to the reduced conformational flexibility of the locked 3'-endo conformation of the ribose. Like DNA bases, LNA bases are linked in by the same phosphate backbone allowing the LNA-DNA primer to bind efficiently to its complementary DNA, thus resulting in a higher Tm of the duplex. The discriminatory effect dependents on the ability of primer binding to the genomic DNA and staying bound during PCR cycling. This is achieved due to the high binding affinity of the LNA-DNA primer. The higher Tm of the LNA-DNA duplex correlates to its better binding affinity. Allele-specific primers with LNA allow for higher reaction temperatures during PCR cycling, which enhances the specificity of the genotyping assay, compared to non-LNA primers with a lower Tm.

In some embodiments, the allele-specific primer, blocker probe and/or detector probe comprises PNA modifications. PNA modifications on an allele-specific primer offers high specificity and sensitivity to its DNA target. The higher binding affinity and higher Tm of PNA offers high specificity and reproducibility to the methods described herein.

It is appreciated by those skilled in the art that a PNA-DNA duplex binds with greater strength, higher stability, more quickly and more specificity compared to a DNA-DNA duplex, due to the lack of electrostatic repulsion between a PNA strand and DNA strand. The greater stability is reflected by a higher Tm for a PNA-duplex versus the analogous DNA-DNA duplex. PNA complexes are more thermally stable and less susceptible to degradation by nucleases, proteases and peptidases. It has been shown that the Tm of PNA-DNA duplexes is in part independent of salt concentration. In some embodiments, an allele-specific primer and/or blocker probe with a PNA can bind its nucleic acid target in the absence of salt despite the presence of secondary structure. See, e.g., Nielsen, P. E. and Egholm, M., *Current Issues Molec. Biol.* 1; 89-104 (1999); Gaylord et al., *Proc. Natl. Acad. Sci.*, 102: 34-39 (2005)), the disclosures of each of which are incorporated herein by reference in their entireties for all purposes.

In some embodiments, the allele-specific primer comprises one or a plurality of zip nucleic acid (ZNA) molecules. A ZNA primer has increased affinity for its complementary target DNA due to decreased electrostatic repulsion between the nucleic acid strands. The presence of one or a plurality of ZNA modifications on the allele-specific primer can increase the Tm of the ZNA-DNA duplex and improve allelic discrimination in methods of the present invention.

In some embodiments, the allele-specific primer comprises one or a plurality of (3'-2') α-L-threose nucleic acids (TNAs). TNA can hybridize strongly with DNA and is a good mimic of the A-form of DNA and of RNA. Due to the increased stability of a TNA-DNA duplex compared to analogous DNA-DNA complexes, using a TNA allele-specific primer in methods of the present invention can improve mismatch discrimination of allelic variants.

In other embodiments, the allele-specific primer comprises one or a plurality of triazole linked DNA (TzDNA) molecules. Since TzDNA has increase thermal stability towards matched its DNA target compared to analogous DNA primer, TzDNA allele-specific primers can be used in methods of the present invention for improved allelic variant discrimination.

In some embodiments, the allele-specific primer comprises a tail. In some instances, allele-specific primers comprising tails enable the overall length of the primer to be reduced, thereby lowering the Tm without significant impact on assay sensitivity. In some instances, the tail is on the 5' terminus of the allele-specific primer. In other instances, the tail is located 5' of the target-specific portion and/or allele-specific nucleotide portion of the allele-specific primer. In some embodiments, the tail is about 65-75%, about 75-85%, about 85-95%, about 95-99% or about 100% non-complementary to the target polynucleotide sequence of interest. In some embodiments, the tail can be about 2-40, such as about 4-30, about 5-25, about 6-20, about 7-15, or about 8-10 nucleotides in length. In some embodiments, the tail is GC-rich. For example, in some embodiments, the tail sequence is comprised of about 50-100%, about 60-100%, about 70-100%, about 80-100%, about 90-100% or about 95-100% G and/or C nucleotides.

The tail of the allele-specific primer may be configured in a number of different ways, including, but not limited to, a configuration whereby the tail region is available after primer extension to hybridize to a complementary sequence (if present) in a primer extension product. As a non-limiting example, the tail of the allele-specific primer can hybridize to the complementary sequence in an extension product resulting from extension of a locus-specific primer.

In embodiments where two allele-specific primers are used, the tail of the first allele-specific primer and the tail of the second allele-specific primer comprise the same sequence or are the same sequence.

C. Allele-Specific Blocker Probes

In some embodiments, the allele-specific blocker probe of the present invention is specifically designed to hybridize to the a first allele and inhibit the amplification of the first allele efficiently and selectively, without affecting the amplification of the second variant. In some aspects of the present invention, the blocker probe is specifically designed to hybridize to the wild-type allele and inhibit its amplification, without affecting the amplification of the mutant allele.

Allele-specific blocker probes may be designed as short oligomers that are single-stranded and have a length of about 100 nucleotides or less, about 50 nucleotides or less, about 30 nucleotides or less, about 20 nucleotides or less, or about 5-20 nucleotides.

In some embodiments, the Tm of the blocker probes range from 58° C. to 70° C., 61° C. to 69° C., 62° C. to 68° C., 63° C. to 67° C., 64° C. to 66° C., or about 60° C. to about 63° C., or any range in between. In yet other embodiments, the Tm of the allele-specific blocker probes is about 3° C. to 6°

C. higher than the anneal/extend temperature in the PCR cycling conditions employed during amplification.

In some embodiments, the blocker probes are not cleaved during PCR amplification. In some embodiments, the blocker probes comprise a non-extendable blocker moiety at their 3'-ends. In other embodiments, the blocker probes further comprise other moieties including, but not limited to, additional non-extendable blocker moieties, quencher moieties, fluorescent moieties, etc. at their 3'-end, 5'-end, and/or any internal position in between. In certain other embodiments, the allele position is located about 5-15, such as about 5-11, about 6-10, about 7-9, about 7-12, or about 9-11, such as about 6, about 7, about 8, about 9, about 10, or about 11 nucleotides away from the non-extendable blocker moiety of the allele-specific blocker probes when hybridized to their target sequences. In some embodiments, the non-extendable blocker moiety can include, without limitation, an optionally substituted $C_1$-$C_{24}$ alkyl diol (e.g., a 3'-hexanediol modification), an optionally substituted $C_2$-$C_{24}$ alkenyl diol or $C_2$-$C_{24}$ alkynyl diol a minor groove binder (MGB), an amine ($NH_2$), biotin, PEG, $PO_4$, and mixtures thereof. As disclosed herein, the use of non-extendable blocker moieties such as, e.g., 3'-hexanediol modifications in allele-specific blocker probes can increase the specificity of allele-specific PCR. Suitable methods for conjugating non-extendable blocker moieties to allele-specific blocker probes are known to one of ordinary skill in the art. For example, a blocker moiety comprising a $C_1$-$C_{24}$ alkyl diol (e.g., hexanediol) can be conjugated to the 3'-end of an allele-specific blocker probe via a phosphoramidite linkage.

In some aspects, the blocker probe with hexanediol modification performs better than one with phosphorylation. The flexibility and the hydrophobicity of the carbon chain allows the blocker to hybridize to its wild-type target without being sterically hindered. Although the phosphate group at the 3' end binds to the target wild-type sequence, efficiency may be diminished by the bulkiness and the ionic nature of the phosphate group.

In certain embodiments, the non-extendable blocker moiety does not comprise or include a minor groove binder (MGB). In certain other embodiments, the non-extendable blocker moiety does not comprise or include a $PO_4$ group. In further embodiments, the non-extendable blocker moiety consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In some embodiments, the blocker probe has a dideoxycytidine (ddC) moiety, which is a 3' chain terminator that prevents 3' extension by DNA polymerases.

In some embodiments, the allele-specific blocker probe can comprise one or more modified nucleobases or nucleosidic bases different from the naturally occurring bases (i.e., adenine, cytosine, guanine, thymine and uracil). In some embodiments, the modified bases are still able to effectively hybridize to nucleic acid units that contain adenine, guanine, cytosine, uracil or thymine moieties. In some embodiments, the modified base(s) may increase the difference in the Tm between matched and mismatched target sequences and/or decrease mismatch priming efficiency, thereby improving assay specificity and selectivity.

It is appreciated by those in the art that the mismatch discrimination ability of a probe relies upon the difference in melting temperatures (ΔTm) between matched and mismatched probe-target duplexes. ΔTm typically increases when the probe size decreases because the mismatch has a more destabilizing effect on the duplex. In general, allele-specific probes that are better at discriminating matched and mismatched sequences have greater ΔTm values.

In particular embodiments, the allele-specific blocker probe of the present invention comprises at least one, two, or more modified bases. Non-limiting examples of modified bases include locked nucleic acid (LNA), 8-aza-7-deaza-dA (ppA), 8-aza-7-deaza-dG (ppG), 2'-deoxypseudoisocytidine (iso dC), 5-fluoro-2'-deoxyuridine 2'-O,4'-C-ethylene bridged nucleic acid (ENA) bases, and combinations thereof. In preferred embodiments, the modified base present on the allele-specific blocker probe comprises one or more LNA modifications. In certain embodiments, the modified base is located (a) at the 3'-end, (b) at the 5'-end, (c) at an internal position, or at any combination of (a), (b) or (c) within the allele-specific blocker probe. In some preferred embodiments, the modified base (e.g., LNA nucleoside) is located at the allele-specific nucleotide portion of the allele-specific blocker probe, such that the LNA nucleoside comprises the nucleobase used to discriminate between allelic variants.

In some embodiments, the inhibitory effect of the blocker probe increases as the Tm of the blocker probe increases. Depending on the position of the LNA in the blocker, the Tm can increase by 1-8° C. (see, e.g., Koshkin et al., *Tetrahedron*, 54: 3607-3630 (1998), Obika et al., *Tetrahedron Lett.*, 39: 5401-5404 (1998), Wang et al., *Bioorg. Med. Chem. Lett.*, 9: 1147-1150 (1999)). A blocker with higher Tm can remain annealed to the wild-type allele during extension, thereby inhibiting efficient PCR amplification. Kinetic studies of duplex formation have shown that LNA-containing DNA duplexes have a slower dissociation rate compared to duplexes of native DNA. It has also been shown that the rigid structure of LNA affects its interactions with Taq DNA polymerase (Larotta et al., *Molecular and Cellular Probes*, 17: 253-259 (2003)).

In some aspects of the present invention, the blocker probe can possess one or a plurality of LNA modifications. In some embodiments, LNA is placed at the mid-position of the blocker sequence, the penultimate position, the 5' end, different intervals of the blocker sequence, and/or combinations thereof. In some embodiments, LNA is placed at the variant nucleotide complementary to the wild-type variant. In other embodiments, a blocker probe does not contain consecutive LNAs.

In embodiments where two allele-specific blocker probes are used, the first allele-specific blocker probe binds to the same strand or sequence as the first allele-specific primer, while the second allele-specific blocker probe binds to the opposite strand or complementary sequence as the first allele-specific primer.

In some embodiments, the allele-specific primer and the blocker probe both comprise LNA. The presence of the modified base on both the primer and the blocker probe enhances the specificity of the assay of the present invention. It has been shown in kinetic studies of duplex formation that the slower dissociation rate of LNA-containing complexes is due to differences in its hybridization performance as compared to that of native DNA. The rigid structure of LNA molecule could alter the way it interacts with Taq DNA polymerase (Larotta et al., *Mol. Cell. Probes*, 17: 253-259 (2003)).

D. Detector Probes

In some aspects, the methods of the present invention require the use of a short detector probe length with a high melting temperature. Shorter length probes with high Tm are necessary for good allelic discrimination, especially when dealing with difficult mutations such as G→A or G→T.

Examples of detector probes include, but are not limited to, minor grove binding (MGB) probes, Zen probes (IDT, Coralville, Iowa), zip nucleic acid (ZNA) probes, and protein nucleic acid (PNA) probes.

In some embodiments, the detector probe is designed as short oligomers ranging from about 15-30 nucleotides, such as about 16, about 18, about 22, about 24, about 30, or any number in between. In some embodiments, the Tm of the detector probe ranges from about 60° C. to 70° C., about 61° C. to 69° C., about 62° C. to 68° C., about 63° C. to 67° C., about 64° C. to 66° C., or any temperature in between.

In some embodiments, the detector probe is a locus-specific detector probe (LST). In other embodiments, the detector probe is a 5' nuclease probe. In some embodiments, the detector probe can comprises an MGB moiety, a reporter moiety (e.g., FAM™, TET™, JOE™, VIC™, or SYBR® Green), a quencher moiety (e.g., Black Hole Quencher™ or TAMRA™), and/or a passive reference (e.g., ROX™). In some exemplary embodiments, the detector probe is designed according to the methods and principles described in U.S. Pat. No. 6,727,356, the disclosure of which is incorporated herein by reference in its entirety for all purposes.

In particular embodiments, the detector probe is a Taq-Man® probe (Applied Biosystems, Foster City, Calif.). Taqman probes are designed with MGB ligands (see, e.g., Afonina et al., *Nucleic Acid Res.*, 25:2657-2660 (1997)) to help the probe to form super stabilized duplexes with its complementary DNA target. The increased stability of the duplexes is associated with a higher Tm. For example, the Tm (65° C.) of a 12-mer Taqman probe with MGB is almost identical to the Tm (66° C.) of 27-mer DNA probe without MGB. It has been shown that with shorter probes, MGB contributes more to the overall stability of the probe. It has been shown that 3'-MGB DNA probes increase sequence specificity during PCR cycling (Kutyavin et al., *Nucleic Acid Res.*, 28:655-661 (2000)). MGB probes of the present invention are designed to detect a genomic sequence either specific to the allelic variant, near the allelic variant, or away from the allelic variant. For instance, the MGB probe can detect the 3' end of the amplification product generated by PCR cycling using an allele-specific primer and a blocker probe.

In other embodiments, the detector probe is a Zen probe (IDT, Coralville, Iowa). A ZEN double-quenched probe comprise an oligonucleotide probe, a 5' FAM fluorophore, a 3' IBFq quencher and an internal ZEN quencher. The ZEN quencher lowers background and generates higher signal compared to traditional dye-quencher probes (e.g., 5' FAM-3' TAMRA, 5' FAM-3' IBFQ, 5' FAM-3' Eclipse, 5' FAM-3' BHQ-1). The internal ZEN quencher decreases the length between the dye and quencher to only 9 base pairs which significantly reduces background fluorescence and provides more thorough quenching. The sensitivity of the ZEN probe increases as the endpoint signal increases and the Ct (threshold cycle; the fractional cycle number where fluorescence increases above the threshold) values reduce.

In yet other embodiments, the detector probe comprises one or a plurality of zip nucleic acid (ZNA) and/or peptide nucleic acid (PNA) modifications. Due to the increase stability of the cationic charges of a ZNA probe, methods of the present invention can comprise short dual-labeled ZNA probes. ZNA probes have enhanced target recognition, greater sensitivity, high specificity, and increased Tm over standard detector probes. In another embodiment, the detector probe is a PNA probe. Short PNA probes of the present invention can offer high specificity because a PNA modification affords a high level of discrimination at the single base level.

In some embodiments, the detector probe uses oligonucleotides with modified bases or nucleic acid analogs comprising 2 to 6 LNAs, PNAs, TNAs, ZNAs or ribose modified nucleic acids. These modified bases exhibit thermal stability towards complementary DNA and RNA, which allows for excellent mismatch discrimination in methods of the present invention.

In other embodiments, the locus-specific detector probe is designed according to the principles and methods described in U.S. Pat. No. 6,727,356, the disclosure of which is incorporated herein by reference in its entirety for all purposes. For example, fluorogenic probes can be prepared with a quencher at the 3' terminus of a single DNA strand and a fluorophore at the 5' terminus. In such an example, the 5'-nuclease activity of a Taq DNA polymerase can cleave the DNA strand, thereby separating the fluorophore from the quencher and releasing the fluorescent signal. In some embodiments, the detector probes are hybridized to the template strands during primer extension step of PCR amplification (e.g., at 60°-65° C.). In other embodiments, an MGB is covalently attached to the quencher moiety of the locus-specific detector probes (e.g., through a linker).

In embodiments where two detector probes are used, the first and second detector probes are the same and/or comprise the same sequence or are the same sequence.

E. Locus-Specific Primers

In some embodiments, the locus-specific primer is designed as a short oligomer ranging from about 15-30 nucleotides, such as about 16, about 18, about 22, about 24, about 30, or any number in between. In some embodiments, the Tm of the locus-specific primer ranges from about 60° C. to 70° C., about 61° C. to 69° C., about 62° C. to 68° C., about 63° C. to 67° C., or about 64° C. to 66° C., or any range in between.

In embodiments where two locus-specific primers are used, the first locus-specific primer and/or the second locus-specific primer comprise the same sequence or are the same sequence.

F. Additional Components

Polymerase enzymes suitable for the practice of the present invention are well known in the art and can be derived from a number of sources. Thermostable polymerases may be obtained, for example, from a variety of thermophilic bacteria that are commercially available (for example, from American Type Culture Collection, Rockville, Md.) using methods that are well-known to one of ordinary skill in the art. See, e.g., U.S. Pat. No. 6,245,533. Bacterial cells may be grown according to standard microbiological techniques, using culture media and incubation conditions suitable for growing active cultures of the particular species that are well-known to one of ordinary skill in the art. See, e.g., Brock et al., *J. Bacterid.*, 98(1):289-297 (1969); Oshima et al., *Int. J. Syst. Bacteria*, 24(1):102-112 (1974). Suitable for use as sources of thermostable polymerases are the thermophilic bacteria *Thermus aquaticus, Thermus thermophilus, Thermococcus litoralis, Pyrococcus furiosus, Pyrococcus woosii* and other species of the *Pyrococcus* genus, *Bacillus stearothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants of each of these species. Preferable thermostable polymerases can include, but are not limited to, Taq DNA polymerase, Tne DNA polymerase, Tma DNA polymerase, or mutants, derivatives, or fragments thereof.

G. Quantitation of Allelic Variants

In certain aspects, the methods of quantitating an allelic variant of a target sequence in a nucleic acid sample comprise determining an amount and/or a percentage of the allelic variant present in the sample using a standard curve established from a cell line positive for the allelic variant. In particular embodiments, the amount of DNA (e.g., amount of nucleic acid carrying the allelic variant) present in the sample is calculated (e.g., in nanogram (ng) or any other unit of weight) from the standard curve using the Ct value. In some instances, the standard curve is based on the cell line carrying a 100% mutation for the allelic variant. In other instances, the amount of DNA derived from the standard curve (e.g., amount of nucleic acid carrying the allelic variant in the sample) is converted to a percent mutation of the allelic variant based on the cell line.

The assays of the present invention have high selectivity and can differentiate and quantitate a rare variant allele from the wild-type allele. The data from the assays are also linear and can be used to derive quantitative information of the allelic variant, e.g., to detect, determine, or calculate the amount or percentage of the allelic variant present in a sample.

In some aspects, a standard curve is generated for an allelic variant from a cell line positive for the variant. In some embodiments, a standard curve is generated for KRAS allelic variants from the following positive cell lines: G12A from the SW1116 cell line; G12C from the NCI-H23 cell line; G12D from the LS 174T cell line; G12R from the PSN1 cell line; G12S from the A 549 cell line; G12V from the SW 403 cell line; G13C from the H 1734 cell line G13D from the T 84 cell line; and/or Q61H from the H 460 cell line. In other embodiments, a standard curve is generated for PIK3CA allelic variants from the following positive cell lines: E542K from the SW948 cell line; E545D from the Sup T1 cell line; E545K from the MCF 7 cell line; and/or H1047R from the KPL4 cell line. In yet other embodiments, a standard curve is generated for EGFR allelic variants from the following positive cell lines: T790M and L858R from the H1975 cell line and/or E746-A750 deletion (E746 del) from the H1650 cell line. In yet other embodiments, a standard curve is generated for the BRAF V600E variant from the HT 29 cell line. In some instances, a standard curve is created from performing the assays of the invention on a series of dilution of DNA (e.g., 100, 10, 1, 0.1, and/or 0.01 ng) from the positive cell line.

In other aspects, the methods of quantitating an allelic variant of a target sequence in a nucleic acid sample comprise determining an amount and/or a percentage of the allelic variant present in the sample using a calculator based on a standard curve established from a cell line positive for the allelic variant. In certain embodiments, a percent mutation calculator specific to an allelic variant is established from the standard curve of the allelic variant. The calculator can be used to calculate the amount of mutation in a nucleic acid sample from the Ct value obtained from the methods of the invention. In some instances, the percent mutation of the allelic variant can be calculated based on the assumption that the positive cell line has a percent mutation of 100% for the allelic variant.

In particular embodiments, the amount or percentage of an allelic variant present in a sample can be quantitated by determining a Ct value obtained when the genotyping assay described herein is performed on nucleic acid obtained from the sample. A standard curve for the allelic variant can be generated by performing the genotyping assay described herein on a serial dilution of nucleic acid sample from a cell line positive for the allelic variant. The standard curve can then be used to determine a Ct value for a specific amount of nucleic acid present in the positive control (e.g., cell line) sample. The standard curve can also be used to determine the line slope and/or line intercept values when Ct values obtained for the positive control samples are plotted as a function of the quantity of DNA per positive control reaction.

FIGS. 32-35 provide non-limiting examples of standard curve plots (e.g., for the positive control samples), amplification curves (e.g., for unknown (test) and positive control samples), and calculators for quantitating the amount and the percent (e.g., percent mutation) of the alleleic variant present in a sample based upon information obtained from the standard and/or amplification curves. In certain embodiments, the percent mutation is calculated from the amount of mutation with respect to the starting amount of nucleic acid (e.g., DNA) in the sample. The starting amount of nucleic acid (e.g., DNA) in the sample can be expressed as a $\log_{10}$ value (e.g., in nanograms). In other embodiments, the calculator quantitates the amount and/or the percent (e.g., percent mutation) of the allelic variant present in a sample based upon information such as Ct values, line slope values, and/or line intercept values that are obtained from the standard and/or amplification curves generated using the genotyping assay described herein. In further embodiments, the percent mutation calculated for an allelic variant present in an unknown (test) sample is relative to the positive control (e.g., compared to the positive cell line with a percent mutation of 100% for the allelic variant).

IV. Exemplary Embodiments

In one aspect, the present invention provides a method for detecting or quantitating a first allelic variant of a target sequence in a nucleic acid sample suspected of having at least a second allelic variant of the target sequence, said method comprising:
  (a) forming a reaction mixture by combining:
    (i) the nucleic acid sample;
    (ii) an allele-specific primer, wherein an allele-specific nucleotide portion of the allele-specific primer is complementary to the first allelic variant of the target sequence, and wherein the allele-specific primer comprises at least one nucleic acid modification (e.g., one or a plurality of nucleic acid modifications);
    (iii) an allele-specific blocker probe that is complementary to a region of the target sequence comprising the second allelic variant, wherein the allele-specific blocker probe comprises a non-extendable blocker moiety and at least one nucleic acid modification (e.g., one or a plurality of nucleic acid modifications);
    (iv) a detector probe; and
    (v) a locus-specific primer that is complementary to a region of the target sequence that is 3' from the first allelic variant and on the opposite strand; and
  (b) carrying out an amplification reaction on the reaction mixture using the locus-specific primer and the allele-specific primer to form an amplicon; and
  (c) detecting the amplicon by detecting a change in a detectable property of the detector probe, thereby detecting the first allelic variant of the target gene in the nucleic acid sample.

In some embodiments, the nucleic acid modification(s) in the allele-specific primer is/are located at the allele-specific nucleotide portion, at the 5'-end of the allele-specific primer, and/or at the 3'-end of the allele-specific primer. In certain embodiments, the allele-specific primer comprises two or more non-consecutive nucleic acid modifications. In some embodiments, the nucleic acid modification(s) in the allele-specific primer is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In other embodiments, the nucleic acid modification(s) in the allele-specific blocker probe is/are located at the allele-specific nucleotide portion and/or at an internal position in the allele-specific blocker probe. In certain embodiments, the allele-specific blocker probe comprises two or more non-consecutive nucleic acid modifications. In some instances, the nucleic acid modification(s) in the allele-specific blocker probe is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In some embodiments, the non-extendable blocker moiety comprises a modification to the 3'-end of the allele-specific blocker probe which prevents the addition of further bases to the 3'-end by a polymerase. In particular embodiments, the non-extendable blocker moiety is selected from the group consisting of an optionally substituted $C_1$-$C_{24}$ alkyl diol, an optionally substituted $C_2$-$C_{24}$ alkenyl diol, an optionally substituted $C_2$-$C_{24}$ alkynyl diol, and combinations thereof. In a preferred embodiment, the non-extendable blocker moiety comprises a 3'-hexanediol modification to the allele-specific blocker probe.

In certain embodiments, the non-extendable blocker moiety does not comprise or include a minor groove binder (MGB). In certain other embodiments, the non-extendable blocker moiety does not comprise or include a $PO_4$ group. In further embodiments, the non-extendable blocker moiety consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In some embodiments, the detector probe comprises a TaqMan® probe. In certain embodiments, the nucleic acid sample is selected from the group consisting of blood, serum, plasma, fine needle aspirate, tumor tissue, and combinations thereof. In other embodiments, the first allelic variant is a mutant allele and the second allelic variant is the wild-type allele. In particular embodiments, the method reduces the background signal of the second allelic variant during the amplification reaction.

In certain embodiments, the first allelic variant of the target gene can be quantitated by determining the threshold cycle or Ct value in which a change in the detectable property of the detector probe first becomes detectable above a background level. In some embodiments, a standard curve for the first allelic variant can be generated by performing the method of the invention on a serial dilution of nucleic acid sample from a cell line positive for the allelic variant. In some instances, the first allelic variant is quantitated by comparing the Ct value obtained for the sample with Ct values from the standard curve. In particular embodiments, the standard curve is used to determine one or more Ct values (e.g., relative to the starting amount of nucleic acid in the positive control sample), line slope values, and/or line intercept values obtained by performing the method of the invention on a serial dilution of nucleic acid sample from a cell line positive for the allelic variant. In other embodiments, the amount and/or percent (e.g., percent mutation) of the first allelic variant present in the sample is calculated based upon at least one, two, three, or four of the following: starting amount of nucleic acid in the sample (e.g., DNA per reaction, which can be expressed as a $\log_{10}$ value in ng or any other unit of weight); Ct value; line slope value (e.g., from the standard curve); line intercept value (e.g., from the standard curve); and combinations thereof.

In another aspect, the present invention provides a reaction mixture comprising:
(a) a nucleic acid molecule;
(b) an allele-specific primer, wherein an allele-specific nucleotide portion of the allele-specific primer is complementary to a first allelic variant of a target sequence, and wherein the allele-specific primer comprises at least one nucleic acid modification (e.g., one or a plurality of nucleic acid modifications);
(c) an allele-specific blocker probe that is complementary to a region of the target sequence comprising a second allelic variant, wherein the allele-specific blocker probe comprises a non-extendable blocker moiety and at least one nucleic acid modification (e.g., one or a plurality of nucleic acid modifications);
(d) a detector probe; and
(e) a locus-specific primer that is complementary to a region of the target sequence that is 3' from the first allelic variant and on the opposite strand.

In some embodiments, the nucleic acid modification(s) in the allele-specific primer is/are located at the allele-specific nucleotide portion, at the 5'-end of the allele-specific primer, and/or at the 3'-end of the allele-specific primer. In certain embodiments, the allele-specific primer comprises two or more non-consecutive nucleic acid modifications. In some embodiments, the nucleic acid modification(s) in the allele-specific primer is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In other embodiments, the nucleic acid modification(s) in the allele-specific blocker probe is/are located at the allele-specific nucleotide portion and/or at an internal position in the allele-specific blocker probe. In certain embodiments, the allele-specific blocker probe comprises two or more non-consecutive nucleic acid modifications. In some instances, the nucleic acid modification(s) in the allele-specific blocker probe is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In some embodiments, the non-extendable blocker moiety comprises a modification to the 3'-end of the allele-specific blocker probe which prevents the addition of further bases to the 3'-end by a polymerase. In particular embodiments, the non-extendable blacker moiety is selected from the group consisting of an optionally substituted $C_1$-$C_{24}$ alkyl diol, an optionally substituted $C_2$-$C_{24}$ alkenyl diol, an optionally substituted $C_2$-$C_{24}$ alkynyl diol, and combinations thereof. In a preferred embodiment, the non-extendable blocker moiety comprises a 3'-hexanediol modification to the allele-specific blocker probe.

In certain embodiments, the non-extendable blocker moiety does not comprise or include a minor groove binder (MGB). In certain other embodiments, the non-extendable blocker moiety does not comprise or include a $PO_4$ group. In further embodiments, the non-extendable blocker moiety consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In some embodiments, the detector probe comprises a TaqMan® probe. In certain embodiments, the nucleic acid molecule is obtained from a sample selected from the group consisting of blood, serum, plasma, fine needle aspirate, tumor tissue, and combinations thereof. In other embodiments, the first allelic variant is a mutant allele and the second allelic variant is the wild-type allele.

In yet another aspect, the present invention provides a composition comprising:
  (a) an allele-specific primer, wherein an allele-specific nucleotide portion of the allele-specific primer is complementary to a first allelic variant of a target sequence, and wherein the allele-specific primer comprises at least one nucleic acid modification (e.g., one or a plurality of nucleic acid modifications); and
  (b) an allele-specific blocker probe that is complementary to a region of the target sequence comprising a second allelic variant, wherein the allele-specific blocker probe comprises a non-extendable blocker moiety and at least one nucleic acid modification (e.g., one or a plurality of nucleic acid modifications).

In some embodiments, the composition further comprises: (c) a detector probe; and/or (d) a locus-specific primer that is complementary to a region of the target sequence that is 3' from the first allelic variant and on the opposite strand.

In some embodiments, the nucleic acid modification(s) in the allele-specific primer is/are located at the allele-specific nucleotide portion, at the 5'-end of the allele-specific primer, and/or at the 3'-end of the allele-specific primer. In certain embodiments, the allele-specific primer comprises two or more non-consecutive nucleic acid modifications. In some embodiments, the nucleic acid modification(s) in the allele-specific primer is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In other embodiments, the nucleic acid modification(s) in the allele-specific blocker probe is/are located at the allele-specific nucleotide portion and/or at an internal position in the allele-specific blocker probe. In certain embodiments, the allele-specific blocker probe comprises two or more non-consecutive nucleic acid modifications. In some instances, the nucleic acid modification(s) in the allele-specific blocker probe is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In some embodiments, the non-extendable blocker moiety comprises a modification to the 3'-end of the allele-specific blocker probe which prevents the addition of further bases to the 3'-end by a polymerase. In particular embodiments, the non-extendable blocker moiety is selected from the group consisting of an optionally substituted $C_1$-$C_{24}$ alkyl diol, an optionally substituted $C_2$-$C_{24}$ alkenyl diol, an optionally substituted $C_2$-$C_{24}$ alkynyl diol, and combinations thereof. In a preferred embodiment, the non-extendable blocker moiety comprises a 3'-hexanediol modification to the allele-specific blocker probe.

In certain embodiments, the non-extendable blocker moiety does not comprise or include a minor groove binder (MGB). In certain other embodiments, the non-extendable blocker moiety does not comprise or include a $PO_4$ group. In further embodiments, the non-extendable blocker moiety consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In further embodiments, the first allelic variant is a mutant allele and the second allelic variant is the wild-type allele.

In another aspect, the present invention provides a kit comprising two or more containers comprising the following components independently distributed in one of the two or more containers:
  (a) an allele-specific primer, wherein an allele-specific nucleotide portion of the allele-specific primer is complementary to a first allelic variant of a target sequence, and wherein the allele-specific primer comprises at least one nucleic acid modification (e.g., one or a plurality of nucleic acid modifications); and
  (b) an allele-specific blocker probe that is complementary to a region of the target sequence comprising a second allelic variant, wherein the allele-specific blocker probe comprises a non-extendable blocker moiety and at least one nucleic acid modification (e.g., one or a plurality of nucleic acid modifications).

In some embodiments, the kit further comprises: (c) a detector probe; and/or (d) a locus-specific primer that is complementary to a region of the target sequence that is 3' from the first allelic variant and on the opposite strand.

In some embodiments, the nucleic acid modification(s) in the allele-specific primer is/are located at the allele-specific nucleotide portion, at the 5'-end of the allele-specific primer, and/or at the 3'-end of the allele-specific primer. In certain embodiments, the allele-specific primer comprises two or more non-consecutive nucleic acid modifications. In some embodiments, the nucleic acid modification(s) in the allele-specific primer is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In other embodiments, the nucleic acid modification(s) in the allele-specific blocker probe is/are located at the allele-specific nucleotide portion and/or at an internal position in the allele-specific blocker probe. In certain embodiments, the allele-specific blocker probe comprises two or more non-consecutive nucleic acid modifications. In some instances, the nucleic acid modification(s) in the allele-specific blocker probe is/are selected from the group consisting of locked nucleic acids (LNA), peptide nucleic acids (PNA), threose nucleic acids (TNA), zip nucleic acids (ZNA), triazole nucleic acids (TzNA), and combinations thereof.

In some embodiments, the non-extendable blocker moiety comprises a modification to the 3'-end of the allele-specific blocker probe which prevents the addition of further bases to the 3'-end by a polymerase. In particular embodiments, the non-extendable blocker moiety is selected from the group consisting of an optionally substituted $C_1$-$C_{24}$ alkyl diol, an optionally substituted $C_2$-$C_{24}$ alkenyl diol, an optionally substituted $C_2$-$C_{24}$ alkynyl diol, and combinations thereof in a preferred embodiment, the non-extendable blocker moiety comprises a 3'-hexanediol modification to the allele-specific blocker probe.

In certain embodiments, the non-extendable blocker moiety does not comprise or include a minor groove binder (MOB). In certain other embodiments, the non-extendable blocker moiety does not comprise or include a $PO_4$ group. In further embodiments, the non-extendable blocker moiety consists essentially of or consists of an optionally substituted $C_1$-$C_{24}$ alkyl diol (e.g., a 3'-hexanediol modification), an optionally substituted $C_2$-$C_{24}$ alkenyl diol, or an optionally substituted $C_2$-$C_{24}$ alkynyl diol.

In some embodiments, the first allelic variant is a mutant allele and the second allelic variant is the wild-type allele. In other embodiments, the kit further comprises instructions for use of the allele-specific primer and the allele-specific blocker probe for detecting or quantitating the first allelic variant of the target sequence in a nucleic acid sample suspected of having the second allelic variant of the target sequence.

V. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Somatic Mutation Genotyping Assay Methodology

FIG. 1 depicts one embodiment of the somatic mutation detection assays of the present invention. An allele-specific primer and an allele-specific blocker probe are used for each single nucleotide polymorphism (SNP) to be analyzed in a sample such as a blood or fine needle aspirate (FNA) sample. The allele-specific primer can comprise a locked nucleic acid (LNA) at the 3'-end that is specific for a variant (e.g., mutant) allele, whereas the allele-specific blocker probe can comprise a hexanediol blocker moiety at the 3'-end and a LNA at a position between about 5-15 nucleotides 5' of the blocker moiety (e.g., in the middle of the oligonucleotide sequence) that is specific for the wild-type allele.

The assay methods of the present invention can be performed on an ABI 7900HT Real Time PCR Instrument, although any type of real time PCR instrument known to one of skill in the art can be used. Exemplary reaction conditions include the following: Stage 1: 95.0° C. for 10:00 min; Stage 2: Repeats: 40, 95.0° C. for 0:20 min and 60.0° C. for 0:45 min.

As depicted in FIG. 1, hybridization of the allele-specific blocker probe (e.g., "Blocker LNA Hexanediol Oligonucleotide") to the wild-type allele prevents amplification of the wild-type allele, whereas hybridization of the allele-specific primer (e.g., "Allele specific LNA primer") to the mutant allele enables the mutant allele to be selectively amplified with high sensitivity and low background. In particular embodiments, the use of LNA nucleosides improves the signal to noise ratio and substantially reduces the wild-type background signal.

Example 2

Exemplary Somatic Mutation Genotyping Assays for Detection of SNPs

This examples illustrates that the use of allele-specific primers and allele-specific blocker probes containing modified bases improves the discrimination of allelic variants.

Figure 2:
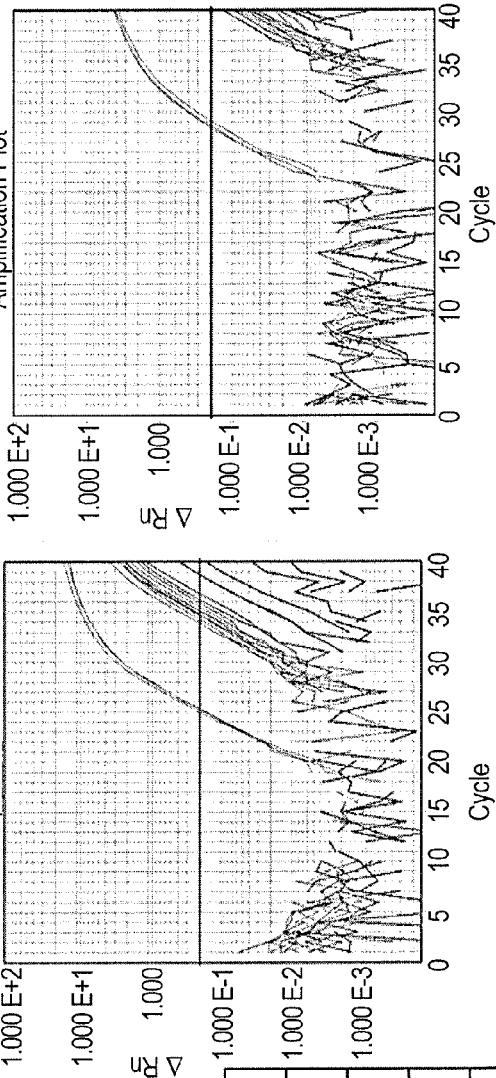
FIG. 2 illustrates that the use of an allele-specific primer comprising a locked nucleic acid (LNA) modification at the 3'-end ("+A" in "G12S ASP-LNA"; SEQ ID NO:1) and an allele-specific blocker probe comprising a LNA modification in the middle of the oligonucleotide sequence ("+G" in "G12S blocker-LNA"; SEQ ID NO:2) and a 3'-hexanediol modification ("C6" in "G12S blocker-LNA") improves the discrimination of allelic variants at the KRAS G12S SNP. G12S TaqMan probe=SEQ ID NO:3; G12S reverse=SEQ ID NO:4.

In particular, FIG. 2 shows that the use of an allele-specific primer comprising a LNA modification at the 3'-end ("+A" in "G12S ASP-LNA") and an allele-specific blocker probe comprising a LNA modification in the middle of the oligonucleotide sequence ("+G" in "G12S blocker-LNA") and a 3'-hexanediol modification ("C6" in "G12S blocker-LNA") improves the discrimination of allelic variants at the KRAS G12S polymorphic site. Allele-specific real time PCR performed using allele-specific primers and blocker probes without LNA modifications incorrectly detected the presence of the KRAS G12S mutant allele in all 8 of the cell lines negative for the mutant allele (i.e., H1975, H1993, U87MG, A375, PC3, A431NS, #28, and #29 cell lines). In contrast, allele-specific real time PCR performed using allele-specific primers and blocker probes of the invention comprising LNA and hexanediol modifications correctly identified these cell lines as negative for the KRAS G12S mutation. Although the allele-specific primer and blocker probe without LNA modifications identified the KRAS G12S mutation in the KRAS G12S positive A549 cell line, the ΔCt value was 9 (compare the "Ct" values for #29 versus A549), which was significantly lower than the ΔCt value of 12 observed with the LNA and hexanediol-modified primers and probes described herein. Without being bound to any particular theory, an increase in ΔCt values indicates an improvement in the discrimination of allelic variants during PCR. In addition, the use of the modified primers and probes of the invention substantially reduces the wild-type background signal, even in samples containing an abundance of the wild-type allele.

Figure 3:
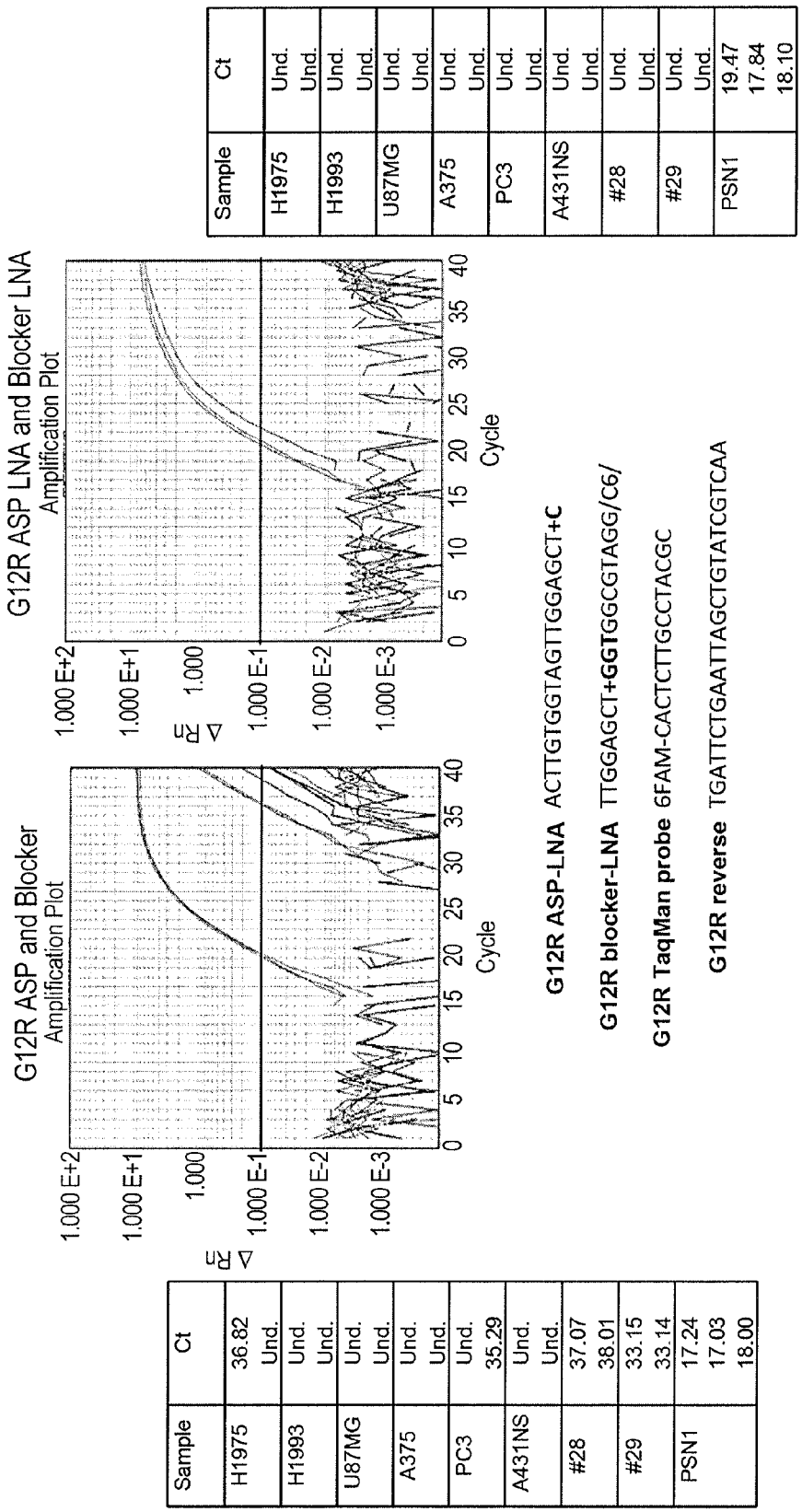
FIG. 3 illustrates that the use of an allele-specific primer comprising a LNA modification at the 3'-end ("+C" in "G12R ASP-LNA"; SEQ ID NO:5) and an allele-specific blocker probe comprising a LNA modification in the middle of the oligonucleotide sequence ("+G" in "G12R blocker-LNA"; SEQ ID NO:2) and a 3'-hexanediol modification ("C6" in "G12R blocker-LNA") improves the discrimination of allelic variants at the KRAS G12R SNP. G12R TaqMan probe=SEQ ID NO:3; G12R reverse=SEQ ID NO:4.

Similarly, FIG. 3 shows that the use of an allele-specific primer comprising a LNA modification at the 3'-end ("+C" in "G12R ASP-LNA") and an allele-specific blocker probe comprising a LNA modification in the middle of the oligonucleotide sequence ("+G" in "G12R blocker-LNA") and a 3'-hexanediol modification ("C6" in "G12R blocker-LNA") improves the discrimination of allelic variants at the KRAS G12R polymorphic site. Allele-specific real time PCT performed using allele-specific primers and blocker probes without LNA modifications incorrectly detected the presence of the KRAS G12R mutant allele in several of the cell lines negative for the mutant allele. In contrast, allele-specific real time PCT performed using allele-specific primers and blocker probes of the invention comprising LNA and hexanediol modifications correctly identified all of these cell lines as negative for the KRAS G12R mutation.

Figure 4:
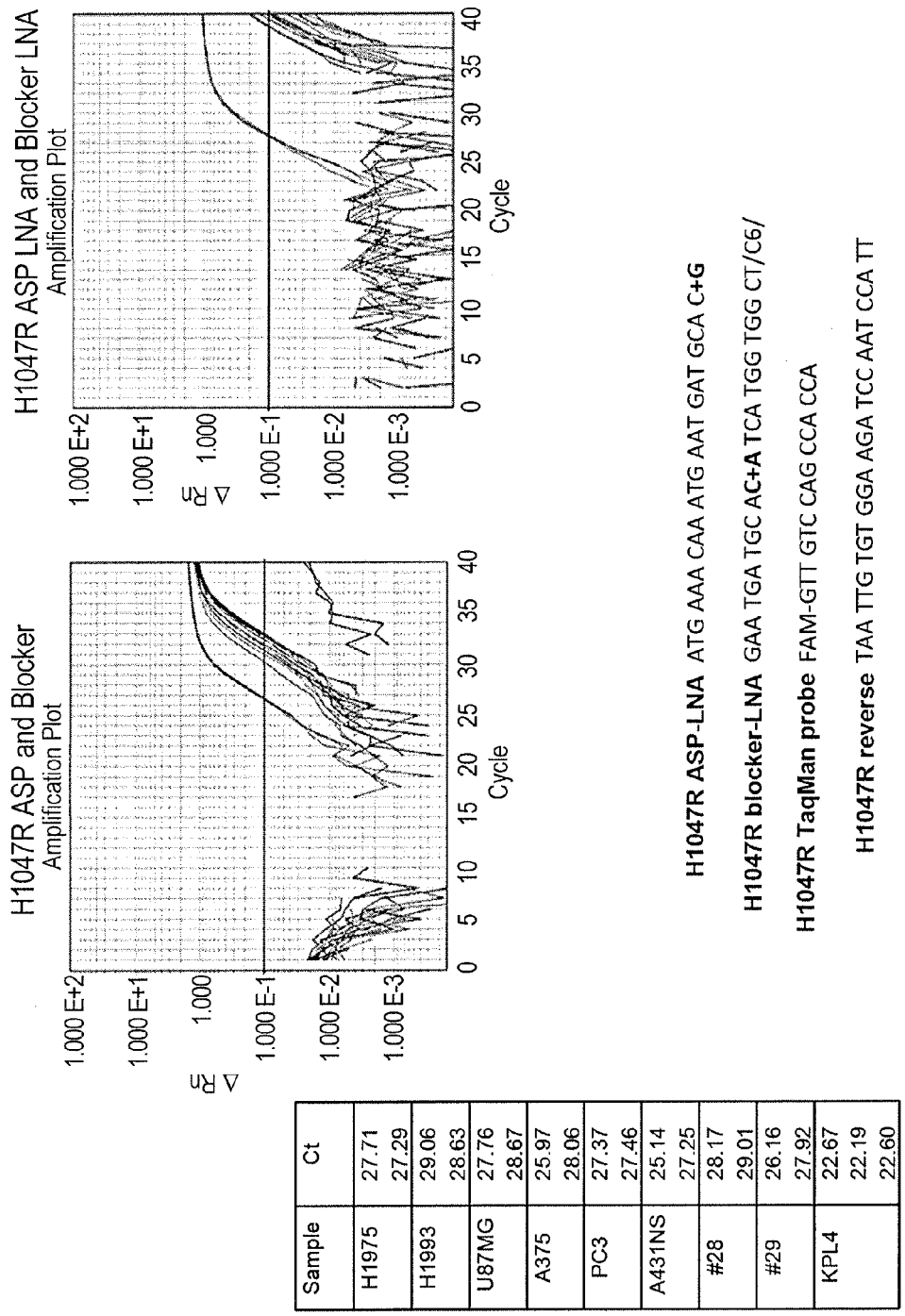
FIG. 4 illustrates that the use of an allele-specific primer comprising a LNA modification at the 3'-end ("+G" in "H1047R ASP-LNA"; SEQ ID NO:6) and an allele-specific blocker probe comprising a LNA modification in the middle of the oligonucleotide sequence ("+A" in "H1047R blocker-LNA"; SEQ ID NO:7) and a 3'-hexanediol modification ("C6" in "H1047R blocker-LNA") improves the discrimination of allelic variants at the PIK3CA H1047R SNP. H1047R TaqMan probe=SEQ ID NO:8; H1047R reverse=SEQ ID NO:9.

Likewise, FIG. 4 shows that the use of an allele-specific primer comprising a LNA modification at the 3'-end ("+G" in "H1047R ASP-LNA") and an allele-specific blocker probe comprising a LNA modification in the middle of the oligonucleotide sequence ("+A" in "H1047R blocker-LNA") and a 3'-hexanediol modification ("C6" in "H1047R blocker-LNA") improves the discrimination of allelic variants at the PIK3CA H1047R polymorphic site. The allele-specific primer and blocker probe without LNA modifications identified the PIK3CA H1047R mutation in the PIK3CA H1047R positive KPL4 cell line. However, the use of the LNA and hexanediol-modified primers and probes of the present invention substantially increased ΔCt values based upon a comparison of ΔCt values of about 4-6 for PCR without LNA modifications to ΔCt values of greater than 10 for PCR with LNA modifications, wherein ΔCt values were calculated by subtracting the Ct values of the KPL4 cell line from the Ct values of any of the H1975, H1993, U87MG, A375, PC3, A431NS, #28, or #29 cell lines. As discussed herein, an increase in ΔCt values indicates an improvement in the discrimination of allelic variants during PCR. In addition, the use of the modified primers and probes of the invention substantially reduces the wild-type background signal, even in samples containing an abundance of the wild-type allele.

Figure 5:
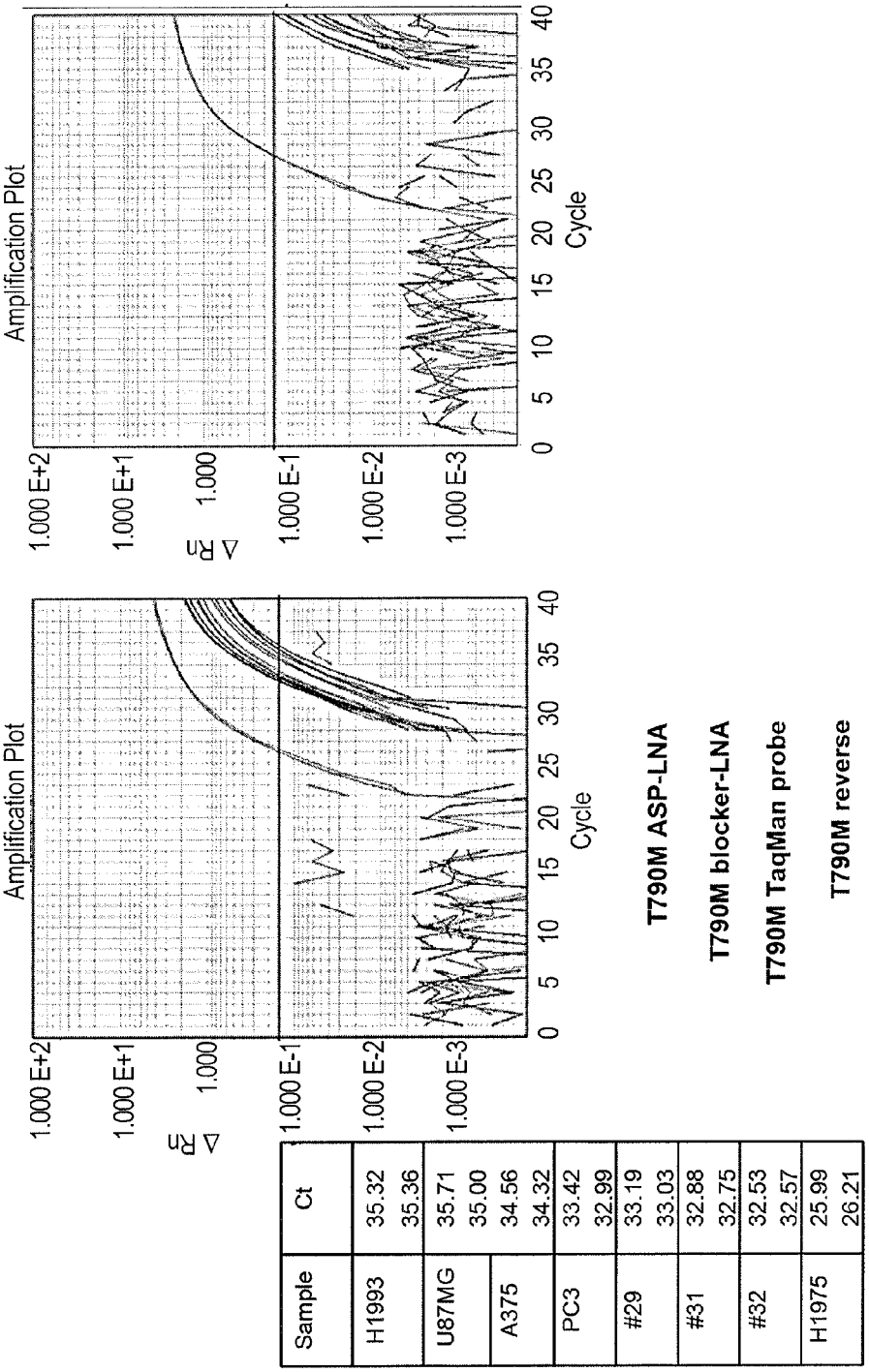
FIG. 5 illustrates improved allelic variant discrimination at the EGFR T790M polymorphic site using the LNA-modified allele-specific primers and probes of the present invention.
Figure 6:
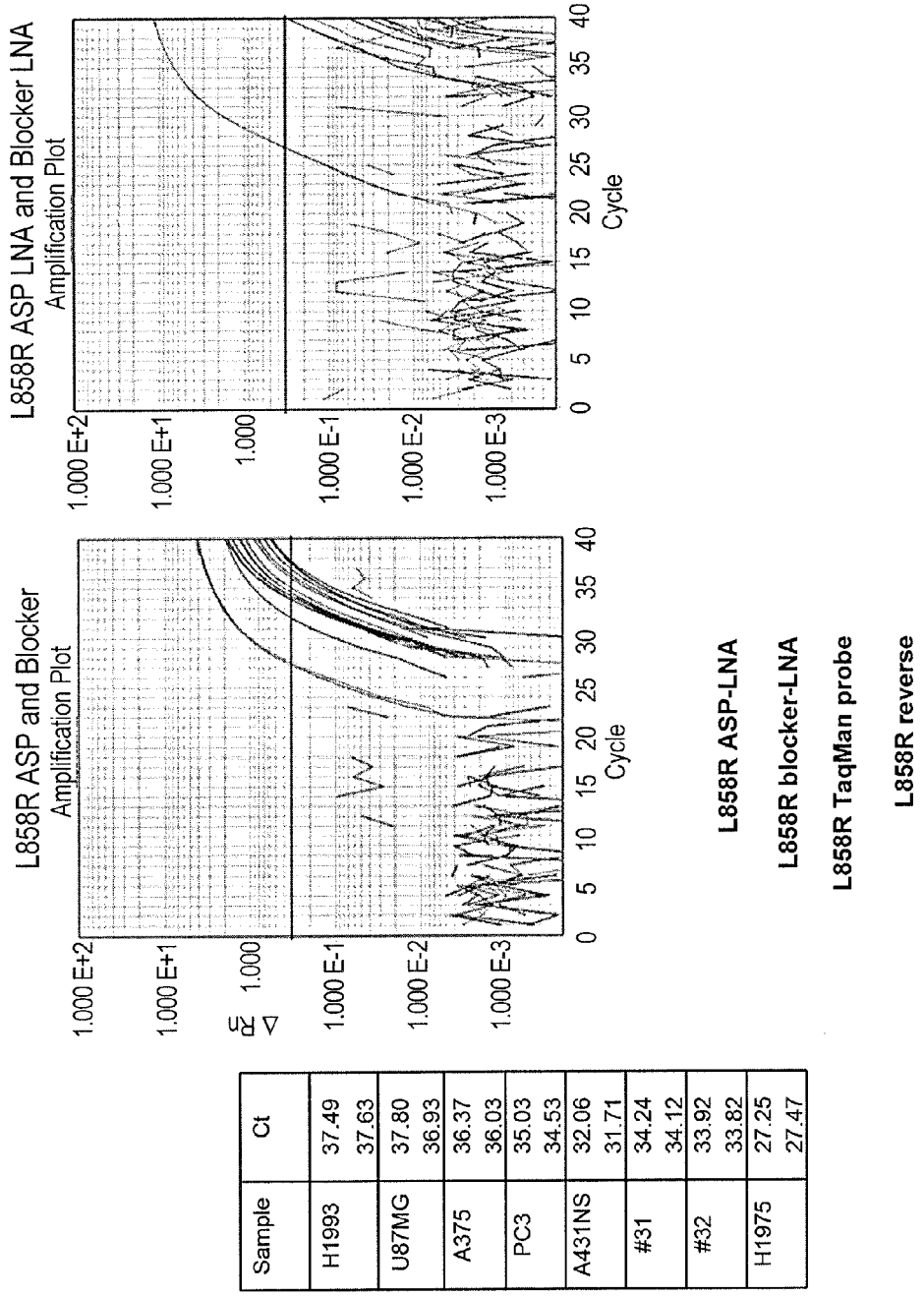
FIG. 6 illustrates improved allelic variant discrimination at the EGFR L858R polymorphic site using the LNA-modified allele-specific primers and probes of the present invention.

FIGS. 5 and 6 illustrate examples of improved allelic variant discrimination at the EGFR T790M and EGFR L858R polymorphic sites, respectively, using the LNA-modified allele-specific primers and probes of the present invention. Allele-specific real time PCR performed using allele-specific primers and blocker probes without LNA modifications incorrectly detected the presence of both EGFR mutations in all 7 of the cell lines negative for the mutant allele (i.e., H1993, U87MG, A375, PC3, #29, #31, and #32 cell lines). In contrast, allele-specific real time PCR performed using allele-specific primers and blocker probes of the invention comprising LNA and hexanediol modifications correctly identified all 7 of these cell lines as negative for both EGFR mutations, and correctly identified the EGFR T790M and EGFR L858R positive H1975 cell line as containing both mutant alleles.

Figure 7:
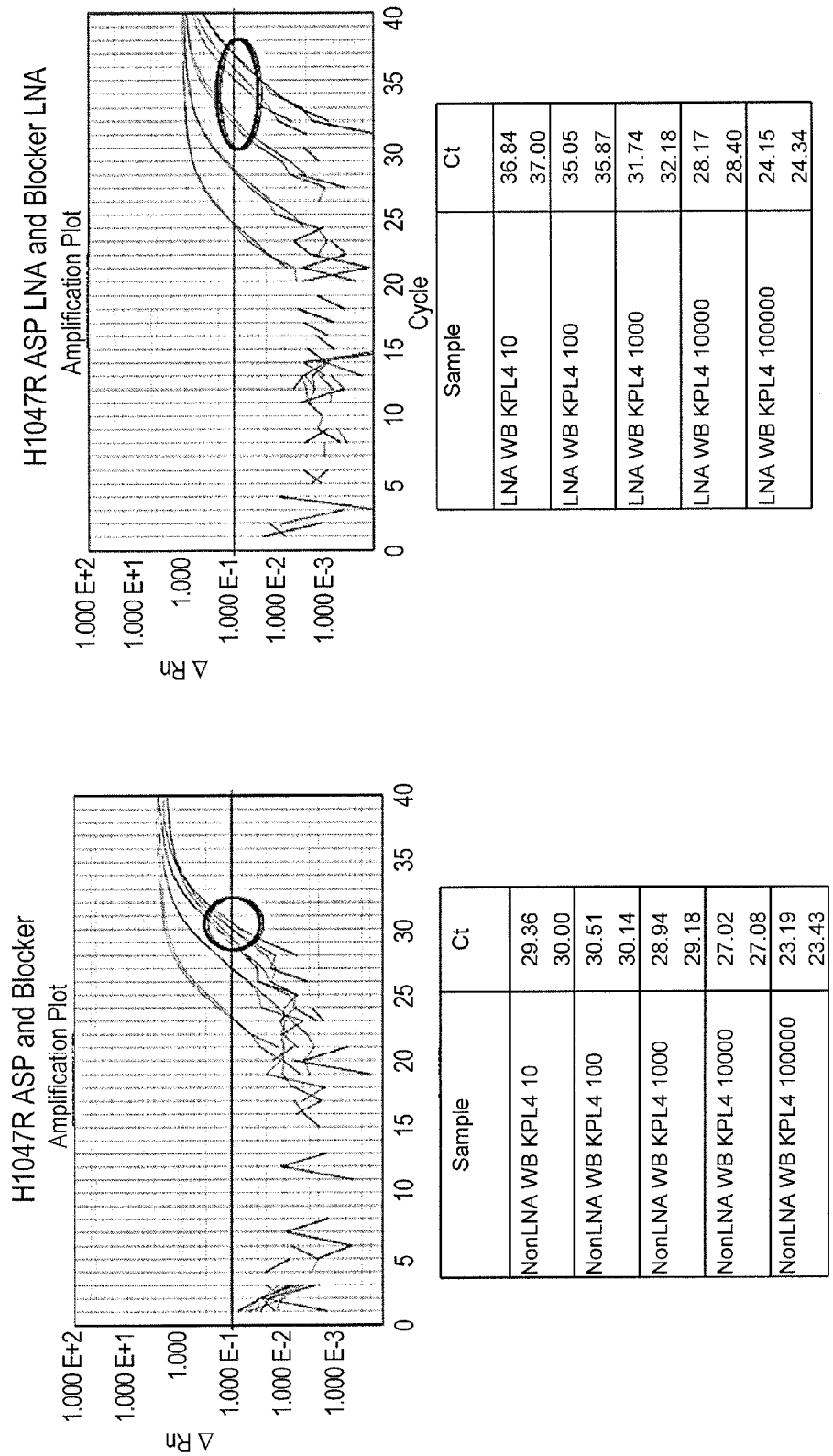
FIG. 7 illustrates the effect of an abundant amount of wild-type DNA from whole blood on the interference of detecting the PIK3CA H1047R variant allele in H1047R-positive KPL4 cells.
Figure 8:
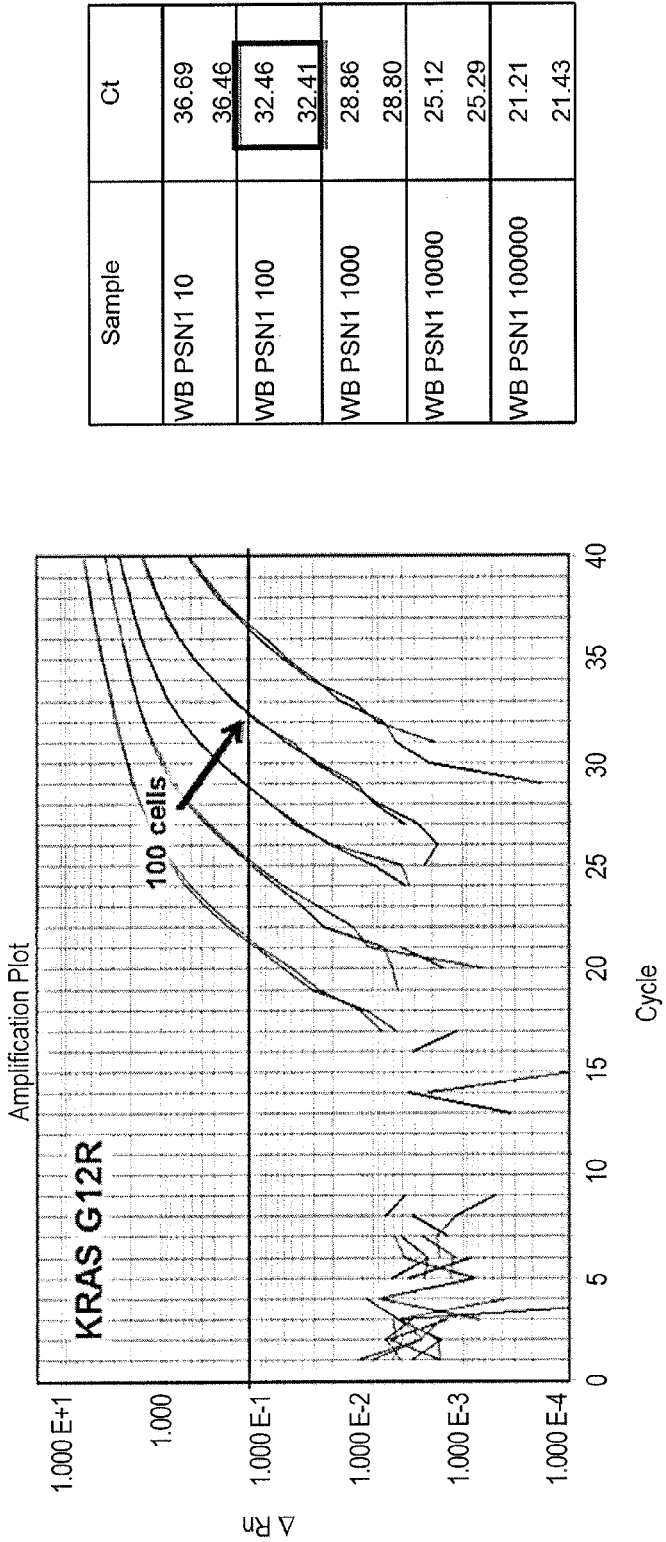
FIG. 8 illustrates the effect of an abundant amount of wild-type DNA from whole blood on the interference of detecting the KRAS G12R variant allele in G12R-positive PSN1 cells.

FIG. 7 illustrates the effect of an abundant amount of wild-type DNA from whole blood on the interference of detecting a mutant allele of interest such as the PIK3CA H1047R variant allele in H1047R-positive KPL4 cells. FIG. 8 illustrates the effect of an abundant amount of wild-type DNA from whole blood on the interference of detecting a mutant allele of interest such as the KRAS G12R variant allele in G12R-positive PSN1 cells. As shown in FIG. 8, the G12R signal is still detectable with as low as 100 G12R-positive PSN1 cells in the spiked whole blood sample, which represents 0.01% of the whole blood count.

Example 3

Screening Colorectal Cancer Samples with Somatic Mutation Genotyping Assay Methodology This examples illustrates the screening of colorectal cancer (CRC) tissue samples for the presence of the PIK3CA H1047R variant allele using the allele-specific primers and allele-specific blocker probes of the present invention containing modified bases including LNA modifications.

Figure 9:
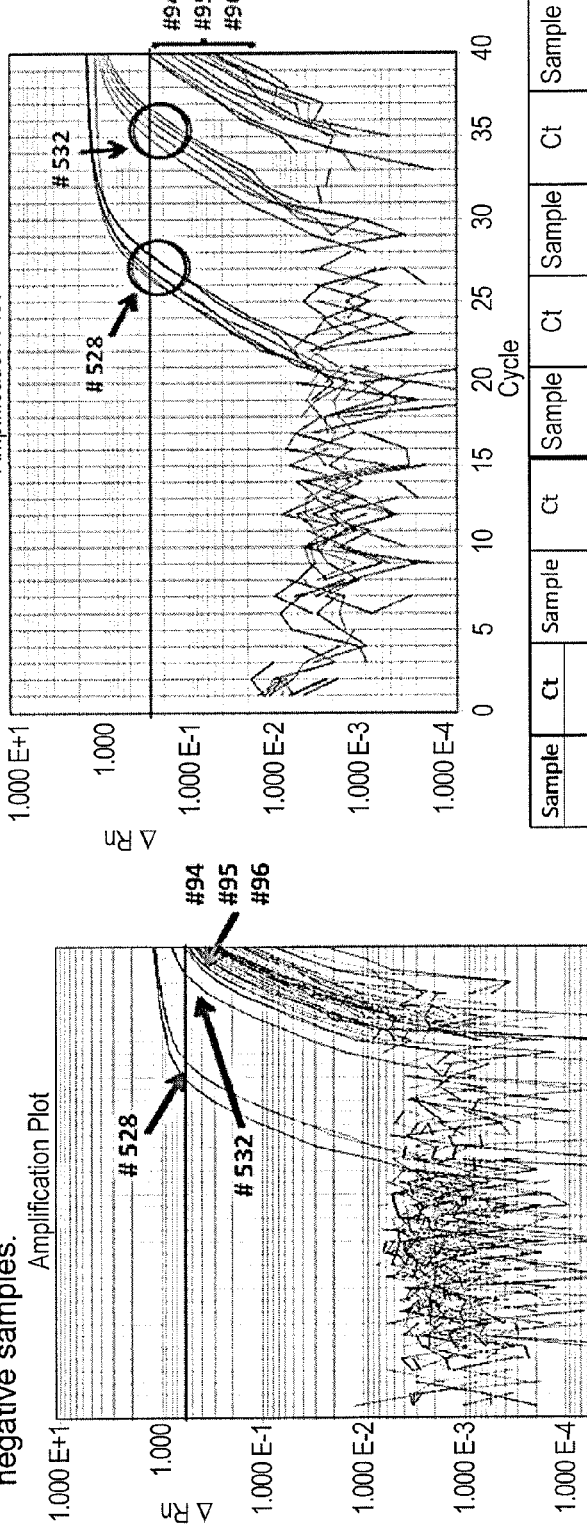
FIG. 9 shows that screening of 150 CRC tissue samples indicated that there was no interference observed from the negative samples and that detection of a weak signal can be validated by titration.

FIG. 9 shows that screening of 150 CRC tissue samples indicated that there was no interference observed from the negative samples and that detection of a weak signal can be validated by titration. The H1047R-positive samples #532 and #528 were validated by titration, while the H1047R-negative samples #94, #95, and #96 had undetectable levels of the H1047R variant allele at all concentrations tested.

In sum, this example demonstrates that the somatic mutation genotyping assays of the present invention are highly sensitive, very specific, highly selective, and robust and can be used to test clinical samples to detect and/or quantitate allelic variants in genes such as KRAS, PIK3CA, and EGFR.

Example 4

Comparison of Somatic Mutation Genotyping Assay Methodology with Scorpion and BEAMing Assays This examples illustrates a comparison between the somatic mutation genotyping assay of the present invention and the Scorpion assay from Qiagen or the BEAMing assay from Inostics on KRAS G12A detection in whole blood spiked with varying amounts of SW1116 (G12A-positive) cells.

Figure 10:
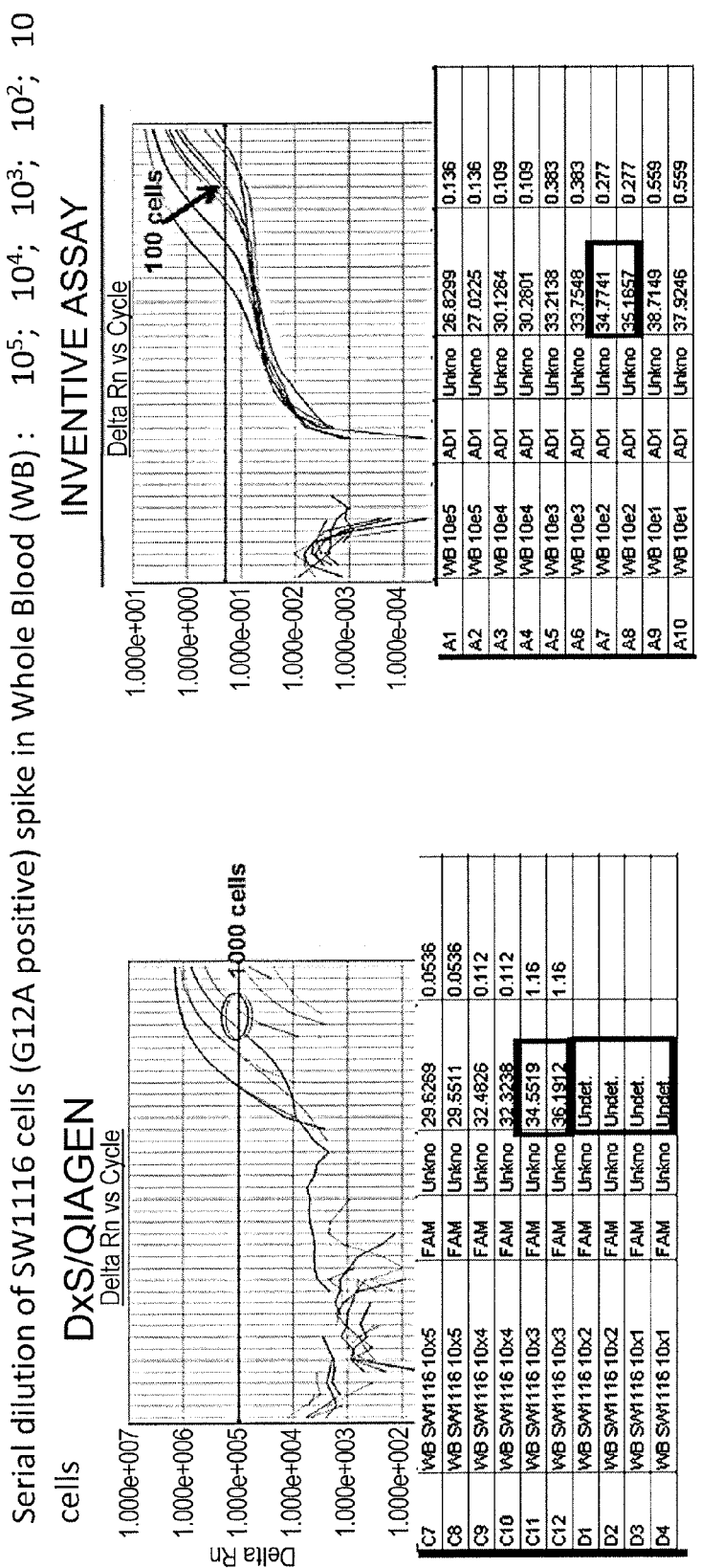
FIG. 10 shows that the DxS/Qiagen Scorpion assay can only detect 1000 cells in the mixture of whole blood spiked with a serial dilution of SW1116 (G12A-positive) cells.

FIG. 10 shows that the DxS/Qiagen Scorpion assay can only detect 1000 cells in the mixture of whole blood spiked with a serial dilution of SW1116 (G12A-positive) cells. The sensitivity is lost by 100 cells. In contrast, with the use of the genotyping assay of the present invention ("Inventive Assay"), the G12A signal is still detectable with as low as 10 to 100 of the SW1116-positive cells in the whole blood mixture. 100 cells represent 0.01% of the whole blood count. Even at 1000 cells, the Ct curve was not tight for the DxS/Qiagen Scorpion assay.

FIG. 11 shows a serial dilution of KPL4 (H1047R), A549 (G12S), and PSN1 (G12R) cells spiked in whole blood (WB) at 10, 50, 100, 250 and 500 cells. Notably, the Inostics BEAMing assay made the incorrect call and identified 14 out of 15 mutant samples as wild-type samples. In fact, the Inostics assay only detected the mutation when 1000 cells were present in whole blood, and displayed no sensitivity at 500 cells or less. In contrast, FIG. 12 shows that the somatic mutation genotyping assay of the present invention ("Inventive Assay") had a detectable signal as low as 50 to 100 positive cells in the WB mixture. 100 cells represent 0.01% of the whole blood count.

In sum, this example demonstrates that the somatic mutation genotyping assay of the present invention dramatically improves the allelic PCR assay compared to the Scorpion assay from Qiagen and the BEAMing assay from Inostics. In particular, a weak signal can be validated by titration and the assays of the invention can detect as low as 0.01% of cells with a mutant allele in a background of whole blood with abundant levels of the wild-type allele. As such, the methodology described herein is superior to the Scorpion and BEAMing assays in samples such as whole blood.

Example 5

Somatic Mutation Genotyping Assay Methodology Using Nucleic Acid Modifications

This example illustrates multiple embodiments of the somatic mutation detection assays of the present invention. For this example, the KRAS G12A assay was chosen as an exemplary assay for illustrating the methods of the invention. In particular, the experiments described herein address the following components of the assay: (1) allele-specific primers with and without LNA; (2) 3' end modification on blocker probes; (3) blocker probes with different Tm; (4) blocker probes with and without LNA; and (5) the combination of allele-specific primers and blocker probes with LNA and without LNA.

The methods described in this example are based on real time allele-specific PCR in combination with a locus-specific primer, an allele-specific primer, a blocker probe, and a detector probe. The methods were designed to be highly selective and sensitive in differentiating and quantitating the presence of a mutant allele from a wild type allele. In particular, the exemplary assay was performed using GTXpress™ Master Mix from Applied Biosystems (Foster City, Calif.). For the real-time PCR reaction, the following cycling condition was used: Stage 1: 95.0° C. for 10:00 min, and Stage 2: Repeats: 40 times, 95.0° C. for 0:20 min and 60.0° C. for 0:45 min.

Figure 13:
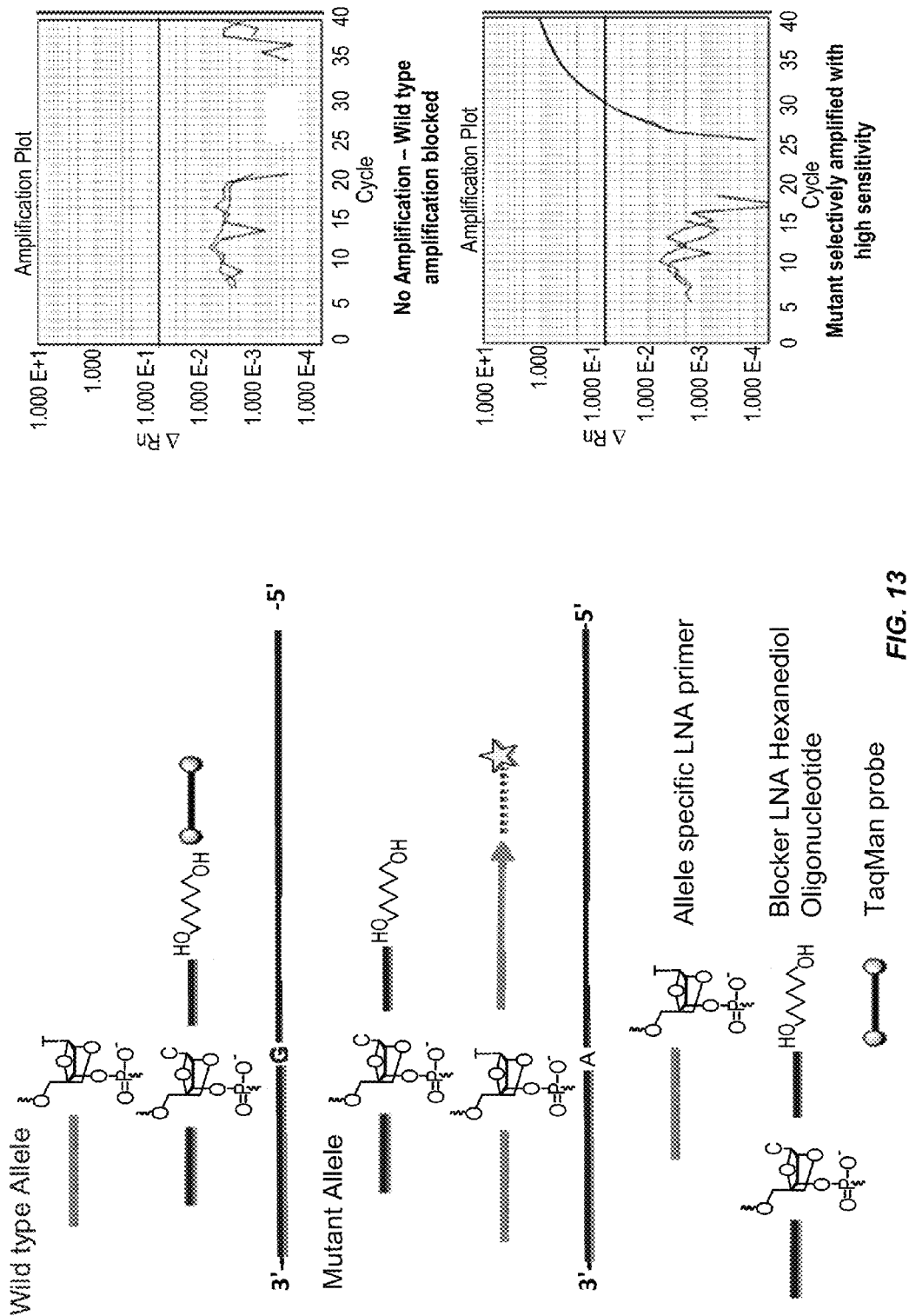
FIG. 13 illustrates an exemplary embodiment of the invention in which the rare allele, and not the wild-type allele is selectively amplified using the methods described herein. The wild-type allele does not produce an amplification product because the blocker probe with LNA (C in FIG. 13) and hexanediol modifications hybridizes to the wild-type allele, thus impeding real-time PCR amplification. The allele-specific primer with a LNA modification (T in FIG. 13) preferably hybridizes to the mutant allele rather than the blocker probe, and thus facilitates the generation of a real-time PCR amplification product.

Experiment #1 shows that the KRAS G12A assay of the present invention comprising an allele-specific primer with LNA successfully amplified the mutant allele with high selectivity and sensitivity. In this embodiment of the present invention, the variant nucleotide (T) of the allele-specific primer was a locked nucleic acid (LNA) and was located at the 3'-end of the primer. The blocker probe had a LNA and a hexanediol modification at the 3' end. The detector probe was a Taqman probe (Life Technologies). The results of the real-time PCR assay show that the blocker probe hybridized to the wild-type allele and blocked its amplification (FIG. 13). In addition, the mutant allele was selectively amplified with high sensitivity by the assay (FIG. 13).

Figure 14:
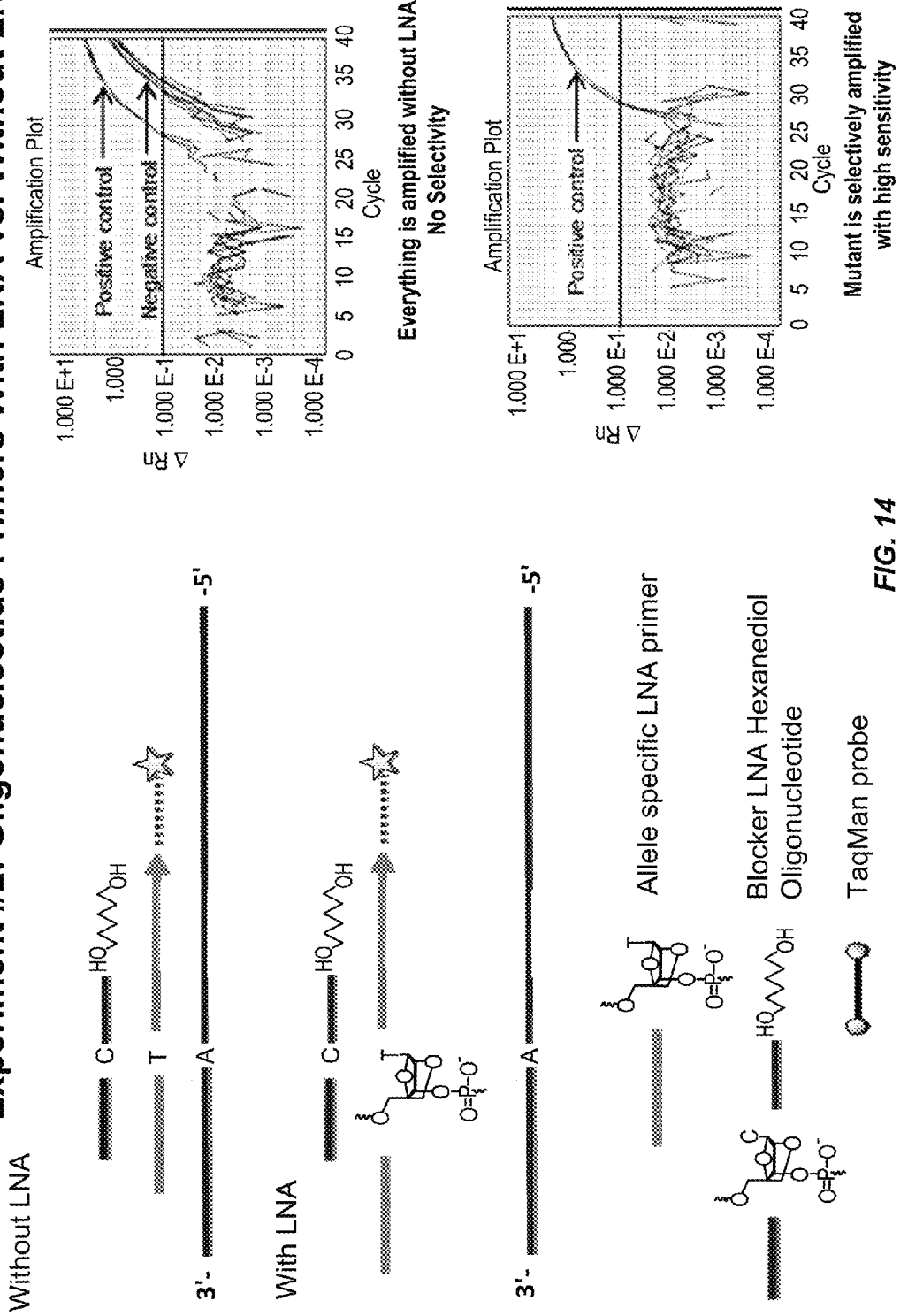
FIG. 14 also shows that an allele-specific primer can amplify both the wild-type (negative control) and mutant (positive control) alleles. The amplification plots illustrate that the assay with the allele-specific LNA primer has high sensitivity. The primer with LNA selective amplifies the mutant allelic variant.

Experiment #2 shows that the SNP genotyping assay of the present invention has improved selectivity and sensitivity for allelic discrimination when the allele-specific primer comprises a locked nucleic acid (LNA). FIG. 14 shows that a KRAS G12A assay without LNA on the allele-specific primer and blocker probe generated amplification products from the positive control (mutant allele) and negative control (wild-type allele) samples. This embodiment of the present invention did not show sufficient selectivity for the allelic variants. Yet, a KRAS G12A assay LNA modifications on the allele-specific primer and blocker probe was able to selectively amplify the positive control sample and not the negative control. FIG. 14 shows that the assay with the LNA at the variant nucleotide (T) amplified the mutant allele with high sensitivity.

Experiment #3 shows that the presence of two LNAs on a allele-specific primer in the SNP genotyping assay improved the performance of the assay. In this embodiment of the present invention, the design of two allele-specific primers were compared. One primer had a LNA at the variant nucleotide (T). The other primer had a second LNA (A) located 5' of the variant nucleotide. The assay comprising the allele-specific primer with 2 strategically placed LNAs showed better amplification and a lower Ct value (FIG. 15). LNA can be placed at the 3' end of the allele-specific primer and at 2, 3, 4, 5 or 6 bases from the 3' end. LNA can be placed at the 5' end and the 3' end of the allele-specific primer.

Figure 16:
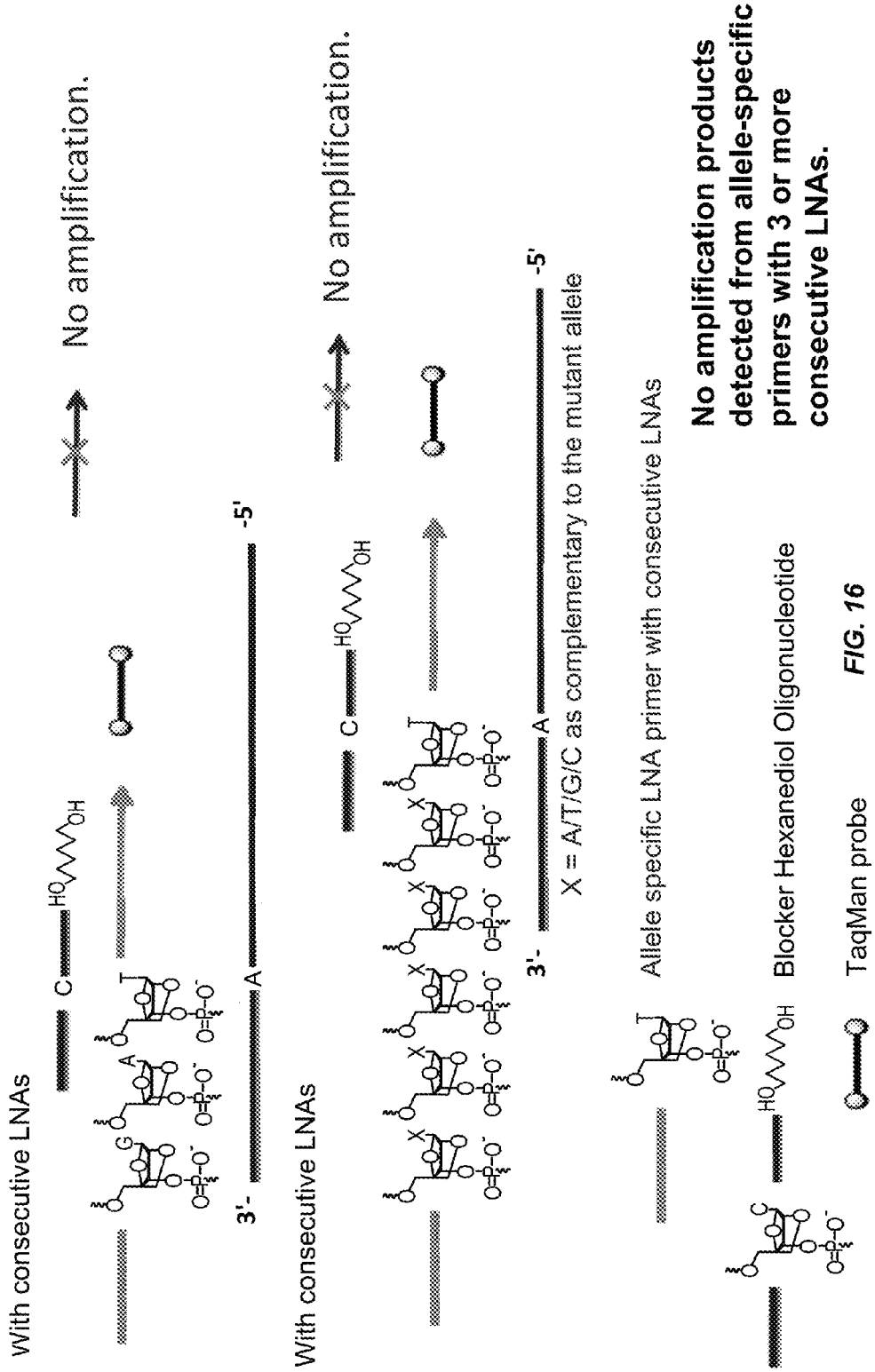
FIG. 16 shows that three or more LNA modifications placed consecutively on an allele-specific primer do not produce an amplification product.

Experiment #4 shows that consecutive LNAs on an allele-specific primer of the present invention did not generate amplification products in the assay. FIG. 16 depicts a allele-specific primer with consecutive LNAs (GAT) where T is the variant nucleotide and shows that it failed to amplify the KRAS G12A mutant allele. FIG. 16 also depicts a allele-specific primer with six consecutive LNAs (T of the variant nucleotide and 5 LNAs upstream of the T that are complementary to the mutant allele). This primer failed to detect the mutant allele in the sample and generated no amplification products in the assay.

Figure 18:
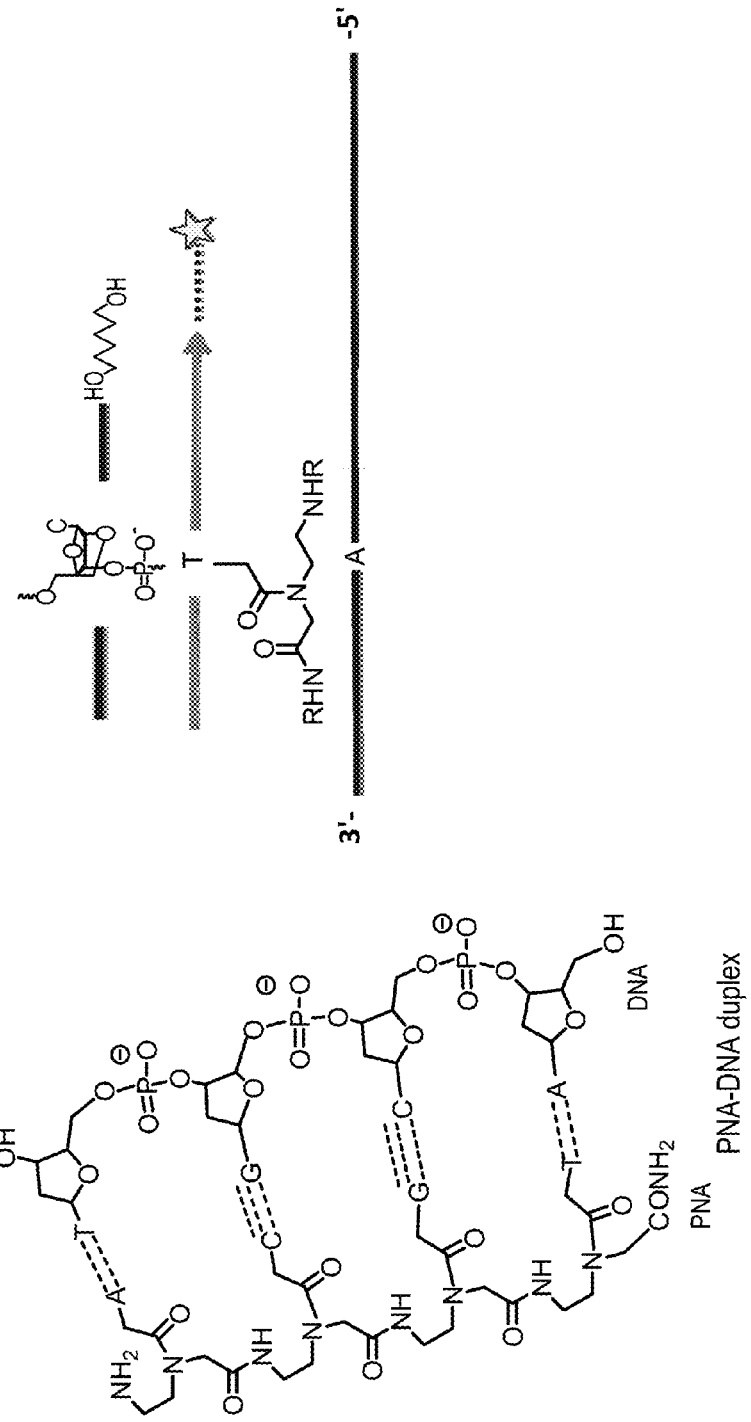
FIG. 18 shows an exemplary PNA-DNA duplex (left) and an exemplary allele-specific primer with a PNA modification (T in FIG. 18; right).
Figure 19:
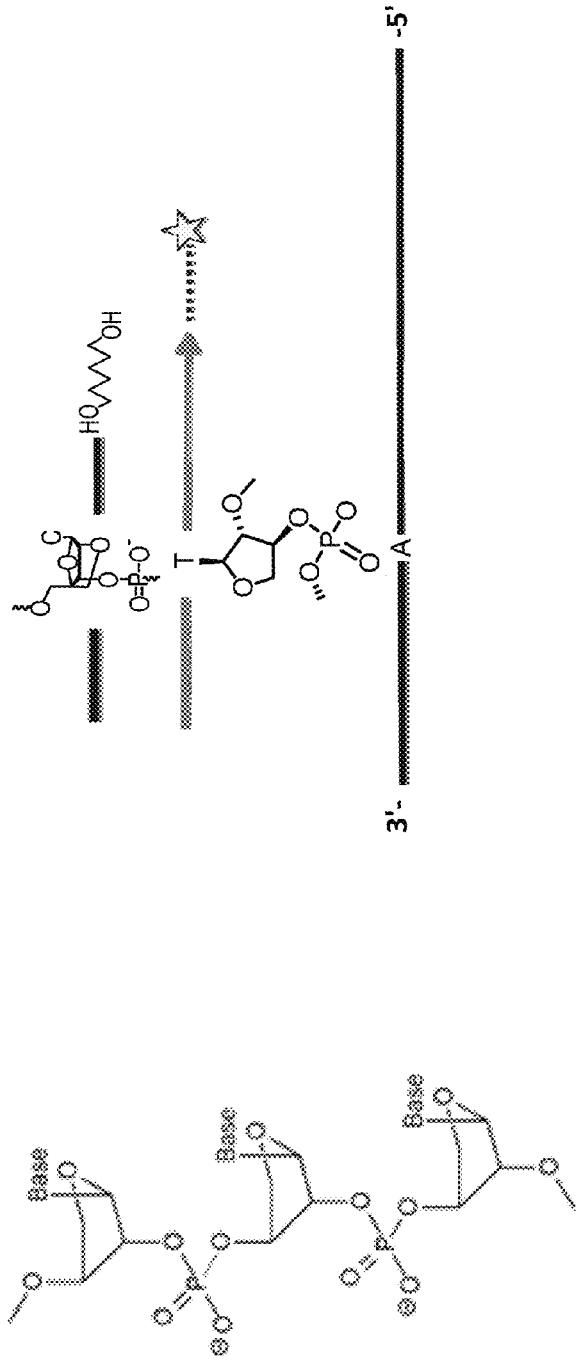
FIG. 19 shows an exemplary TNA-containing oligonucleotide (left) and an exemplary allele-specific primer with a TNA modification (T in FIG. 19; right).
Figure 20:
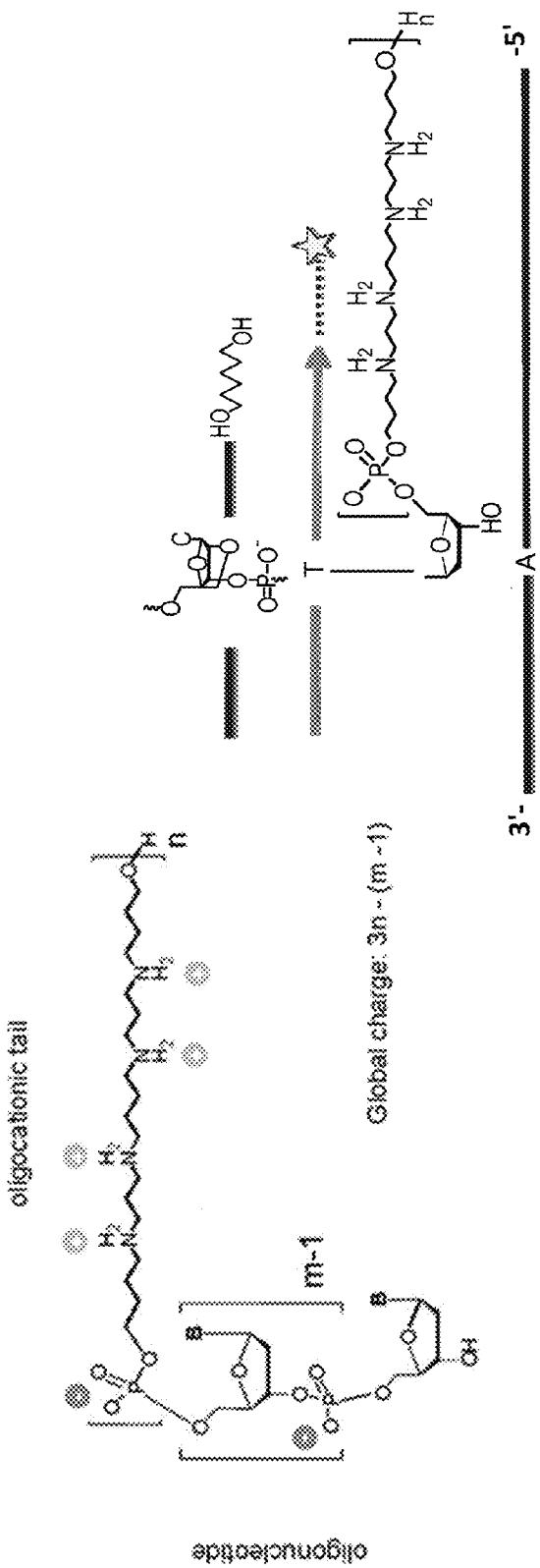
FIG. 20 shows an exemplary ZNA oligonucleotide (left) and an exemplary ZNA modified allele-specific primer (right; T in FIG. 20).

This example shows the allele-specific primer, blocker probe and detector probe of the present invention can comprise modified base(s), such as locked nucleic acid (LNA), peptide nucleic acid (PNA), α-L-threose nucleic acid (TNA), zip nucleic acid (ZNA) and triazole DNA (TzDNA). FIG. 17 shows an exemplary LNA molecule and other modified LNAs. FIG. 18 shows an exemplary PNA-DNA duplex (left) and an exemplary allele-specific primer with PNA (T in FIG. 18; right). FIG. 19 shows an exemplary TNA containing oligonucleotides (left) and an exemplary allele-specific primer with TNA (T in FIG. 19; right). FIG. 20 shows an exemplary ZNA oligonucleotide (left) and an exemplary ZNA modified allele-specific primer (right; T in FIG. 20). FIG. 21 shows an exemplary TzDNA molecule (left) and an exemplary allele-specific primer with TzDNA (right; T in FIG. 21).

Figure 22:
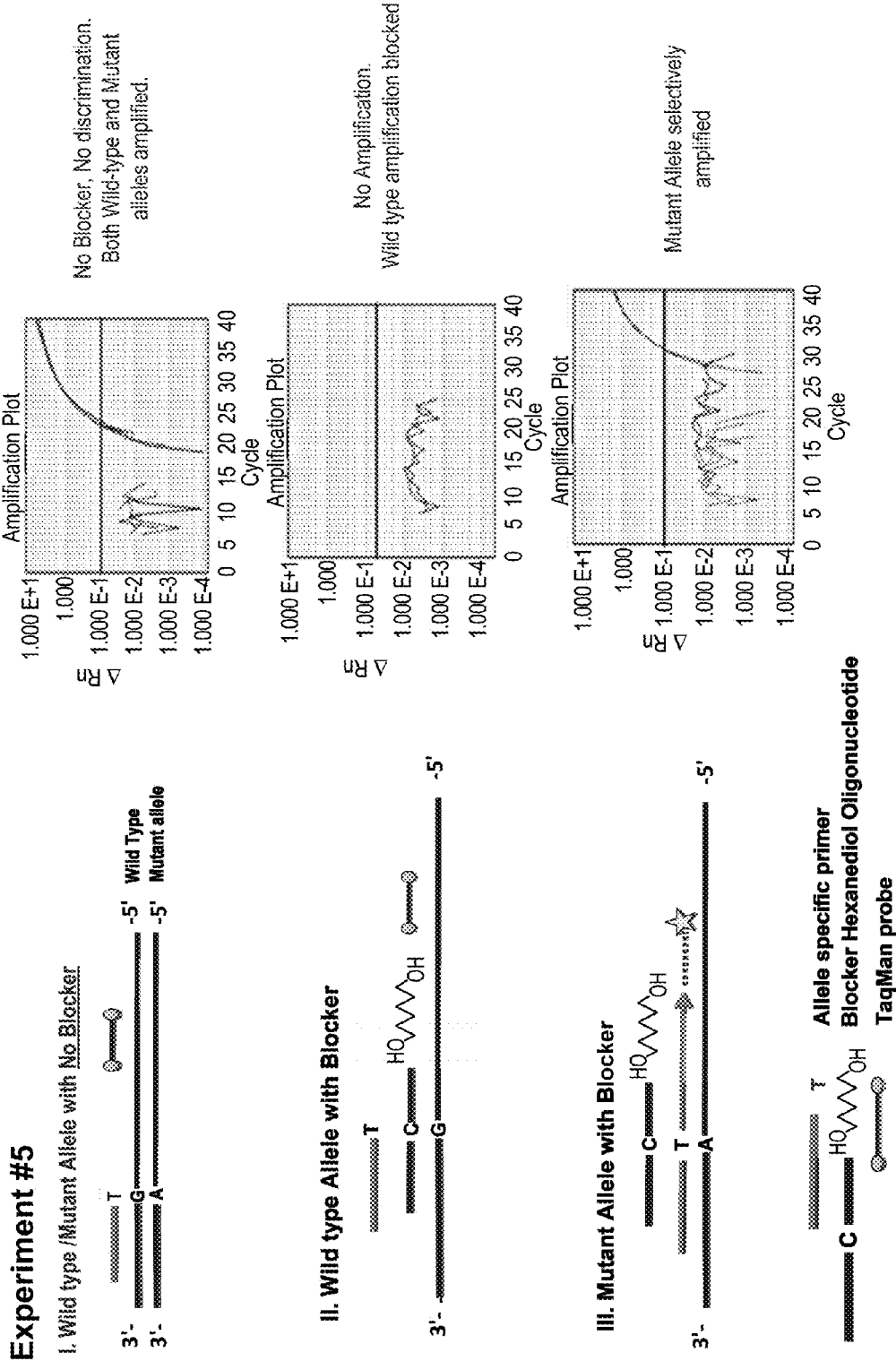
FIG. 22 illustrates an exemplary blocker probe for the G12A KRAS assay of the present invention. The blocker probe (oligonucleotides) is specifically designed to hybridize to the wild-type allele and inhibits the amplification of contaminating wild-type genomic DNA efficiently and selectively, without affecting the amplification of the allelic variant.

Experiment #5 shows that a blocker probe with a hexanediol modification at the 3' end improves the selectivity of the assay of the present invention. When the assay was performed without a blocker probe, both wild-type and mutant alleles were amplified similarly and were unable to be discriminated (part I, FIG. 22). In the embodiment of the present invention with a blocker probe, the blocker hexanediol probe hybridized to the wild-type allele of KRAS G12A SNP and hindered real-time PCR amplification (part II, FIG. 22). In this assay the mutant allele was selectively amplified (part III, FIG. 22).

Experiment #6 shows that the KRAS G12A assay of the present invention comprising an allele-specific primer with LNA, a blocker probe with hexanediol, Taqman probe and reverse primer generated an amplification product specific to the mutant allele (positive control) and not to the wild-type allele. Part I, FIG. 23 shows that the mutant allele-specific primer amplified both the wild-type and mutant alleles of the KRAS G12A SNP. Part II, FIG. 23 shows that the mutant allele-specific primer with a single LNA at the variant nucleotide located at the 3' end of the primer amplified the mutant allele and not the wild-type.

Figure 24:
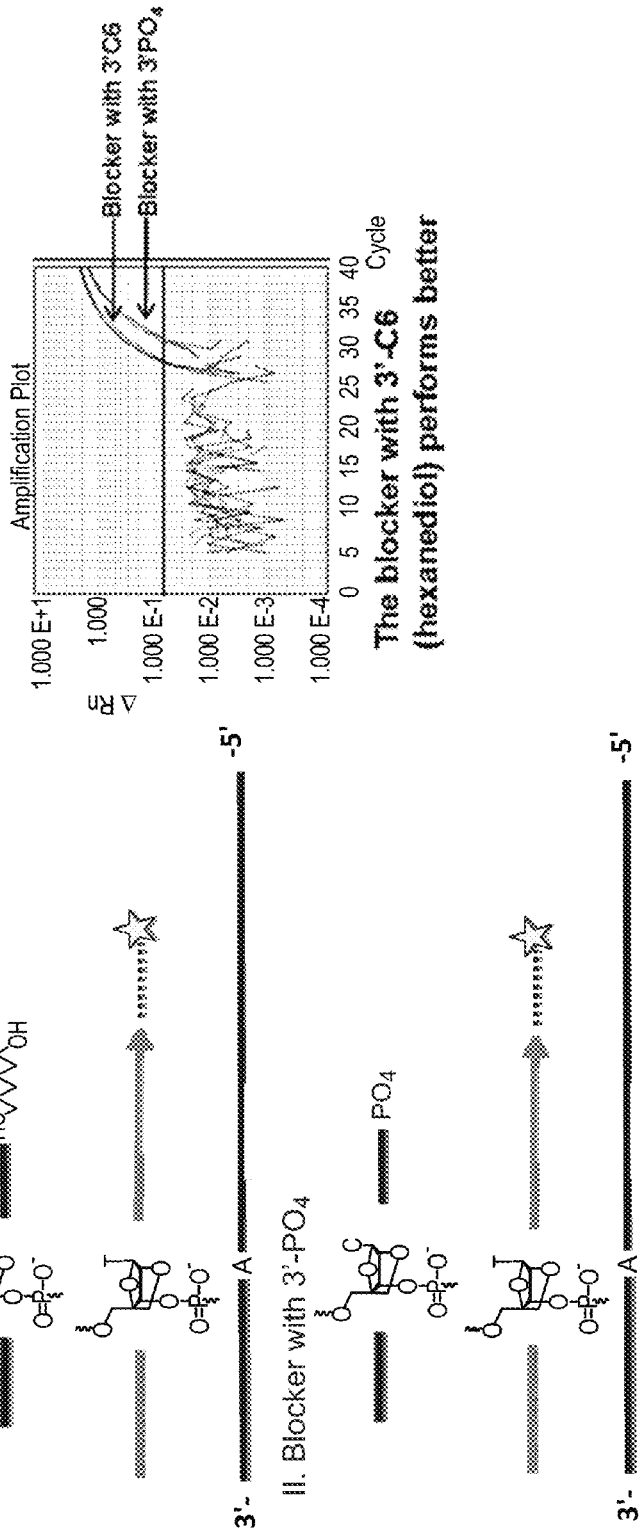
FIG. 24 shows a comparison between a blocker probe with a hexanediol modification (3' carbon tail) and one with a phosphate group. The blocker hexanediol probe performed better with a lower Ct of 28.4, compared to a Ct of 31.2 for the phosphorylated blocker.

Experiment #7 demonstrates a blocker probe with a hexanediol (C6) modification at the 3' end of the oligonucleotide performed better than a probe with a 3'-phosphate group ($PO_4$) in a KRAS G12A assay for the present invention comprising an allele-specific primer with LNA at the variant nucleotide. FIG. 24 shows that the assay with the blocker hexanediol probe performed better with a lower Ct than the assay with the blocker $PO_4$ probe (Ct of 28.4 vs. Ct of 31.2). The flexibility of the hydrophobicity of the carbon chain allows the hexanediol blocker to hybridize well without being sterically hindered. Although the phosphate groups at the 3' end of the blocker probe also can bind the wild-type allele, the efficiency of binding may be diminished by the bulkiness and the ionic nature of the phosphate group.

Experiment #8 demonstrates that a blocker probe with LNA performed better in the assay of the present invention compared to a blocker probe without LNA. FIG. 25 illustrates that a blocker LNA probe had a lower Ct value than a blocker probe without LNA. The methods of the present invention comprising a blocker probe with LNA and hexanediol modification can produce efficient and selective amplification of allelic variants, thereby improving allelic discrimination.

Figure 26:
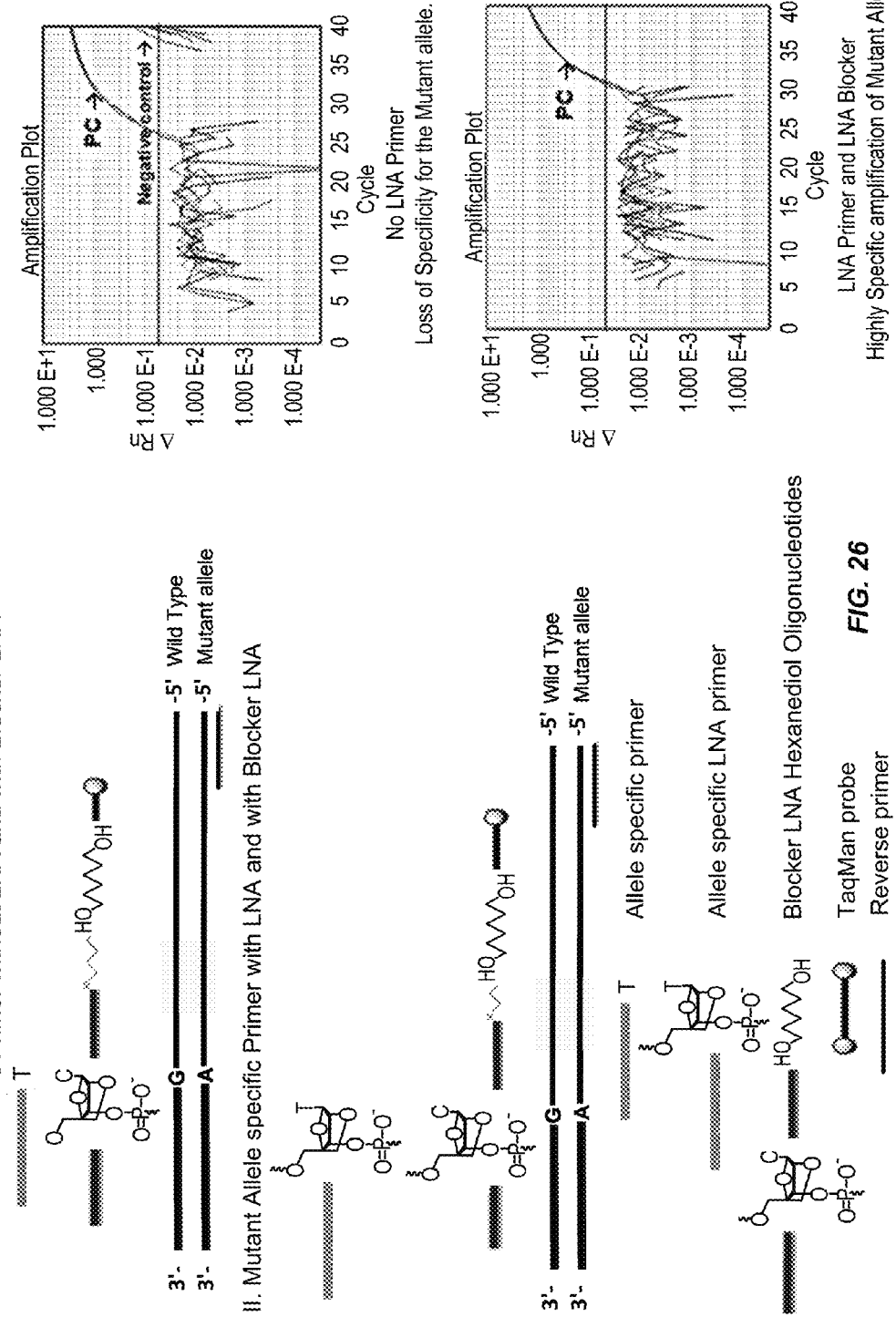
FIG. 26 shows that an exemplary method of the present invention that uses LNA-containing allele-specific primer and LNA-containing blocker probe had high specificity for the mutant allele and generated a specific amplification product.

Experiment #9 shows that LNAs in the mutant allele-specific primer and the blocker probe of the present invention resulted in highly specific amplification of the mutant allele of the KRAS G12A SNP. FIG. 26 shows that the assay with the LNA primer and LNA blocker amplified the mutant allele (positive control) and not the wild-type allele (negative control).

Experiment #10 shows that LNA can be strategically placed on the blocker probe sequence to improve the performance of the SNP assay of the present invention. FIG. 27A shows the components of the assays tested in the experiment. As depicted in FIG. 27B, Blocker.1.LNA and Blocker.4.LNA have the same blocker sequence, but the locations of the LNA modifications are different. Blocker.1.LNA has LNAs at the 5' end and at the allelic variant nucleotide, while Blocker.4.LNA has LNAs at the 5' end and at the 3' end of the sequence. The assay with Blocker.1.LNA displayed better allelic discrimination and a lower Ct compared to the assay with Blocker.4.LNA (FIG. 27C).

Figures 28A, 28B:
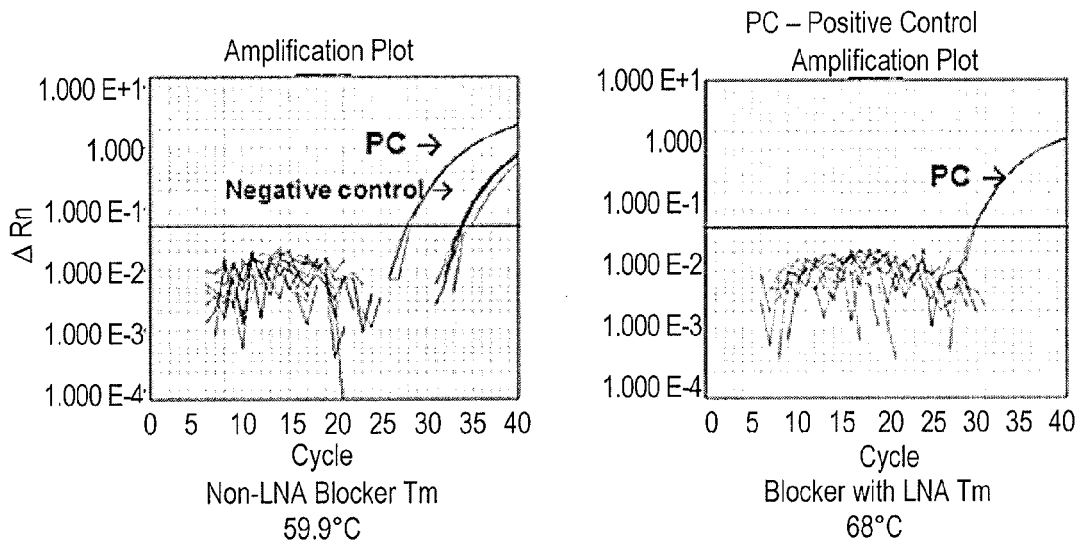
FIG. 28A shows the influence of Tm of the blocker probe (SEQ ID NOS:12 and 11, respectively) on the performance of the assay.
FIG. 28B also shows the difference in Tm and Ct value between a blocker without LNA and one with two LNAs. The increase in Tm due to the presence of LNA, consequently improves the sensitivity and selectivity of the assay of the present invention. With the higher Tm, the blocker probe remained annealed to its target during extension, thereby efficiently blocking the wild-type allele from interfering with amplification and allowing the variant to be amplified preferentially and selectively. The Tm of the same blocker sequence increased from 59.9° C. to 68° C. with the addition of two LNAs.

FIG. 28A shows the influence of Tm of the blocker probe on the performance of the assay. Blocker.1.LNA has a Tm of 59.9° C. Blocker.4.LNA has a Tm of 68° C. FIG. 28B also shows the difference in Tm and Ct value between a blocker without LNA and one with two LNAs. In assays of the present invention a blocker probe with LNA and a higher Tm has better specificity for the allelic variant, better sensitivity, and efficient inhibition of the wild-type variant.

Figure 29:
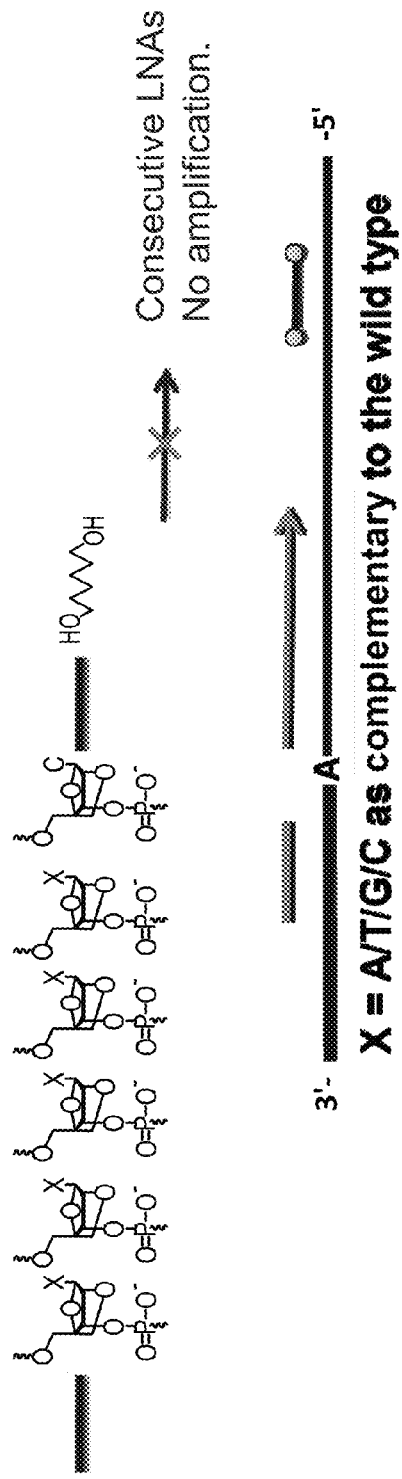
FIG. 29 shows that the placement of 6 consecutive LNA modifications including an LNA located at the allele-specific nucleotide position on the blocker probe completely arrested amplification during PCR cycling.

Experiment #11 shows that consecutive LNAs on a blocker probe of the present invention completely block amplification of the mutant variant, thereby significantly decreasing the performance of the assay. FIG. 29 shows that the placement of 6 consecutive LNAs (cytosine (C) complementary to the wild-type variant (G) and 5 bases up complementary to the wild type allele) on the blocker probe completely arrested amplification during PCR cycling.

FIG. 30 shows that the ΔCt values can be used to determine the feasibility of the assay and its selectivity. The higher ΔCt value obtained with the LNA-containing primers and probes indicate the increased feasibility and selectivity of the assay of the present invention. FIG. 31 shows how the ΔΔCt values are calculated from the Ct values from various somatic mutation genotyping assays. Assay A of the figure that was designed with an LNA-containing primer and blocker performed better than the other assays that contained primers and probes with consecutive LNAs.

In sum, this example shows that the use of nucleic acid modifications such as modified bases (e.g., LNA) in allele-specific primers and blocker probes improves the performance of the genotyping assay of the present invention. Likewise, the selectivity and sensitivity for allelic variant discrimination increases.

Example 6

Quantitation of the Percentage of Allelic Variant Present in the Unknown Sample Using Somatic Mutation Genotyping Assays This example illustrates the use of the allele-specific primers, allele-specific blocker probes, and detector probes containing modified bases to quantitate the allelic variants for E545K of the PIK3CA gene, G12D of the KRAS gene, E746-A750 deletion of the EGFR gene, or V600E of the BRAF gene. This example also illustrates that the methods of the invention are highly selective in differentiating and quantitating the mutant variant from the wild-type variant. Additionally, the example shows that the assays of the present invention are linear and can be used to determine quantitative information of the allelic variant.

Somatic mutation genotyping assays were performed using methods described herein. Allele-specific primers and allele-specific blocker probes of the present invention containing modified bases, nucleic acid analogs, and/or blocker moieties were used to detect for the presence of the various allelic variants of the PIK3CA, EGFR, KRAS and BRAF genes. Table 1 lists the mutations on the aforementioned genes.

TABLE 1

| Gene | Mutation | Positive Cell Line | Source |
| --- | --- | --- | --- |
| PIK3CA | E542K | SW 948 | ATCC |
|  | E545D | Sup T1 | ATCC |
|  | E545K | MCF 7 | ATCC |
|  | H1047R | KPL 4 | ATCC |
| EGFR | T790M | H1975 | ATCC |
|  | L858R | H1975 | ATCC |
|  | E746-A750 deletion | H1650 | ATCC |

TABLE 1-continued

| Gene | Mutation | Positive Cell Line | Source |
| --- | --- | --- | --- |
| KRAS | G12A | SW 1116 | ATCC |
|  | G12C | NCI-H23 | ATCC |
|  | G12D | LS 174T | ATCC |
|  | G12R | PSN1 | ATCC |
|  | G12S | A 549 | ATCC |
|  | G12V | SW 403 | ATCC |
|  | G13C | H 1734 | ATCC |
|  | G13D | T 84 | ATCC |
| BRAF | Q61H | H 460 | ATCC |
|  | V600E | HT 29 | ATCC |

In order to quantitate the amount of an allelic variant present in a given sample, a standard curve was generated. The standard curve was made for each mutation from a cell line positive for that specific mutation. Because the standard curve is linear, it can be used to quantitate the allelic variant in an unknown sample. Table 1 shows the allelic variants and the positive cell lines used to create the standard curve. DNA from the cell lines were extracted using Qiagen's DNeasy Blood & Tissue Kit. A series of dilutions of DNA (e.g., 100, 10, 1, 0.1 and 0.01 ng) from each positive cell line was made to create an allele-specific standard curve. In this example standard curves for E545K of PIK3CA, G12D of KRAS, E746-A750 deletion of EGFR, and V600E of BRAF were made.

An allele-specific calculator (e.g., mathematical analysis) was established from the standard curve generated and on the assumption that the positive cell line has a percent mutation of 100%. For some of the cell lines the % mutation was determined by using an allele-specific primer that preferentially hybridizes to the wild-type allele.

To determine the amount of mutation in an unknown sample, the sample was assayed using the methods of the present invention. Then, the Ct value for the allelic variant of the sample was analyzed using the percent mutation calculator to determine the amount and percent of the variant present in the sample.

FIG. 32A shows that the standard curve for the PIK3CA E545K allelic variant and the MCF 7 cell line. It was created using methods described herein. The standard curve plot of Ct value versus DNA amount was linear in $\log_{10}$ scale. FIG. 32B shows amplification curves for two unknown samples from patients with colorectal cancer (Samples A and B) and the positive control (MCF 7 cell line) generated using the genotyping assay. FIG. 32C shows the amount and the percentage (percent mutation) of the mutant variant E545K present in the samples. The amount and the percent (percent mutation) of the allelic variant present in the samples was determined using the calculator (FIG. 32C). In particular, the percent mutation was calculated from the amount of mutation with respect to the starting amount of DNA in the sample. It was determined that Sample A has a percent mutation of 15% for the PIK3CA E545K variant, relative to the positive control. Sample B has a percent mutation of 7.3% for the same variant, relative to the positive control. Notably, the mutant allele was detected in 20 ng of DNA from Sample B.

Figures 33A, 33B, 33C:
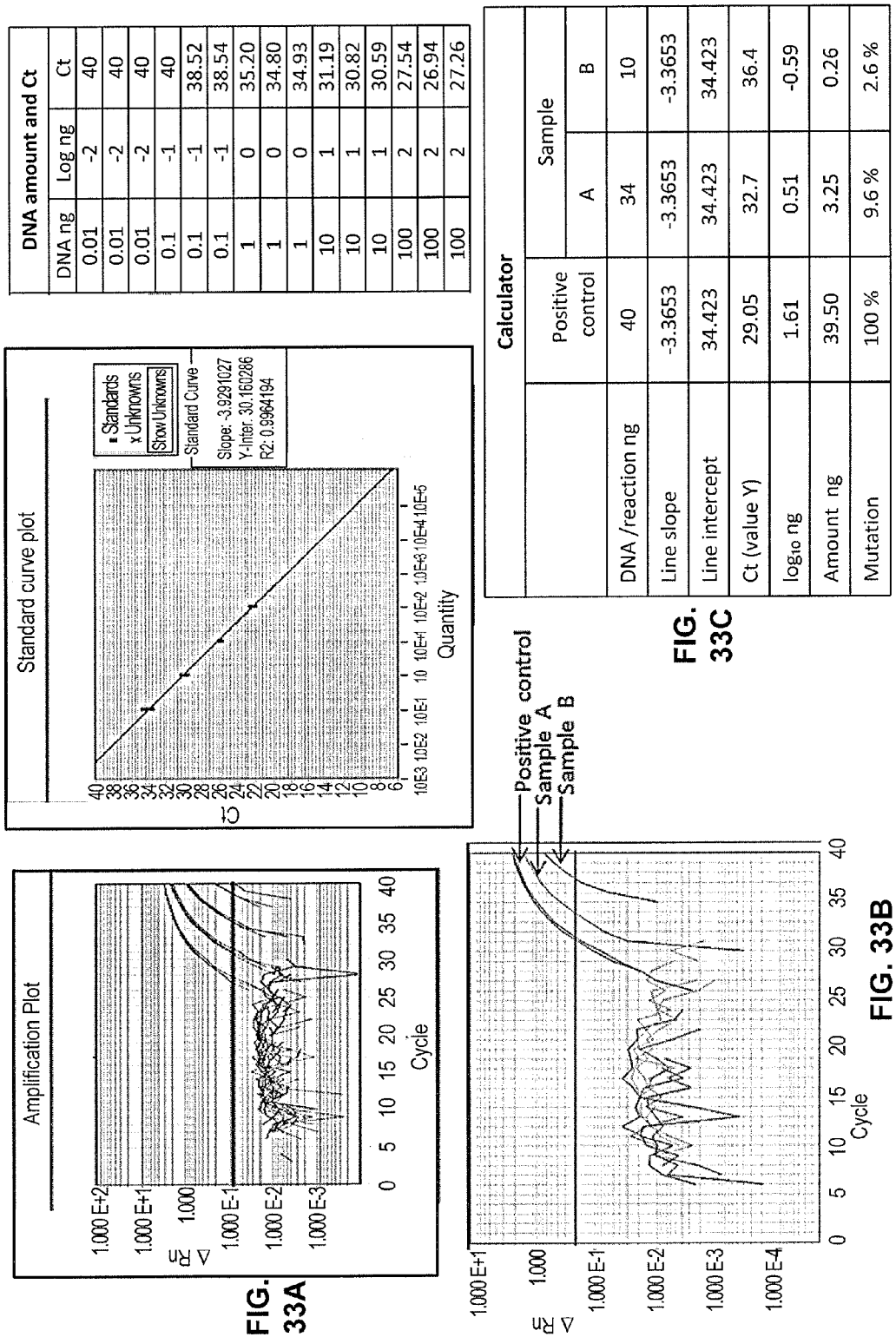
FIGS. 33A-C illustrate the use of the KRAS G12D assay of the present invention to quantify the percentage of the mutant variant present in an unknown sample.

FIG. 33 illustrates the use of the KRAS G12D assay of the present invention to quantify the percentage of the mutant variant present in an unknown sample. The standard curve plot was linear in $\log_{10}$ scale and was used to quantitate the amount and percent mutation of the unknown samples. FIG. 33A shows the amplification plot and the standard curve for the KRAS G12D genotyping assay and the LS 174T cell line. FIG. 33B shows that amplification plots for two unknown samples from patients with pancreatic cancer (Samples A and B) and a positive control (LS 174T cell line) that were generated using methods of the present invention. FIG. 33C shows the amount of DNA in Sample A expressing the mutant variant was calculated to be 3.25 ng or 9.6%, relative to the positive control.

FIG. 34 illustrates the use of the EGFR E746-A750 deletion EGF assay of the present invention to quantify the percentage of the mutant variant present in an unknown sample. FIG. 34A shows the amplification plot and standard curve for the E746-A750 deletion of the EGFR gene for the H1650 cell line. FIG. 34B shows that the amplification plot for an unknown sample (Sample A) from a patient with lung cancer and a positive control (H1650 cell line) that were generated using methods of the present invention. FIG. 34C shows the amount of DNA in Sample A expressing the EGFR deletion variant was calculated to be 3.25 ng or 9.6%, relative to the positive control.

Figure 35A:
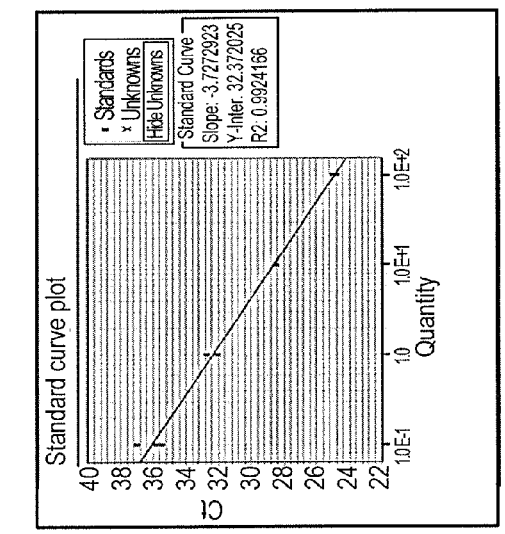
FIGS. 35A-C illustrate the use of the V600E BRAF assay of the present invention to quantify the percentage of the allelic variant present in an unknown sample.
Figure 35B:
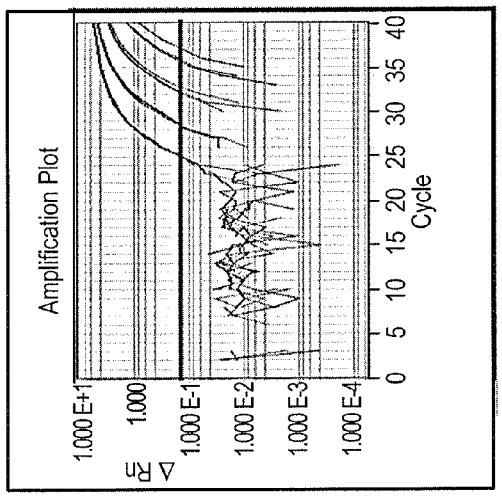
Figure 35C:
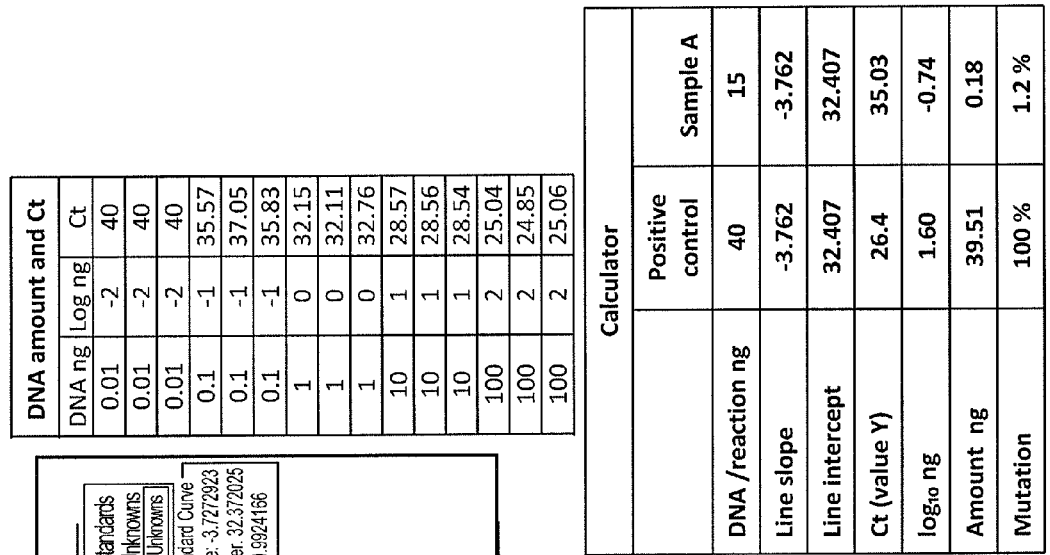

FIG. 35 illustrates the use of the V600E BRAF assay of the present invention to quantify the percentage of the allelic variant present in an unknown sample. FIG. 35A shows the amplification plot and standard curve for the BRAF V600E allelic variant for the HT 29 cell line. FIG. 35B shows that the amplification plot for an unknown sample (Sample A) from a patient with lung cancer and a positive control (H1650 cell line) that were generated using methods of the present invention. FIG. 35C shows the amount of DNA in Sample A expressing the V600E variant of BRAF was calculated to be 0.18 ng or 1.2%, relative to the positive control.

This example shows that the assays of the present invention (e.g., PIK3CA E545K, KRAS G12D, EGFR E746-A750 deletion, and BRAF V600E genotyping assays) are linear in $\log_{in}$ scale and can be used to determine quantitative information about an allelic variant in a patient tissue sample.

Example 7

Determining Tumor Genetic Heterogeneity

This example illustrates a correlation between the level of a cancer biomarker and the percent mutation for a particular allelic variant of an oncogenic gene. In gastric tumor samples, a high level of cytokeratins (CK), detected using a Collaborative Enzyme Enhanced Reactive (CEER) immunoassay, corresponded to a high percent mutation for the KRAS G13D allelic variant. In pancreatic tumor samples, a high CK level correlated to a percent mutation of 100% for the KRAS G12D allelic variant. This example illustrates that the tumor content of a tissue sample can be assessed using the genotyping assay of the present invention and a CEER immunoassay (also known as COP1A; see, e.g., PCT Patent Publication Nos. WO 2008/036802 and WO 2009/108637, the disclosures of which are herein incorporated by reference in their entirety for all purposes).

Figure 36A:
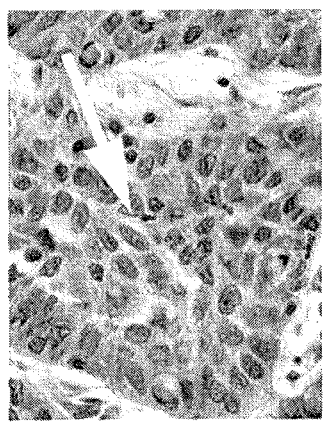
FIGS. 36A-B show H&E stained frozen sections of a non-small cell lung cancer (NSCLC) tumor sample.
Figure 36B:
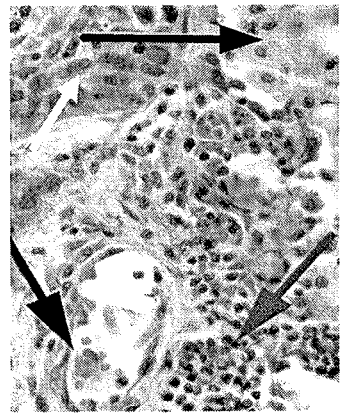

Tumor tissue samples are often a mixture of tumor and non-tumor cells (e.g., blood or adjacent non-tumor tissue). Tumor cells in a solid cancer tissue sample can be assessed by hematoxylin and eosin (H&E) staining. FIG. 36 shows H&E stained frozen sections of a non-small cell lung cancer (NSCLC) tumor sample. FIG. 36A shows a section with a high percentage of tumor cells (the white arrow indicates tumor cells). FIG. 36B shows a section composed of a mixture of tumor cells (white arrow), stroma with blood vessels (black arrow), inflammatory cells (e.g., lymphocytes; red arrow); and a lung alveolus filled with macrophages (green arrow).

Cytokeratins were used as a biomarker to detect tumor cells. High CK levels were observed in tumor samples, while lower levels were detected in adjacent normal tissue. We evaluated the levels of CK and the percent mutation of KRAS, EGFR, and PIK3CA allelic variants in various gastric and pancreatic tumor samples to determine whether higher CK levels correlates to a higher percent mutation for a particular mutant allele.

FIG. 37A illustrates that in gastric tumor samples both a high CK level and a low percent mutation for the EGFR T790M, KRAS G12V, KRAS Q61H, or PIK3CA E545K variant indicate that not all of the tumor cells are likely to carry the SNP. FIG. 37A also shows that a high CK level with a high KRAS G13D percent mutation (e.g., 90%) indicated that most of the tumor cells in the sample are likely to carry the mutation. FIG. 37B shows that a high level of CK correlates with a high percent mutation (100%) for the KRAS G12D variant in a pancreatic tumor sample.

In sum, this example shows that the genotyping assays of the present invention can be used to calculate the percent mutation of a patient's tumor sample. This example further illustrates that the percent mutation of a specific allelic variant of an oncogenic gene can be correlated to the expression level of a cancer biomarker.

Example 8

Sensitivity of the Somatic Mutation Genotyping Assay in Discriminating Tumor Cells in Whole Blood Samples In this example, the sensitivity of the somatic mutation genotyping assays of the present invention were determined by performing assays for the G12A or G12S mutation of KRAS on whole blood samples spiked with tumor cells carrying the mutation. Allele-specific primers and allele-specific blocker probes of the present invention containing modified bases such as LNA modifications were used to detect for the presence of the KRAS G12A or G12S variant allele. This example also compares the sensitivity of the somatic mutation genotyping assays of the present invention and Life Technologies' castPCR™ Mutation Assay.

The sensitivity of the KRAS G12A assay of the present invention (e.g., "Inventive Somatic Mutation Genotyping Assay") was tested by determining the minimum amount of positive tumor cells (e.g., SW116 cell line) needed to detect the KRAS mutation in a whole blood sample. The test samples comprised of whole blood spiked with cells of the SW116 cell line (e.g., either 100,000; 10,000; 1,000; 500; 250; 100; 50; 10 or 0 tumor cells per sample). Genomic DNA from the test samples were extracted using Qiagen's DNeasy Blood & Tissue Kit. The assays of the present invention were performed using the methods indicated herein. FIG. 38A illustrates the amplification curves generated from the KRAS G12A assay of the present invention. FIG. 38B illustrates the amplification curves from Life Technologies' castPCR™ Mutation Assays performed on the same test samples.

As shown in FIG. 38C, the genotyping assay of the present invention detected the G12A mutation when the test sample contained as few as 250 positive tumor cells. By comparison, a minimum of 1,000 tumor cells in the sample were needed for the castPCR™ assay. The results show that the assay of the present invention has greater sensitivity than the castPCR™ assay for detecting the G12A KRAS mutation in whole blood samples.

To evaluate the KRAS G12S assay of the present invention, whole blood samples were spiked with cells of the A549 cell line (e.g., either 100,000; 10,000; 1,000; 500; 250; 100; 50; 10; or 0 positive tumor cells in the test sample of whole blood). Using Qiagen's DNeasy Blood & Tissue Kit, genomic DNA of the test samples were extracted. The presence of the KRAS G12S variant was detected using the assay of the present invention and Life Technologies' castPCR™ assay. The sensitivity of the assays was compared. FIG. 39A shows the amplification curves of the test samples using the assay of the present invention. FIG. 39B shows the amplification curves for Life Technologies' castPCR™ Assay.

The assays of the present invention detected the G12S mutation in samples with as few as 100 tumor cells (FIG. 39C). CastPCR™ was 10-fold less sensitive; the assay detected the mutation in test samples containing 1,000 or more positive tumor cells. FIG. 39C illustrates that the genotyping assay of the present invention has greater sensitivity than castPCR™ for the detection of the G12S KRAS mutation in whole blood samples.

In sum, this example demonstrates that the somatic mutation genotyping assays of the present dramatically improve the allelic PCR assay compared to the castPCR™ assay from Life Technologies.

Example 9

Exemplary Somatic Mutation Genotyping Assays for Detection of Allelic Variants and Determining the Percentage of the Variant in a Sample This example illustrates the methods of the present invention for detecting an oncogenic single nucleotide polymorphism (SNP) in a sample and quantitating the percent mutation of the SNP in the sample. This example also illustrates the screening of samples (e.g., cancer cell lines and tissue from patients with cancer) for the presence of rare (e.g., mutant) variant alleles of using the allele-specific primers and allele-specific blocker probes of the present invention containing modified bases. In particular, the allele-specific primer comprises a locked nucleic acid (LNA) at the 3'-end that is specific for the variant allele and the allele-specific blocker probe comprises a hexanediol blocker moiety at the 3'-end and a LNA at a position in the middle of the oligonucleotide sequence that is specific for the wild-type allele. In this example, the allelic variants detected include PIK3CA E542K, E545D, E545K and H1047R; EGFR T790M, L858R and E746 deletion; KRAS G12C, G12R, G12S, G12D, G12A, G12V, G13C, G13D, and Q61H; and BRAF V600E. This example also shows that the methods of the invention can be used with various samples from cancers and tumors such as breast cancer, colorectal cancer, lung tumor, gastric tumor, liver tumor, colon tumor, and pancreatic tumor; cell lines (e.g., colorectal cancer cell line) and xenograft tissue.

The presence of various SNPs was determined and the percentage of the detected variant in the sample was quantitated using methods of the present invention, such as allele-specific real time PCR assays, establishing standard curves from assays performed on cell lines expressing the variant, and creating a percent mutation calculator for each variant. Briefly, to establish a standard curve for an allelic variant, SNP detection assays of the invention were performed using serial dilutions of cell lines positive for the allelic variant. The results of the assays were used to make a standard curve, and then a percent mutation calculator for the allelic variant was created that can predict the amount of the allelic variant present in a sample based on data from the SNP detection assay obtained for the sample.

FIG. 40 shows the results obtained by using the methods of the present invention to detect (e.g., presence or absence) and/or quantitate (e.g., percent mutation) the following SNPs in breast cancer samples: PIK3CA E542K, E545D, E545K, H1047R; EGFR T790M, L858R; KRAS G12A, G12C, G12D, G12R, G12S, G12V, and G13D; and BRAF V600E. It was determined that the PIK3CA H1047R SNP was expressed at different percentages in the samples. For instance, test #1 expressed H1047R allele at 12%, while test #33 expressed the same SNP at 41%. Test #2 expressed the mutant variant at 1%. Test #34 expressed another PIK3CA SNP (e.g., E545K) at 100%, which predicts that all cells in the test sample have the E545K variant.

FIG. 41 shows that PIK3CA SNPs (E542K, E545D, E545K and H1047R) were also detected and quantitated in another set of breast cancer samples. 45 breast cancer samples were screened for the PIK3CA E542K, E545D, E545K and H1047R allelic variants. The percent mutation of the variant was quantitated using methods described above and in Example 6. The results show that sample #744 expressed E542K at a very low percentage (e.g., 0.13%) and that sample #743 expressed H1047R at a high percentage of 100%. Other samples that expressed the E542K variant were sample #762 at 2% and sample #767 at 3.55%. Other samples that expressed the H1047R variant were samples #746 with 89% mutation, #775 with 51.8% mutation, #740 with 6.8% mutation and #769 with 5.9% mutation.

FIG. 42 shows that lung tumor samples can be screened for SNPs using methods of the present invention. In this embodiment, the presence and percent mutation of various SNPs were determined in 25 lung tumor samples. The SNPs included PIK3CA E542K, E545D, E545K and H1047R; EGFR T790M, L858R and E746 deletion; KRAS G12C, G12R, G12S, G12D, G12A, G12V, G13C, G13D, and Q61H; and BRAF V600E. Samples #352-355 all expressed PIK3CA E545K at 100% which indicates that all cells in these samples have the mutant variant. Samples #371-375 and 381 all expressed EGFR L848R at 100%. The EGFR E746 deletion variant was detected in two samples (#164 and #381) at very low rates (0.1% and 0.2%, respectively). The only sample in the set that expressed the BRAF V600E variant was sample #213 which had a mutation percentage of 0.2%.

FIG. 43 illustrates the results obtained from using the methods of the present invention on an additional 32 human lung tumor samples. The SNPs included PIK3CA E542K, E545D, E545K and H1047R; EGFR T790M, L858R and E746 deletion; KRAS G12C, G12R, G12S, G12D, G12A, G12V, and G13D; and BRAF V600E. Sample #9 of this set expressed the KRAS mutations KRAS at 0.3%, G12V at 2% and G13D at 0.3%. Samples #3 and 12 expressed the PIK3CA E545K variant at 100%. Sample #25 expressed PI3KCA E545D at 0.2% and sample #6 expressed PIK3CA H1047R at 0.06%. Samples #13 and 19 had KRAS G12C at 100%, while sample #22 had the same variant at only 2%. Sample #22 also expressed the BRAF V600E variant at 54%. The KRAS G12V variant was present in sample #14 at a percentage of 100% and in sample #15 at 0.1%. The BRAF V600E variant was detected in samples #4 and 31 at 47% and 34%, respectively.

FIG. 44 shows that gastric tumor samples can be screened using methods of the present invention. The SNPs included PIK3CA E542K, E545D, E545K and H1047R; EGFR T790M, L858R and E746 deletion; KRAS G12C, G12R, G12S, G12D, G12A, G12V, G13D, and Q61H; and BRAF V600E. In this embodiment, each assay was run with 40 ng of sample (e.g., DNA). Of the 17 samples assayed, sample #233 expressed four KRAS mutations, such as G12R at 0.001%, G12V at 2.3%, G13D at a "low" percentage, and Q61H at 0.5%. The KRAS G12C variant was detected at "low" percentage in sample #241. The PIK3CA E542K allele was detected in sample #253 at 0.6% and the EGFR T790M allele was detected in sample #223 at 0.2%. Compared to other tumor samples such as breast cancer and lung tumor, the percent mutation of the SNPs in the gastric tumor samples tested was not higher than at 100% for any of the allelic variants screened.

FIG. 45 shows the results obtained from using the methods of the invention with xenograft samples. The SNPs included PIK3CA E542K, E545D, E545K and H1047R; EGFR T790M, L858R and E746 deletion; KRAS G12C, G12R, G12S, G12D, G12A, G12V, G13C, G13D, and Q61H; and BRAF V600E. The EGFR E746 deletion was present in samples #585-588 and predicted to be in 100% of the cells in the sample. The PIK3CA H1047R allele was detected in samples #581-584 at a percentage mutation of 3.4%, 1.2%, 1% and 1.8%, respectively.

FIG. 46 illustrates that KRAS, BRAF and PIK3CA allelic variants can be detected and quantitated in colorectal cancer samples using the methods of the present invention. The SNPs included PIK3CA E542K, E545D, E545K and H1047R; KRAS G12C, G12R, G12S, G12D, G12A, G12V, and G13D; and BRAF V600E. The data shows that sample #121 expressed the KRAS G13D variant at 6% and PIK3CA E545K at 58%. Sample #130 expressed the KRAS G13V variant at 54% and PIK3CA E542K at 5%.

FIG. 47 also illustrates that KRAS, BRAF and PIK3CA allelic variants can be detected and quantitated in additional colorectal cancer samples using the methods of the invention. The data shows that sample #147 expressed the KRAS G12D and PIK3CA variants at 100%, indicating that all cells in the sample are predicted to express the variants. Sample #149 expressed the KRAS G13D variant at 24% and PIK3CA H1047R at 0.1%. Sample #163 expressed KRAS G12D at 34% and PIK3CA E542K at 3%.

FIG. 48 illustrates that liver tumor and colon tumor tissues from patients with colorectal cancer can be screened for KRAS, BRAF and PIK3CA allelic variants using the methods of the present invention. The results shows that some of the samples had a plurality of SNPs. For instance, Samples #207 and #208 expressed KRAS G12S and PIK3CA E545K. Using methods of the present invention, it was also determined that sample #207 expressed G12S at 22% and sample #208 expressed the same variant at 63%. Sample #207 expressed the E545K variant at 40% and sample #208 expressed the same variant at 79%. Sample #215 had BRAF V600E at 1% and PIK3CA E545K at 5%. Sample #216 had BRAF V600E at 9% and PIK3CA E545K at 23%. Sample #217 expressed KRAS G12V at 2% and PIK3CA 545K at 5%. Sample #217 had KRAS G12V at 4% and PIK3CA 545K at 9%.

FIG. 49 illustrates that samples from patients with pancreatic cancer can be screened for SNPs and the percent mutation can be determined according to methods of the present invention. In this embodiment, fine needle aspirate samples were from obtained from patients and screened using SNP genotyping assays described herein. In the pancreatic cancer samples tested, various KRAS mutations were detected, but PIK3CA (e.g., E542K, E545D, E545K, H1047R), EGFR (e.g., T790M, L858R) and BRAF (e.g., V600E) mutations were not detected. Sample #28 expressed the KRAS G12C variant. The KRAS G12V variant was present in #19, 21, 26, 27 and 35, at percentage mutations of 63%, 0.2%, 4%, 1% and 3%, respectively. Samples #9 and 11 expressed the KRAS G12D variant at 100%. This variant was also expressed in samples #2, 6, 12, 23, 24, 37, 39 and 40 at 1.1%, 29%, 7.4%, 5%, 5%, 32%, 5.4% and 0.9%, respectively. The SNPs screened were not detected in the other pancreatic tumor samples in the set.

In sum, this example demonstrates that the somatic genotyping assays of the present invention can be used to detect and/or quantitate allelic variants in genes such as KRAS, PIK3CA, EGFR and BRAF. The examples shows that the methods of the present invention can be used to detect a plurality of allelic variants in cancer and tumor tissue samples from patients. Furthermore, the percentage of the allelic variant in the sample can be determined.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for detecting or quantitating a first allelic variant of a target sequence in a nucleic acid sample suspected of having at least a second allelic variant of the target sequence, said method comprising:
   (a) forming a reaction mixture by combining:
      (i) the nucleic acid sample;
      (ii) an allele-specific primer, wherein an allele-specific nucleotide portion of the allele-specific primer is complementary to the first allelic variant of the target sequence, and wherein the allele-specific primer comprises at least one nucleic acid modification;
      (iii) an allele-specific blocker probe that is complementary to a region of the target sequence comprising the second allelic variant, wherein the allele-specific blocker probe comprises a non-extendable, 3'-hexanediol blocker moiety and at least one nucleic acid modification;
      (iv) a detector probe; and
      (v) a locus-specific primer that is complementary to a region of the target sequence, wherein the region of the target sequence complementary to the locus-specific primer is 3' from the first allelic variant and on the opposite strand; and
   (b) carrying out an amplification reaction on the reaction mixture using the locus-specific primer and the allele-specific primer to form an amplicon; and
   (c) detecting the amplicon by detecting a change in a detectable property of the detector probe, thereby detecting the first allelic variant of the target gene in the nucleic acid sample.

2. The method of claim 1, wherein one of the at least one nucleic acid modification in the allele-specific primer is located at the allele-specific nucleotide portion.

3. The method of claim 1, wherein one of the at least one nucleic acid modification in the allele-specific primer is located at the 5'-end and/or 3'-end of the allele-specific primer.

4. The method of claim 1, wherein the allele-specific primer comprises two or more non-consecutive nucleic acid modifications.

5. The method of claim 1, wherein the nucleic acid modification in the allele-specific primer is selected from the group consisting of locked nucleic acids (LNA), peptide nucleic acids (PNA), threose nucleic acids (TNA), zip nucleic acids (ZNA), triazole nucleic acids (TzNA), and combinations thereof.

6. The method of claim 1, wherein one of the at least one nucleic acid modification in the allele-specific blocker probe is located at the allele-specific nucleotide portion.

7. The method of claim 1, wherein one of the at least one nucleic acid modification in the allele-specific blocker probe is located at an internal position in the allele-specific blocker probe.

8. The method of claim 1, wherein the allele-specific blocker probe comprises two or more non-consecutive nucleic acid modifications.

9. The method of claim 1, wherein the nucleic acid modification in the allele-specific blocker probe is selected from the group consisting of locked nucleic acids (LNA), peptide nucleic acids (PNA), threose nucleic acids (TNA), zip nucleic acids (ZNA), triazole nucleic acids (TzNA), and combinations thereof.

10. The method of claim 1, wherein the detector probe comprises a TaqMan® probe.

11. The method of claim 1, wherein the nucleic acid sample is selected from the group consisting of blood, serum, plasma, fine needle aspirate, tumor tissue, and combinations thereof.

12. The method of claim 1, wherein the first allelic variant is a mutant allele and the second allelic variant is the wild-type allele.

13. The method of claim 1, wherein the method reduces the background signal of the second allelic variant during the amplification reaction.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: synthetic G12S ASP-LNA allele-specific real
      time PCR amplification primer
<220> FEATURE:
<221> NAME/KEY: modified_base
<222> LOCATION: (21)...(21)
<223> OTHER INFORMATION: locked nucleic acid,
      2'-O,4'-C-methylene-beta-D-ribofuranosyl adenine
      nucleotide

<400> SEQUENCE: 1
```
aacttgtggt agttggagct a                                              21

<210> SEQ ID NO 2
<211> LENGTH: 19
<212> TYPE: DNA
<213> ORGANISM: Artificial Sequence
<220> FEATURE:
<223> OTHER INFORMATION: synthetic G12S allele-specific blocker-LNA
      probe, G12R allele-specific blocker-LNA probe,
      non-extendable blocker moiety
<220> FEATURE:
<221> NAME/KEY: modified_base
<222> LOCATION: (9)...(9)
<223> OTHER INFORMATION: locked nucleic acid,
      2'-O,4'-C-methylene-beta-D-ribofuranosyl guanine
      nucleotide
<220> FEATURE:
<221> NAME/KEY: modified_base
<222> LOCATION: (19)...(19)
<223> OTHER INFORMATION: g modified by 3'-hexanediol (C6)

<400> SEQUENCE: 2
ttggagctgg tggcgtagg                                                 19

<210> SEQ ID NO 3
<211> LENGTH: 15
<212> TYPE: DNA
<213> ORGANISM: Artificial Sequence
<220> FEATURE:
<223> OTHER INFORMATION: synthetic G12S TaqMan probe, G12R TaqMan probe,
<220> FEATURE:
<221> NAME/KEY: modified_base
<222> LOCATION: (1)...(1)
<223> OTHER INFORMATION: c modified by 6-carboxyfluorescein (6-FAM)
      reporter dye

<400> SEQUENCE: 3
cactcttgcc tacgc                                                     15

<210> SEQ ID NO 4
<211> LENGTH: 26
<212> TYPE: DNA
<213> ORGANISM: Artificial Sequence
<220> FEATURE:
<223> OTHER INFORMATION: synthetic G12S allele-specific real time PCR
      amplification reverse primer, G12R allele-specific
      real time PCR amplification reverse primer

<400> SEQUENCE: 4
tgattctgaa ttagctgtat cgtcaa                                         26

<210> SEQ ID NO 5
<211> LENGTH: 20
<212> TYPE: DNA
<213> ORGANISM: Artificial Sequence
<220> FEATURE:
<223> OTHER INFORMATION: synthetic G12R ASP-LNA allele-specific real
      time PCR amplification primer
<220> FEATURE:
<221> NAME/KEY: modified_base
<222> LOCATION: (20)...(20)
<223> OTHER INFORMATION: locked nucleic acid,
      2'-O,4'-C-methylene-beta-D-ribofuranosyl cytidine
      nucleotide

<400> SEQUENCE: 5
acttgtggta gttggagctc                                                20

<210> SEQ ID NO 6
<211> LENGTH: 23

```
<212> TYPE: DNA
<213> ORGANISM: Artificial Sequence
<220> FEATURE:
<223> OTHER INFORMATION: synthetic H1047R ASP-LNA allele-specific real
      time PCR amplification primer
<220> FEATURE:
<221> NAME/KEY: modified_base
<222> LOCATION: (23)...(23)
<223> OTHER INFORMATION: locked nucleic acid,
      2'-O,4'-C-methylene-beta-D-ribofuranosyl guanine
      nucleotide

<400> SEQUENCE: 6
atgaaacaaa tgaatgatgc acg                                              23

<210> SEQ ID NO 7
<211> LENGTH: 23
<212> TYPE: DNA
<213> ORGANISM: Artificial Sequence
<220> FEATURE:
<223> OTHER INFORMATION: synthetic H1047R allele-specific blocker-LNA
      probe, non-extendable blocker moiety
<220> FEATURE:
<221> NAME/KEY: modified_base
<222> LOCATION: (12)...(12)
<223> OTHER INFORMATION: locked nucleic acid,
      2'-O,4'-C-methylene-beta-D-ribofuranosyl adenine
      nucleotide
<220> FEATURE:
<221> NAME/KEY: modified_base
<222> LOCATION: (23)...(23)
<223> OTHER INFORMATION: t modified by 3'-hexanediol (C6)

<400> SEQUENCE: 7
gaatgatgca catcatggtg gct                                              23

<210> SEQ ID NO 8
<211> LENGTH: 15
<212> TYPE: DNA
<213> ORGANISM: Artificial Sequence
<220> FEATURE:
<223> OTHER INFORMATION: synthetic H1047R TaqMan probe
<220> FEATURE:
<221> NAME/KEY: modified_base
<222> LOCATION: (1)...(1)
<223> OTHER INFORMATION: c modified by FAM fluorophore reporter moiety

<400> SEQUENCE: 8
gttgtccagc cacca                                                       15

<210> SEQ ID NO 9
<211> LENGTH: 26
<212> TYPE: DNA
<213> ORGANISM: Artificial Sequence
<220> FEATURE:
<223> OTHER INFORMATION: synthetic H1047R allele-specific real time PCR
      amplification reverse primer

<400> SEQUENCE: 9
taattgtgtg gaagatccaa tccatt                                           26

<210> SEQ ID NO 10
<211> LENGTH: 19
<212> TYPE: DNA
<213> ORGANISM: Artificial Sequence
<220> FEATURE:
<223> OTHER INFORMATION: synthetic Blocker.1.LNA, allele-specific
      blocker-LNA probe, non-extendable blocker moiety
<220> FEATURE:
<221> NAME/KEY: modified_base
<222> LOCATION: (1)...(1)
```

```
<223> OTHER INFORMATION: locked nucleic acid,
     2'-O,4'-C-methylene-beta-D-ribofuranosyl thymine
     nucleotide
<220> FEATURE:
<221> NAME/KEY: modified_base
<222> LOCATION: (10)...(10)
<223> OTHER INFORMATION: locked nucleic acid,
     2'-O,4'-C-methylene-beta-D-ribofuranosyl guanine
     nucleotide
<220> FEATURE:
<221> NAME/KEY: modified_base
<222> LOCATION: (19)...(19)
<223> OTHER INFORMATION: g modified by 3'-hexanediol (C6)

<400> SEQUENCE: 10
ttggagctgg tggcgtagg                                            19

<210> SEQ ID NO 11
<211> LENGTH: 19
<212> TYPE: DNA
<213> ORGANISM: Artificial Sequence
<220> FEATURE:
<223> OTHER INFORMATION: synthetic Blocker.4.LNA, allele-specific
     blocker-LNA probe, non-extendable blocker moiety
<220> FEATURE:
<221> NAME/KEY: modified_base
<222> LOCATION: (1)...(1)
<223> OTHER INFORMATION: locked nucleic acid,
     2'-O,4'-C-methylene-beta-D-ribofuranosyl thymine
     nucleotide
<220> FEATURE:
<221> NAME/KEY: modified_base
<222> LOCATION: (19)...(19)
<223> OTHER INFORMATION: locked nucleic acid,
     2'-O,4'-C-methylene-beta-D-ribofuranosyl guanine
     nucleotide modified by 3'-hexanediol (C6)

<400> SEQUENCE: 11
ttggagctgg tggcgtagg                                            19

<210> SEQ ID NO 12
<211> LENGTH: 19
<212> TYPE: DNA
<213> ORGANISM: Artificial Sequence
<220> FEATURE:
<223> OTHER INFORMATION: synthetic allele-specific blocker probe,
     non-extendable blocker moiety
<220> FEATURE:
<221> NAME/KEY: modified_base
<222> LOCATION: (19)...(19)
<223> OTHER INFORMATION: g modified by 3'-hexanediol (C6)

<400> SEQUENCE: 12
ttggagctgg tggcgtagg                                            19
```